US011561226B2

(12) United States Patent
Patel et al.

(10) Patent No.: US 11,561,226 B2
(45) Date of Patent: Jan. 24, 2023

(54) DETECTION AND QUANTIFICATION OF AKT-MTOR PATHWAY PROTEINS

(71) Applicant: PIERCE BIOTECHNOLOGY INC., Rockford, IL (US)

(72) Inventors: Bhavinkumar Patel, Rockford, IL (US); John Rogers, Rockton, IL (US)

(73) Assignee: Pierce Biotechnology Inc., Rockford, IL (US)

( * ) Notice: Subject to any disclaimer, the term of this patent is extended or adjusted under 35 U.S.C. 154(b) by 235 days.

(21) Appl. No.: 16/081,377

(22) PCT Filed: Mar. 13, 2017

(86) PCT No.: PCT/US2017/022062
§ 371 (c)(1),
(2) Date: Aug. 30, 2018

(87) PCT Pub. No.: WO2017/160698
PCT Pub. Date: Sep. 21, 2017

(65) Prior Publication Data
US 2019/0086420 A1 Mar. 21, 2019

Related U.S. Application Data

(60) Provisional application No. 62/308,051, filed on Mar. 14, 2016.

(51) Int. Cl.
*G01N 33/574* (2006.01)
*C07K 16/18* (2006.01)
*G01N 33/68* (2006.01)

(52) U.S. Cl.
CPC ....... *G01N 33/57496* (2013.01); *C07K 16/18* (2013.01); *G01N 33/57488* (2013.01); *G01N 33/6848* (2013.01); *G01N 33/6863* (2013.01)

(58) Field of Classification Search
CPC ....... G01N 33/57496; G01N 33/57488; G01N 33/6848; C07K 16/18
See application file for complete search history.

(56) References Cited

U.S. PATENT DOCUMENTS

| 9,110,074 | B2 | 8/2015 | Jamieson Jr. | |
| 9,252,003 | B2 | 2/2016 | Hermanson et al. | |
| 2009/0215098 | A1 | 8/2009 | Cutillas et al. | |
| 2009/0238808 | A1* | 9/2009 | Drewes | G01N 33/6848 424/94.1 |
| 2011/0178273 | A1* | 7/2011 | Aebersold | G01N 33/6848 530/350 |
| 2012/0165340 | A1 | 6/2012 | Furnari et al. | |
| 2012/0295990 | A1* | 11/2012 | Krizman | A61P 35/00 514/789 |
| 2013/0023469 | A1 | 1/2013 | Pikarsky et al. | |
| 2013/0252950 | A1* | 9/2013 | Blenis | G01N 33/68 435/7.1 |
| 2015/0140041 | A1* | 5/2015 | Vitiello | A61K 39/0011 424/277.1 |
| 2016/0067260 | A1 | 3/2016 | Dransfield et al. | |
| 2017/0168055 | A1* | 6/2017 | Krizman | B01D 57/02 |
| 2017/0370942 | A1* | 12/2017 | Picotti | G01N 33/58 |
| 2018/0214452 | A1* | 8/2018 | Lee | A61K 31/5377 |

FOREIGN PATENT DOCUMENTS

| CN | 1551984 A | 12/2004 | |
| CN | 101874037 A | 10/2010 | |
| CN | 102510903 A | 6/2012 | |
| JP | 2009050183 A | 3/2009 | |
| WO | WO-2011140464 A2 * | 11/2011 | ......... G01N 33/6851 |

OTHER PUBLICATIONS

Populo et al. (Int. J. Mol. Sci. 2012 vol. 13, p. 1886-1918). (Year: 2012).*
Anti-human NAB1 (antigen zinc finger transcription factors EGR1 and EGR2)(CD Creative Diagnostic catalog 2015) (Year: 2015).*
B. Patel et al., "Abstract 1837: Quantitative analysis of AKT/mTOR pathway using immunoprecipitation and targeted mass spectrometry 1 Cancer Research", Proceedings of The 1 06th Annual Meeting of the American Association for Cancer Research 2015, Apr. 18-22, Philadelphia PA USA, Cancer Research, val. 75, No. 15 suppl, Aug. 1, 2015 (Aug. 1, 2015), XP055379896, Philadelphia PA USA.
B. Patel et al., "Poster note 64456: Quantitative analysis of IGFIR/AKT/mTOR pathway using multiplex immunoprecipitation and targeted mass spectrometry" In: Mar. 31, 2012 (Mar. 31, 2012). Thermo Fisher Scientific Rockford IL USA, Annual Meeting of the American-Association-For-Cancer-Research; Chicago, IL, USA; Mar. 31-Apr. 4, 2012. XP055394601. ISSN: 0008-5472 pp. 1-3.
Cell Signalling Technology: "Akt (pan) (40D4) Mouse mAb" In: "Akt (pan) (40D4) Mouse mAb", Jan. 4, 2016 (Jan. 4, 2016), Cell Signalling Technology, Leiden NL, XP055394572, pp. 1-2.
Francesca Pezzuto et al, "Update on Head and Neck Cancer: Current Knowledge on Epidemiology, Risk Factors, Molecular Features and Novel Therapies", Oncology, val. 89, No. 3, Jan. 1, 2015 (Jan. 1, 2015), pp. 125-136, XP055380363, Basel ISSN: 0030-2414, DOI: 1 0.1159/000381717.
International Search Report and Written Opinion for Application No. PCT/US2017/022062, datd Aug. 8, 2017, 25 pages.
J. S. Logue and Deborah K. Morrison., "Complexity in the signaling network: insights from the use of targeted inhibitors in cancer therapy", Genes and Development., val. 26, No. 7, Apr. 1, 2012 (Apr. 1, 2012 ), p. 641, XP055380360, Cold Spring Harbour NY USA ISSN: 0890-9369, DOI: 10.1101/gad.186965.112.

(Continued)

*Primary Examiner* — Changhwa J Cheu
(74) *Attorney, Agent, or Firm* — McNeill Baur PLLC

(57) ABSTRACT

This disclosure relates to the field of mass spectrometry analysis. In some embodiments, the disclosure relates to compositions and methods for detecting and quantifying proteins in the AKT-mTOR pathway by immunoprecipitation enrichment followed by mass spectrometry analysis.

18 Claims, 12 Drawing Sheets

Specification includes a Sequence Listing.

(56) References Cited

OTHER PUBLICATIONS

Suzanne Smith et al., "Abstract 1841: Enrichment of IGF1 R-AKT-mTOR pathway proteins using immunoprecipitation and proteomic analysis by mass spectrometry I Cancer Research", Proceedings: American Association for Cancer Research 1 06th Annual Meeting 2015; Apr. 18-22, 2015; Philadelphia, PA, USA. Cancer Research, val. 75, No. 15 Suppl, Aug. 1, 2015 (Aug. 1, 2015 ), XP055379897, Philadelphia PA USA.

Patel et al., Abstract 3884: Quantitative Analysis of IGF1R/AKT/mTOR Pathway Using Multiplex Immunoprecipitation and Targeted Mass Spectrometry, Cancer Research, DOI: 10.1158/1538-7445.AM2016-3884 (2016).

Patel et al., Poster Note 64456: Quantitative Analysis of AKT/mTOR Pathway using Immunoprecipitation and Targeted Mass Spectrometry, Thermo Fisher Scientific, Rockford, IL, USA (2015).

Turney et al: "Depletion of the type 1 IGF receptor delays repair of radiation-induced DNA double strand breaks", Radiotherapy and Oncology, vol. 103, No. 3, Mar. 14, 2012 (Mar. 14, 2012), pp. 402-409, XP028517624, ISSN: 0167-8140, DOI: 10.1016/J.RADONC.2012.03.009 [retrieved on Mar. 22, 2012].

\* cited by examiner

| IP Antibody | Targets Identified | Neat No. of Unique Peptides | IP Enriched No. of Unique Peptides | | Relevant Phosphopeptide ID |
|---|---|---|---|---|---|
| | | | -IGF | +IGF | |
| Phospho AKT | AKT1 | - | 3 | 20 | +IGF: Ser473 |
| | AKT2 | - | - | 14 | +IGF: Ser474 |
| | AKT3 | - | - | 13 | N/A |
| AKT1 | AKT1 | - | 16 | 12 | N/A |
| | AKT2 | - | 9 | 11 | N/A |
| | AKT3 | - | 5 | 3 | N/A |
| Phospho mTOR | mTOR | 2 | 75 | 82 | +IGF: Thr2446, Ser2448 |
| | RICTOR | - | 0 | 2 | N/A |
| | SIN1 | - | 2 | 3 | N/A |
| | Gbl | - | 4 | 4 | N/A |
| IGF1R | IGF1R | 4 | 13 | 13 | N/A |
| | IR | - | 10 | 6 | N/A |
| Phospho IGF1R | IGF1R | 4 | 0 | 5 | +IGF: Tyr1135/1136 |
| PRAS40 | PRAS40 | - | 8 | 8 | +IGF: Thr246 |
| Phospho PRAS40 | PRAS40 | - | 8 | 6 | +IGF: Thr246 |

*FIG. 3*

| Target | Peptide No. | Seq. ID No. | LOD (fmol) | LLOQ (fmol) | ULOQ (fmol) | Linearity ($R^2$) |
|---|---|---|---|---|---|---|
| AKT2 | SDGSFIGYK | 6 | 0.08 | 0.23 | 500 | 0.9998 |
| AKT1 | NDGTFIGYK | 1 | 0.08 | 0.69 | 500 | 0.9981 |
| mTOR | GNNLQDTLR | 96 | 0.08 | 0.23 | 500 | 0.9997 |
| | GYTLADEEEDPLIYQHR | 98 | 0.23 | 0.69 | 500 | 0.9999 |
| IGF1R | TTINNEYNYR | 40 | 0.08 | 0.23 | 500 | 0.9999 |
| | YADGTIDIEEVTENPK | 42 | 0.23 | 0.69 | 500 | 0.9997 |
| IR | TVNESASLR | 23 | 0.08 | 0.08 | 500 | 0.9990 |
| | TIDSVTSAQELR | 16 | 0.08 | 0.23 | 500 | 0.9990 |
| PRAS40 | LNTSDFQK | 200 | 0.23 | 0.69 | 500 | 0.9981 |
| p70S6K | DGFYPAPDFR | 157 | 0.08 | 0.23 | 500 | 0.9980 |
| TSC2 | GYTISDSAPSR | 73 | 0.23 | 0.69 | 500 | 0.9981 |
| | YTEFLTGLGR | 80 | 0.23 | 0.69 | 500 | 0.9980 |
| PTEN | NNIDDVVR | 208 | 0.08 | 0.08 | 500 | 0.9990 |
| | AQEALDFYGEVR | 209 | 0.08 | 0.08 | 500 | 0.9990 |
| GSK3α | VTVVATLGQGPER | 124 | 0.08 | 0.23 | 500 | 0.9980 |
| | SQEVAYTDIK | 120 | 0.23 | 0.69 | 500 | 0.9980 |
| GSK3β | LLEYTPTAR | 133 | 0.08 | 0.23 | 500 | 0.9980 |
| IRS1 | SVSAPQQIINPIR | 57 | 0.08 | 0.08 | 500 | 0.9990 |
| | TGIAAEEVSLPR | 59 | 0.08 | 0.23 | 500 | 0.9985 |

FIG. 4

| Target | 10 Plex Phospho Assay | | 11 Plex Total Assay | |
|---|---|---|---|---|
| | No. of Unique Peptides | | | |
| | -IGF | +IGF | -IGF | +IGF |
| AKT1 | - | 9 | 25 | 30 |
| AKT2 | - | 4 | 24 | 26 |
| mTOR | 48 | 56 | 25 | 28 |
| IGF1R | 1 | 3 | 32 | 35 |
| IR | N/A | N/A | 29 | 26 |
| PRAS40 | 5 | 7 | 9 | 10 |
| p70S6K | 9 | 14 | 11 | 12 |
| TSC2 | 5 | 10 | 42 | 45 |
| PTEN | - | 1 | 5 | 9 |
| GSK3α | 7 | 6 | 19 | 21 |
| GSK3β | 13 | 10 | 23 | 23 |
| IRS1 | 4 | 11 | 45 | 54 |
| PIK3R1 | - | - | - | 22 |
| PIK3CA | - | - | - | 2 |
| PIK3CB | - | - | - | 6 |
| PIK3R2 | - | - | - | 22 |
| GSKIP | - | - | 2 | 2 |
| TSC1 | - | - | 2 | 4 |

*FIG. 5*

| Target | Cell Line | Detected by Q Exactive HF | | Quantified by SRM/PRM | |
|---|---|---|---|---|---|
| | | Neat | Enriched-IP | Neat | Enriched-IP |
| AKT1 | A549 | - | + | - | + |
| | HCT116 | - | + | - | + |
| AKT2 | A549 | - | + | - | + |
| | HCT116 | - | + | - | + |
| mTOR | A549 | + (2) | + (82) | - | + |
| | HCT116 | + (9) | + (110) | - | + |
| IGF1R | A549 | + (4) | + (22) | - | + |
| | HCT116 | - | + | - | + |
| IR | A549 | - | + | - | + |
| | HCT116 | - | + | - | + |
| PRAS40 | A549 | - | + | - | + |
| | HCT116 | + (2) | + (8) | - | + |
| p70S6K | A549 | + (2) | + (7) | - | + |
| | HCT116 | - | + | - | + |
| TSC2 | A549 | - | + | - | + |
| | HCT116 | - | + | - | + |
| PTEN | A549 | - | + | - | + |
| | HCT116 | - | + | - | + |
| GSK3α | A549 | + (5) | + (23) | - | + |
| | HCT116 | - | + (21) | - | + |
| GSK3β | A549 | + (4) | + (12) | - | + |
| | HCT116 | + (3) | + (10) | - | + |
| IRS1 | A549 | - | + | - | + |
| | HCT116 | + (4) | + (10) | - | + |

FIG. 8

Technology Correlation for Total AKT-mTOR Pathway Targets

| Target | Correlation* | Comment |
|---|---|---|
| AKT1 | 3/4 | Low Western correlation |
| IGF1R | 4/4 | Good correlation in all |
| IR | 2.5/4 | Low Luminex correlation, moderate Western |
| IRS1 | 3.5/4 | Moderate ELISA correlation |
| p70S6K | 4/4 | Good correlation in all |
| mTOR | 2.5/4 | Correlation b/w Western & ELISA, correlation b/w IP-MS & Luminex |
| GSK3a | 2.5/4 | Slight correlation b/w all techniques |
| GSK3b | 2.5/4 | Good correlation b/w Western & ELISA, Moderate b/w Luminex & IP-MS |
| PRAS40 | 2/4 | Correlation b/w Luminex & ELISA |
| PTEN | 3.5/4 | Slight difference in Luminex |
| TSC2 | 2/4 | Low ELISA |

FIG. 9

Technology Correlation for Phospho AKT-mTOR Pathway Targets

| Target | Correlation* | Comment |
|---|---|---|
| AKT1 | 2/4 | Correlation b/w Luminex & ELISA |
| AKT2 | 2/4 | Correlation b/w IP-MS & WB |
| IGF1R | 1.5/4 | Low correlation B/W Luminex & ELISA |
| IR | 0/0 | No Ab/Failed for all assays |
| IRS1 | 2/3 | No ELISA Kit ($3500), correlation b/w Luminex & IP-MS |
| p70S6K | 4/4 | Good correlation in all |
| mTOR | 3.5/4 | Slight difference in ELISA |
| GSK3a | 2/3 | ELISA failed, IP-MS & WB concur |
| GSK3b | 2/3 | ELISA failed, Luminex & WB concur |
| PRAS40 | 1.5/2 | No correlation, Luminex & ELISA Failed |
| PTEN | 2/4 | Correlation b/w WB and ELISA |
| TSC2 | 1.5/4 | No correlation b/w assays |

FIG. 10

IP to WB Validation of AKT-mTOR Pathway Targets

| Target-Phos | Good WB Ab? | # Attempts to Validate ≥ 1 Ab# |
|---|---|---|
| pAKT1 | Y | 6 |
| pIR* | Y | 8 |
| pIGF1R* | Y | 7 |
| pIRS1* | Y | 4 |
| pmTOR* | Y | 5 |
| pP70S6K-b | Y | 1 |
| pGSK3a | Y | 3 |
| pGSK3b | Y | 4 |
| pTSC2* | Y | 10 |
| pRPS6 | Y | 2 |
| pPRAS40 | Y | 2 |
| pPTEN | Y | 2 |

| Target-Total | Good WB Ab? | # Attempts to Validate ≥ 1 Ab# |
|---|---|---|
| AKT1 | Y | 1 |
| IR* | Y | 4 |
| IGF1R* | Y | 3 |
| IRS1* | Y | 3 |
| mTOR* | Y | 3 |
| P70S6K-b | Y | 1 |
| pGSK3a | Y | 1 |
| pGSK3b | Y | 2 |
| TSC2* | Y | 3 |
| RPS6 | Y | 2 |
| PRAS40 | Y | 3 |
| PTEN | Y | 1 |

\* Notates optimized protocol for high-molecular weight targets

FIG. 11

DETECTION AND QUANTIFICATION OF AKT-MTOR PATHWAY PROTEINS

CROSS-REFERENCE TO RELATED APPLICATIONS

This application is a 371 of International Application No. PCT/US2017/022062, filed Mar. 13, 2017, which claims the benefit of priority of U.S. Provisional Patent Application No. 62/308,051, filed Mar. 14, 2016, which is incorporated by reference herein in its entirety for all purposes.

SEQUENCE LISTING

The instant application contains a sequence listing which has been submitted electronically in ASCI format and is hereby incorporated by reference in its entirety. Said ASCII copy, created on Aug. 27, 2018, is named LT01152US SL.txt and is 154,793 bytes in size.

FIELD OF INVENTION

This disclosure relates to the field of detection and quantification of AKT-mTOR pathway proteins, including phosphorylated proteins, by immunoprecipitation and mass spectrometry.

BACKGROUND

The AKT-mTOR pathway plays a central role in tumor progression and anti-cancer drug resistance. The quantitative measurement of protein expression and post-translational modifications of the AKT-mTOR pathway is necessary for precisely characterizing cancer, monitoring cancer progression, and determining treatment responses. See Logue, J. S.; Morrison, D. K.; *Genes Dev. Apr.* 1 2012, 26 (7), 641-50.

A major limitation in the detection and quantitation of AKT-mTOR pathway proteins is the lack of rigorously validated methods and reagents. Currently, only semi-quantitative results from Western blotting, ELISA, and Luminex assays are available. Mass spectrometry (MS) is increasingly becoming the detection methodology of choice for assaying protein abundance and post-translational modifications. However, to date, MS has not been successful in quantifying AKT-mTOR pathway proteins, possibly due to their low abundance and significant post-translational modification profiles.

Immunoprecipitation (IP) is commonly used upstream of MS as an enrichment tool for low-abundant protein targets. See, Gingras et al., *Nat. Rev. Mol. Cell. Biol., Aug.* 2007, 8 (8), 645-54; and Carr, S. A. et al., *Mol. Cell. Proteomics Mar.* 2014, 13 (3), 907-17. The identification of appropriate antibodies for use in IP upstream of MS is important, as not all antibodies that bind to protein will be effective immunoprecipitation tools, and further, not all antibodies that are effective immunoprecipiation tools will lead to successful identification via MS.

SUMMARY OF INVENTION

The present disclosure provides reagents and methods for detecting and quantifying AKT-mTOR pathway proteins via immunoprecipitation (IP), mass spectrometry (MS), and immunoprecipitation followed by mass spectrometry (IP-MS).

In some embodiments, methods for immunoprecipitating an AKT-mTOR pathway protein (target protein) are provided, comprising contacting a biological sample with any one of the antibodies recited in Table 1. In some embodiments, the antibodies useful in the IP methods comprise the antibodies recited in Table 8. In some embodiments, the antibodies useful in the IP methods comprise the antibodies recited in Table 9. The methods may comprise washing the contacted biological sample to enrich for antibody-protein conjugates. Further methods include detecting the antibody-protein conjugates (the immunoprecipitated target protein) to determine the AKT-mTOR pathway protein in the biological sample. In some embodiments, the antibody is labelled. In some embodiments, a detection reagent is provided to the enriched antibody-protein conjugate. In some embodiments the label is biotin and the detection reagent is streptavidin.

In some embodiments the IP is single-plex. In some embodiments the IP is multi-plex. The antibodies useful in multi-plex IP may comprise the antibodies of Table 8 and Table 9.

In some embodiments a method for detecting AKT-mTOR pathway proteins via MS is provided, comprising isolating proteins from a biological sample, digesting the isolated proteins, assaying the digested proteins via mass spectrometry to determine the presence of a peptide for AKT-mTOR pathway protein(s), and determining the identity of one or more AKT-mTOR pathway protein(s) in the sample. In some embodiments, the peptide for AKT-mTOR pathway protein(s) comprises a sequence of SEQ ID NO: 1-SEQ ID NO: 424. In some embodiments the peptide is less than 40 amino acids in length. In some embodiments, the peptide for AKT-mTOR pathway protein(s) consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424.

In some embodiments a method for quantifying AKT-mTOR pathway proteins via MS is provided, comprising isolating proteins from a biological sample, digesting the isolated proteins, assaying the digested proteins via mass spectrometry to determine the presence of a peptide for AKT-mTOR pathway protein(s), and determining the quantity of one or more AKT-mTOR pathway protein(s) in the sample. In some embodiments, the peptide for AKT-mTOR pathway protein(s) comprises a sequence of SEQ ID NO: 1-SEQ ID NO: 424. In some embodiments the peptide is less than 40 amino acids in length. In some embodiments, the peptide for AKT-mTOR pathway protein(s) consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments a method for detecting AKT-mTOR pathway proteins via IP-MS is provided, comprising treating a biological sample with at least one antibody capable of immunoprecipitating AKT-mTOR target pathway protein(s) from a biological sample, digesting the isolated proteins, assaying the digested proteins via mass spectrometry to determine the presence of a peptide for AKT-mTOR pathway protein(s), and determining the identity of one or more AKT-mTOR pathway protein(s) in the sample. In some embodiments, the peptide for AKT-mTOR pathway protein(s) comprises a sequence of SEQ ID NO: 1-SEQ ID NO: 424. In some embodiments the peptide is less than 40 amino acids in length. In some embodiments, the peptide for AKT-mTOR pathway protein(s) consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments a method for quantifying AKT-mTOR pathway proteins via IP-MS is provided, comprising treating a biological sample with at least one antibody capable of immunoprecipitating AKT-mTOR target pathway protein(s) from a biological sample, digesting the isolated proteins, assaying the digested proteins via mass spectrometry to determine the presence of a peptide for AKT-mTOR pathway protein(s), and determining the quantity of one or more AKT-mTOR pathway protein(s) in the sample. In some embodiments, the peptide for AKT-mTOR pathway protein (s) comprises a sequence of SEQ ID NO: 1-SEQ ID NO: 424. In some embodiments the peptide is less than 40 amino acids in length. In some embodiments, the peptide for AKT-mTOR pathway protein(s) consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments the AKT-mTOR pathway target protein is phosphorylated.

Methods for determining the ratio of phosphorylated to non-phosphorylated AKT-mTOR pathway proteins are provided, comprising any of the above IP, MS, or MS-IP methods, wherein a further step of determining the ratio of phosphorylated to non-phosphorylated protein is provided. In some embodiments, the method is an MS-IP method comprising treating a biological sample with one or more antibodies capable of immunoprecipitating one or more phosphorylated AKT-mTOR pathway proteins, and separately treating the same biological sample with one or more antibodies capable of immunoprecipitating at least one or more of the same or different non-phosphorylated AKT-mTOR pathway proteins; digesting the immunoprecipitated AKT-mTOR pathway proteins; adding a first and a second detectably labelled internal standard peptide of known amount to the digested proteins, wherein the first internal standard peptide has the same amino acid sequence as a phosphorylated AKT-mTOR pathway peptide used to identify the phosphorylated protein, and the second internal standard peptide has the same amino acid sequence as the non-phosphorylated AKT-mTOR pathway peptide used to identify the non-phosphorylated protein; assaying the digested protein and internal standards via mass spectrometry to determine the presence and amount of phosphorylated and non-phosphorylated AKT-mTOR pathway proteins, wherein the AKT-mTOR pathway peptide comprises a peptide of SEQ ID NO: 1-SEQ ID NO: 424, and is less than 40 amino acids in length; determining the quantity of AKT-mTOR phosphorylated and non-phosphorylated pathway proteins in the sample, and determining the ratio of phosphorylated to non-phosphorylated pathway proteins. In some embodiments, the peptide for AKT-mTOR pathway protein(s) consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments, the biological sample is human. In some embodiments, the biological sample is non-human. In some embodiments, the biological sample is mammalian. In some embodiments, the biological sample is from rat, mouse, guinea pig, hamster, cow, pig, horse, goat, sheep, dog, cat, or non-human primate.

In embodiments utilizing an AKT-mTOR pathway peptide, the peptide may be modified with a detectable label. The detectable label may comprise an isotope, such as a heavy isotope, such as those known to those of skill in the art, including 13C, 15N, 2H and 18O. In some embodiments, the modified/labelled peptide comprises a peptide of SEQ ID NO: 213-424. In some embodiments the peptide is less than 40 amino acids in length. In some embodiments the modified/labelled peptide consists of a peptide of SEQ ID NO: 213-424. In some embodiments the modified/labelled peptide consists of a peptide of SEQ ID NO: 213-424, wherein the peptide is further modified.

In some embodiments, the antibody for IP is selected from the group consisting of the antibodies recited in Table 1. In some embodiments, the antibody for IP is an antibody having the six CDRs of any of the antibodies of Table 1. The antibody may be capable of immunoprecipitating more than one AKT-mTOR pathway protein. In some embodiments the antibody is labelled or capable of being labelled. The label may be any label known to those of skill in the art including enzymatic and fluorescent labels, such as biotin. In some embodiments more than one antibody is used in a multi-plex IP. In some embodiments, the multi-plex IP comprises the antibodies of Table 8. In some embodiments, the multi-plex IP comprises the antibodies of Table 9.

In some embodiments, two or more antibodies are utilized to analyze one biological sample. For example, a first antibody is capable of immunoprecipitating a phosphorylated AKT-mTOR pathway protein, and a second antibody is capable of immunoprecipitating a non-phosphorylated version of the AKT-mTOR pathway protein precipitated by the first antibody. In some embodiments, a single antibody is capable of immunoprecipitating a phosphorylated and non-phosphorylated AKT-mTOR pathway protein.

In some embodiments, the immunoprecipitation comprises treating a sample with a labelled antibody capable of binding to an AKT-mTOR pathway protein to provide a labelled antibody-protein conjugate. The method may further comprise contacting the labelled antibody-protein conjugate with a capture agent capable of binding to the labelled antibody to isolate the pathway protein from the sample. The label may be biotin and the capture agent may be streptavidin.

The quantity of an AKT-mTOR pathway protein may be determined by adding an internal standard peptide of known amount to the digested protein prior to mass spectrometry. In some embodiments, the internal standard peptide has the same amino acid sequence as the AKT-mTOR pathway peptide. In some embodiments, the internal standard is detectably labeled. The method may further comprises determining the quantity of an AKT-mTOR pathway peptide by comparison to the internal standard.

In some embodiments, the internal standard peptide comprises a sequence of SEQ ID NO: 1-SEQ ID NO: 424. In some embodiments the peptide is less than 40 amino acids in length. In some embodiments, the peptide consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments, quantifying the AKT-mTOR pathway protein comprises comparing an amount of an AKT-mTOR pathway peptide in the sample to an amount of the same AKT-mTOR pathway peptide in a control sample.

Quantifying an AKT-mTOR pathway protein may comprise comparing an amount of an AKT-mTOR pathway peptide to an internal standard peptide of known amount, wherein both the peptide in the biological sample and the internal standard peptide comprise SEQ ID NO: 1-SEQ ID NO: 424, wherein the standard peptide is detectably labeled, and wherein the peptide is less than 40 amino acids long. In some embodiments, the standard peptide consists of a sequence of SEQ ID NO: 1-SEQ ID NO: 424. The peptides of SEQ ID NO: 1-SEQ ID NO: 212 may be labelled. In some embodiments the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments the mass spectrometry is selected from tandem mass spectrometry and discovery mass spectrometry. The targeted mass spectrometry may be selected from multiple reaction monitoring (MRM), selected reaction monitoring (SRM), and parallel reaction monitoring (PRM), or combinations thereof.

In some embodiments the biological sample is selected from isolated human cells, plasma, serum, whole blood, CSF, urine, sputum, tissue, and tumorous tissue.

In some embodiments, the method further comprises quantifying the relative amount of AKT-mTOR pathway protein. In some embodiments, the method further comprises quantifying the absolute amount of AKT-mTOR pathway protein.

In some embodiments, the digesting comprises a protease or chemical digest. In some embodiments the digestion may be single or sequential. The protease digestion may comprise trypsin, chymotrypsin, AspN, GluC, LysC, LysN, ArgC, proteinase K, pepsin, clostripain, elastase, GluC biocarb, LysC/P, LysN promisc, protein endopeptidase, staph protease or thermolysin.

The chemical cleavage may comprise CNBr, iodosobenzoate or formic acid.

In some embodiments the digestion is a protease digest with trypsin.

In some embodiments the methods further comprise desalting after digestion and prior to mass spectrometry.

The AKT-mTOR pathway protein may be selected from AKT1 (UniProtKB—P31749), AKT2 (UniProtKB—P31751), IR (also known as INSR) (UniProtKB P06213), IGF1R (UniProtKB—P08069), IRS1 (UniProtKB—P35568), TSC2 (UniProtKB—P49815), mTOR (UniProtKB—P42345), GSK3a (UniProtKB—P49840), GSK3b (UniProtKB—P49841), GSK3a/GSK3b, p70S6K (also known as RPS6KB1) (UniProtKB—P23443), RPS6 (UniProtKB—P62753), PRAS40 (also known as AKT1S1) (UniProtKB—Q96B36), and PTEN (UniProtKB—P60484).

In some embodiments, the AKT-mTOR pathway is a protein that interacts with any of AKT1 (UniProtKB—P31749), AKT2 (UniProtKB—P31751), IR (also known as INSR) (UniProtKB P06213), IGF1R (UniProtKB—P08069), IRS1 (UniProtKB—P35568), TSC2 (UniProtKB—P49815), mTOR (UniProtKB—P42345), GSK3a (UniProtKB—P49840), GSK3b (UniProtKB—P49841), GSK3a/GSK3b, p70S6K (also known as RPS6KB1) (UniProtKB—P23443), RPS6 (UniProtKB—P62753), PRAS40 (also known as AKT1S1) (UniProtKB—Q96B36), and PTEN (UniProtKB—P60484).

In some embodiments, the AKT-mTOR pathway protein is phosphorylated.

In some embodiments, the concentration of AKT-mTOR protein that may be detected ranges from about 0.08 fmol to about 2000 fmol.

In some embodiments, the lower limit of detection is about 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25 fmol. The lower limit of detection may be within the range of about 0.05-0.25 fmol.

In some embodiments the lower limit of quantification is about 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.30, 0.35, 0.40, 0.45, 0.50, 0.55, 0.60, 0.65, 0.70, or 0.75 fmol. The lower limit of quantification may be within the range of about 0.05-0.75 fmol.

Kits comprising one or more antibodies capable of immunoprecipitating an AKT-mTOR pathway protein are encompassed.

Kits comprising one or more antibodies capable of immunoprecipitating an AKT-mTOR pathway protein, and reagents useful for performing mass spectrometry to detect an AKT-mTOR pathway protein are also provided.

Also encompassed are kits comprising one or more antibodies capable of immunoprecipitating an AKT-mTOR pathway target protein, and reagents useful for performing mass spectrometry to quantify an AKT-mTOR pathway protein.

The antibody to be included in the kit may be selected from any one or more of the antibodies recited in Table 1. In some embodiments the antibody is labelled or capable of being labelled. The label may be any label known to those of skill in the art including enzymatic and fluorescent labels, such as biotin. In some embodiments, the kit comprises more than one antibody. In some embodiments, the kit comprises two or more of the antibodies selected from the antibodies recited in Table 8. In some embodiments, the kit comprises two or more of the antibodies selected from the antibodies recited in Table 9. In some embodiments, the kit comprises two or more of the antibodies selected from the antibodies recited in Table 8 and two or more of the antibodies selected from the antibodies recited in Table 9. In some embodiments, the kit comprises each of the antibodies recited in Table 8, Table 9, or Tables 8 and 9.

The kits may further comprise an AKT-mTOR pathway peptide. In some embodiments, the peptide comprises a sequence of SEQ ID NO: 1-SEQ ID NO: 424. In some embodiments, the peptide is less than 40 amino acids in length. In some embodiments, the peptide consists of a sequence of SEQ ID NO: 1-SEQ ID NO: 424. The peptides of SEQ ID NO: 1-SEQ ID NO: 212 may be labelled. In some embodiments, the label on SEQ ID NO: 1-SEQ ID NO: 212 differs from the label shown on the peptides of SEQ ID NO: 213-SEQ ID NO: 424. In some embodiments, the peptide comprises or consists of a peptide selected from the peptides shown in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204).

In some embodiments, the kit may comprise at least one peptide selected from peptides of SEQ ID NO: 213-SEQ ID NO: 424, wherein the peptide is less than or equal to 40 amino acids. In one embodiment, the kit comprises at least one peptide consisting of the peptides of SEQ ID NO: 213-SEQ ID NO: 424.

The peptides provided in the kit may be detectably labeled or capable of being modified to be detectably labeled. In some embodiments, the kit may comprise at least one peptide selected from peptides of SEQ ID NO: 1-SEQ ID NO: 212, wherein the peptide is detectably labeled or capable of being modified to be detectably labeled.

In some embodiments, the kit further comprises a protease or chemical agent capable of digesting an immunoprecipitated protein sample. The protease agent may be trypsin, chymotrypsin, AspN, OluC, Lyse, LysN, ArgC, proteinase K, pepsin, clostripain, elastase, GluC biocarb, LysC/P, LysN promisc, protein endopeptidase, Staph protease or thermolysin. The chemical agent may be CNBr, iodosobenzoate or formic acid.

The kits may be utilized to detect AKT-mTOR pathway proteins, including AKT1 (UniProtKB—P31749); AKT2 (UniProtKB—P31751), IR (also known as INSR) (UniProtKB P06213), IGF1R (UniProtKB—P08069), IRS1 (UniProtKB—P35568), TSC2 (UniProtKB—P49815), mTOR (UniProtKB—P42345), GSK3a (UniProtKB—P49840), GSK3b (UniProtKB—P49841), GSK3a/GSK3b, p70S6K (also known as RPS6KB1) (UniProtKB—P23443 (KS6B1_HUMAN)), RPS6 (UniProtKB—P62753), PRAS40 (also known as AKT1S1)(UniProtKB—Q96B36), and PTEN (UniProtKB—P60484).

The AKT-mTOR protein to be detected and quantified by the kits may be phosphorylated.

Also encompassed are antibodies recited in Table 1 for use in immunoprecipitating an AKT-mTOR pathway protein. The antibody may be used in methods comprising immunoprecipitating an AKT-mTOR pathway protein prior to analyzing the protein via mass spectrometry.

AKT-mTOR pathway peptides selected from the peptides of Table 3 are encompassed. The AKT-mTOR pathway peptides may be used in methods of detecting and quantifying AKT-mTOR pathway proteins in biological samples. The AKT-mTOR pathway peptides may be used in methods comprising immunoprecipitating the AKT-mTOR pathway protein from the biological sample, and analyzing the immunoprecipitated protein via mass spectrometry.

BRIEF DESCRIPTION OF DRAWINGS

FIG. 3 shows results from an experiment to enrich for low abundant AKT-mTOR pathway proteins from A549 cells.

FIG. 4 shows detection and quantitation limits of peptides for 12 AKT-mTOR pathway proteins.

FIG. 5 shows the results of a multiplex immunoprecipitation plus nanoLC-MS/MS assay for 10 phosphorylated and 11 total AKT-mTOR pathway proteins.

FIG. 8 shows a summary of AKT-mTOR pathway proteins identified and quantified in two different cell lines, with and without immunoprecipitation enrichment, using the mass spec methods.

FIG. 9 shows technology correlation for total AKT-mTOR pathway targets.

FIG. 10 shows technology correlation for phopho-AKT-mTOR pathway targets.

FIG. 11 shows IP to Western Blot validation of AKT-mTOR pathway targets.

DESCRIPTION OF THE EMBODIMENTS

Figure 1:
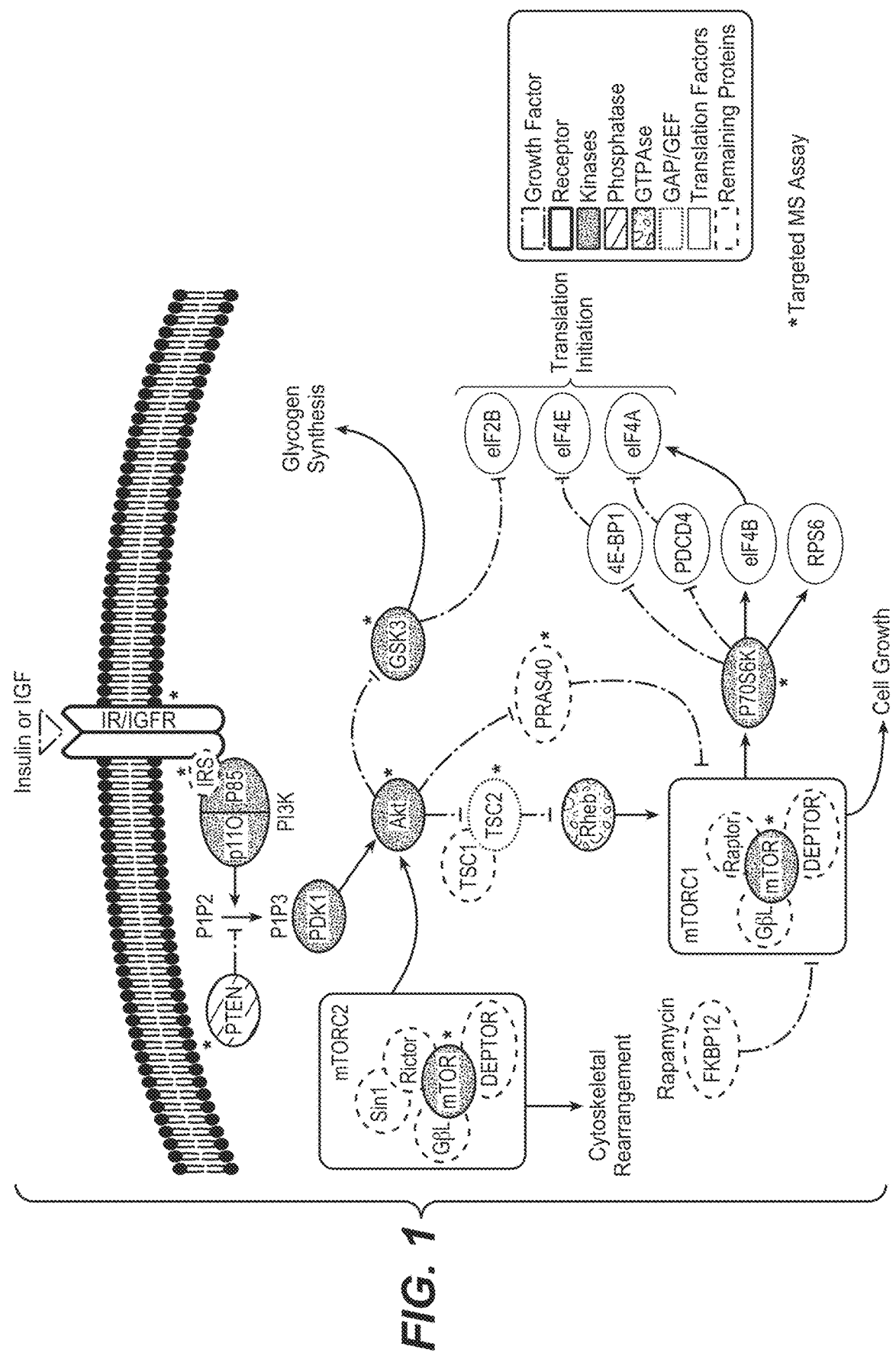
FIG. 1 shows a schematic of the AKT-mTOR pathway proteins.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

As used herein, an "AKT-mTOR pathway protein" includes, but is not limited to, AKT1 (UniProtKB—P31749), AKT2 (UniProtKB—P31751), IR (also known as INSR) (UniProtKB P06213), IGF1R (UniProtKB—P08069), IRS1 (UniProtKB—P35568), TSC2 (UniProtKB—P49815), mTOR (UniProtKB—P42345), GSK3a (UniProtKB—P49840), GSK3b (UniProtKB—P49841), GSK3a/GSK3b, p70S6K (also known as RPS6KB1) (UniProtKB—P23443), RPS6 (UniProtKB—P62753), PRAS40 (also known as AKT1S1) (UniProtKB—Q96B36), and PTEN (UniProtKB—P60484).

As used herein "protein", "peptide", and "polypeptide" are used interchangeably throughout to mean a chain of amino acids wherein each amino acid is connected to the next by a peptide bond. In some embodiments, when a chain of amino acids consists of about two to forty amino acids, the term "peptide" is used. However, the term "peptide" should not be considered limiting unless expressly indicated.

The term "antibody" is used in the broadest sense and encompasses various antibody structures, including but not limited to monoclonal antibodies, polyclonal antibodies, multispecific antibodies (such as bispecific antibodies), and antibody fragments so long as they exhibit the desired immunoprecipitating activity. As such, the term antibody includes, but is not limited to, fragments that are capable of binding to an antigen, such as Fv, single-chain Fv (scFv), Fab, Fab', di-scFv, sdAb (single domain antibody) and (Fab')$_2$ (including a chemically linked F(ab')$_2$). Papain digestion of antibodies produces two identical antigen-binding fragments, called "Fab" fragments, each with a single antigen-binding site, and a residual "Fc" fragment. Pepsin treatment yields a F(ab')$_2$ fragment that has two antigen-binding sites. The term antibody also includes, but is not limited to, chimeric antibodies, humanized antibodies, and antibodies of various species such as mouse, goat, horse, sheep, chicken, etc. Furthermore, for all antibody constructs provided herein, variants having the sequences from other organisms are also contemplated, such as CDR-grafted antibodies or chimeric antibodies. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, human scFv or a mouse scFv). This denotes the sequences of at least part of the non-CDR regions, rather than the source of the construct. The antibodies provided herein are referred to by reference to name and catalog reference. The skilled artisan, holding this name and catalog information, is capable of determining the sequence of the antibody, and therefore the disclosure encompasses any antibody having at least partial sequence of a reference antibody so long as the antibody maintains its ability to immunoprecipitate its antigen protein. In some embodiments, the antibodies comprise antibodies having the same CDRs as the antibodies provided in Table 1.

Mass spectrometry (MS) is a primary technique for analysis of proteins on the basis of their mass-to-charge ratio (m/z). MS techniques generally include ionization of compounds and optional fragmentation of the resulting ions, as well as detection and analysis of the m/z of the ions and/or fragment ions followed by calculation of corresponding ionic masses. A "mass spectrometer" generally includes an ionizer and an ion detector. "Mass spectrometry," "mass spec," "mass spectroscopy," and "MS" are used interchangeably throughout.

"Targeted mass spectrometry," also referred to herein as "targeted mass spec," "targeted MS," and "tMS" increases the speed, sensitivity, and quantitative precision of mass spec analysis. Non-targeted mass spectrometry, sometimes referred to as "data-dependent scanning," "discovery MS," and "dMS" and targeted mass spec are alike in that in each, analytes (proteins, small molecules, or peptides) are infused or eluted from a reversed phase column attached to a liquid chromatography instrument and converted to gas phase ions by electrospray ionization. Analytes are fragmented in the mass spec (a process known as tandem MS or MS/MS), and fragment and parent masses are used to establish the identity of the analyte. Discovery MS analyzes the entire content of the MS/MS fragmentation spectrum. In contrast, in targeted mass spectrometry, a reference spectrum is used to guide analysis to only a few selected fragment ions rather than the entire content.

"Multiple reaction monitoring," "MRM," "selected reaction monitoring," and "SRM" are used interchangeably throughout to refer to a type of targeted mass spectrometry that relies on a unique scanning mode accessible on triple-quadrupole (QQQ) instruments. See, e.g., Chambers et al., *Expert Rev. Proteomics*, 1-12 (2014).

"Parallel Reaction Monitoring," and "PRM" are used interchangeably herein to describe another type of targeted mass spec wherein the second mass analyzer used in SRM (quadrupole) is substituted by a high resolution orbitrap mass analyzer in PRM. Unlike SRM, which allows the measuring of one single transition at a given point in time, PRM allows parallel monitoring in one MS/MS spectrum. PRM also allows for the separation of ions with close m/z values (i.e., within a 10 ppm range), and may therefore allow for lower limits of detection and quantification (LOD or LLOD and LOQ or LLOQ).

The methods disclosed herein may be applied to any type of MS analysis. The disclosure is not limited by the specific equipment or analysis used. The use of any equipment with the intent of analyzing the m/z of a sample would be included in the definition of mass spectrometry. Non-limiting examples of MS analysis and/or equipment that may be used include electrospray ionization, ion mobility, time-of-flight, tandem, ion trap, MRM, SRM, MRM/SRM, PRM, and Orbitrap. The disclosure is neither limited by the type of ionizer or detector used in the MS analysis nor by the specific configuration of the MS. The disclosure is not limited to use with specific equipment or software. The disclosure is not limited to the equipment and software described in the Examples.

In some embodiments, methods of immunoprecipitating an AKT-mTOR pathway protein are provided, comprising contacting a biological sample with at least one antibody recited in Table 1. The immunoprecipitating method may be single-plex or multi-plex. A "single-plex" IP utilizes one antibody per assay, whereas a "multi-plex" IP utilizes more than one antibody per assay.

In some embodiments, an IP-MS method for detecting and quantifying phosphorylated and non-phosphorylated AKT-mTOR pathway proteins is provided. The methods may comprise contacting a biological sample with at least one antibody recited in Table 1, digesting the immunoprecipitated protein(s), and assaying the digested proteins via mass spectrometry. The IP and MS may be single-plex or multi-plex. A "single-plex" MS refers to monitoring a single peptide in a single MS run, whereas a "mulit-plex" MS refers to monitoring more than one target peptides in a single MS run.

Table 1 provides a listing of antibodies useful in the IP and IP-MS methods described herein. Table 2 provides a listing of antibodies that are known to bind to their antigen AKT-mTOR protein, but were found to be less useful in the IP and IP-MS methods described herein. FIG. 11 and Table 3 provide a summary of antibodies useful in IP of AKT-mTOR pathway proteins, as validated by Western Blot.

TABLE 1

List of IP to MS validated antibodies for AKT-mTOR Pathway Proteins

| Antibody Name | Company/Catalog Number |
|---|---|
| AKT1 Antibody | Millipore/07-416 |
| AKT (pan) Antibody | Cell Signaling Technology/2920 |
| AKT2 Antibody | Cell Signaling Technology/3063 |
| phospho AKT2 (pSer474) Antibody | Thermo Fisher Scientific/PA5-35676 |
| AKT1 Antibody | Cell Signaling Technology/2967 |
| phospho AKT (pSer473) Antibody | Thermo Fisher Scientific/700392 |
| phospho AKT (pSer473) Antibody | Cell Signaling Technology/4060 |
| Anti-phospho-IGF-1R (Tyr1161/Tyr1165/Tyr1166) Antibody | Millipore/ABE332 |
| Phospho-IGF1 Rec pTyr1158 + 1162 + 1163 Antibody | Thermo Fisher Scientific/PA1-26725 |
| Phospho-IGF1R pTyr1161 Antibody | Thermo Fisher Scientific/PA5-35769 |
| Phospho-IGF-I Receptor β (Tyr1131)/Insulin Receptor β (Tyr1146) Antibody | Cell Signaling Technology/3021 |
| IGF-I Receptor β Antibody | Cell Signaling Technology/9750 |
| IGF-I Receptor β Antibody | Cell Signaling Technology/3027 |
| Insulin Receptor β Antibody | Cell Signaling Technology/3020 |
| INSR/Insulin Receptor Antibody | Thermo Fisher Scientific/MA1-10865 |
| Anti-α-Insulin Receptor Antibody, β subunit Antibody | Millipore/07-724 |
| INSR/Insulin Receptor alpha Antibody | Thermo Fisher Scientific/MA5-13759 |
| Anti-Insulin Receptor (phospho Y972) Antibody | abcam/ab5678 |
| IRS-1 Antibody | Cell Signaling Technology/2382 |
| IRS-1 Antibody | Cell Signaling Technology/3407 |
| IRS-1 Antibody | Millipore/06-248 |
| IRS-1 Antibody | Millipore/05-784R |
| IRS-1 Antibody | Millipore/05-1085 |
| IRS1 (pSer312) polyclonal Antibody | Abnova/PAB12627 |
| Anti-phospho-IRS1 (Ser307 mouse/Ser312 human) Antibody | Millipore/05-1087 |
| Phospho-IRS-1 (pSer1101) Antibody | Cell Signaling Technology/2385 |
| mTOR Antibody | Cell Signaling Technology/2972 |
| mTOR Antibody | Millipore/07-1415 |
| mTOR Antibody | abcam/ab2732 |
| mTOR Antibody | abcam/ab25880 |
| mTOR Antibody | Thermo Fisher Scientific/PA1-518 |
| Phospho-mTOR (pSer2448) Antibody | Thermo Fisher Scientific/PA5-35652 |
| Phospho-mTOR (pSer2448) Antibody | Cell Signaling Technology/5536 |
| Phospho-mTOR (pSer2448) Antibody | Abgent/AP50437 |
| S6K Antibody | Thermo Fisher Scientific/PA5-12726 |
| S6K Antibody | Thermo Fisher Scientific/PA5-12723 |
| S6K1 Antibody | Thermo Fisher Scientific/PA1-31167 |
| Anti-S6K1 Antibody | abcam/ab9366 |
| S6K Antibody | Thermo Fisher Scientific/PA5-27853 |
| Phospho-p70 S6 Kinase (pThr389/pThr412) Antibody | Thermo Fisher Scientific/PA5-35701 |
| Phospho-p70 S6 Kinase (pThr389) Antibody | Thermo Fisher Scientific/701064 |
| Phospho-p70 S6 Kinase (pThr421/pSer424) Antibody | Cell Signaling Technology/9204 |
| Phospho-p70 S6 Kinase pThr389 Antibody | Thermo Fisher Scientific/MA5-15202 |
| Phospho-GSK-3α/β (pSer21/pSer9) Antibody | Cell Signaling Technology/9327 |
| GSK3α Antibody | Cell Signaling Technology/4337 |
| GSK3α Antibody | Cell Signaling Technology/4818 |
| Phospho-GSK-3α (Ser21) Antibody | Cell Signaling Technology/8452 |
| Phospho-GSK-3α (Ser21) Antibody | Cell Signaling Technology/9316 |
| Phospho-GSK-3α/β (pSer21/pSer9) Antibody | Cell Signaling Technology/8566 |
| GSK3β Antibody | Thermo Fisher Scientific/MA5-15109 |
| GSK3β Antibody | Thermo Fisher Scientific/PA5-29251 |
| GSK3β Antibody | Thermo Fisher Scientific/PA5-29265 |
| GSK3β Antibody | Cell Signaling Technology/12456 |
| Phospho-GSK-3β (pSer9) Antibody | Cell Signaling Technology/5558 |
| Phospho-Tuberin/TSC2 pSer939 Antibody | Thermo Fisher Scientific/710395 |
| Phospho-TSC2 pSer939 Antibody | Thermo Fisher Scientific/PA5-12845 |
| Phospho-TSC2 pSer939 Antibody | abcam/ab59269 |
| Phospho-TSC2 pSer939 Antibody | abcam/ab52962 |
| Anti-TSC2 Antibody | abcam/ab52936 |
| Anti-TSC2 Antibody | Cell Signaling Technology/4308 |
| Anti-TSC2 Antibody | Thermo Fisher Scientific/PA5-20132 |
| Anti-TSC2 Antibody | Cell Signaling Technology/3990 |
| Anti-TSC2 Antibody | Thermo Fisher Scientific/MA5-15004 |
| S6 Ribosomal Protein Antibody | Thermo Fisher Scientific/701374 |
| S6 Ribosomal Protein Antibody | Thermo Fisher Scientific/710405 |
| S6 Ribosomal Protein Antibody | Thermo Fisher Scientific/PA5-11818 |
| Phospho-S6 Ribosomal Protein pSer235 + 236 Antibody | Thermo Fisher Scientific/701363 |
| RPS6 Antibody | Thermo Fisher Scientific/PA5-26041 |
| Anti-PRAS40 Antibody | abcam/ab72321 |
| Anti-PRAS40 Antibody | Thermo Fisher Scientific/PA5-35143 |
| Anti-PRAS40 Antibody | R&D System/MAB6408 (R&D) |
| Anti-PRAS40 Antibody | Cell Signaling Technology/2691 |
| Phospho-PRAS40 (pThr246) Antibody | Cell Signaling Technology/2997 |
| Phospho-PRAS40 (pThr246) Antibody | Cell Signaling Technology/13175 |
| Phospho-PRAS40 (pThr246) Antibody | R&D System/MAB6890 |
| Phospho-PTEN (pSer380) Antibody | Cell Signaling Technology/9551 |
| PTEN Antibody | Cell Signaling Technology/9188 |
| AKT pan Antibody | Thermo Fisher Scientific/44-609G |
| mTOR Antibody | Thermo Fisher Scientific/PA1-188 |
| IRS1 Antibody | Thermo Fisher Scientific/710009 |
| IRS1 Antibody | Thermo Fisher Scientific/AH01322 |
| IGFIR Antibody | Thermo Fisher Scientific/39-6700 |
| TSC2 Antibody | Thermo Fisher Scientific/AHO1422 |
| TSC2 Antibody | Thermo Fisher Scientific/730014 |
| PTEN Antibody | Thermo Fisher Scientific/51-2400 |

TABLE 2

List of IP to MS less successful antibodies for AKT-mTOR Pathway Proteins

| Antibody Name | Company/Catalog Number |
|---|---|
| Phospho-Akt (Ser473) Antibody | Cell Signaling Technology/4051 |
| AKT1 Antibody | Thermo Fisher Scientific/PA5-23780 |
| AKT2 Antibody | Thermo Fisher Scientific/MA1-034 |
| Phospho-AKT1 pSer473 Antibody | Thermo Fisher Scientific/MA1-20325 |
| Phospho-IGF-I Receptor β (Tyr1316) Antibody | Cell Signaling Technology/6113 |
| Phospho-IGF-I Receptor β (Tyr1131)/Insulin Receptor β (Tyr1146) Antibody | Cell Signaling Technology/3021 |
| IGF-I Receptor β Antibody | Cell Signaling Technology/3018 |
| IGF-IR/IGF1 Receptor alpha Antibody | Thermo Fisher Scientific/MA5-13817 |
| IGF-IR/IGF1 Receptor alpha Antibody | Thermo Fisher Scientific/MA5-13799 |
| Anti-IGF1 Receptor (phospho Y1162 + Y1163) Antibody | Abcam/ab5680 |
| IGF-IR/IGF1 Receptor alpha Antibody | Thermo Fisher Scientific/MA5-13802 |
| IGF-IR/IGF1 Receptor Antibody | Thermo Fisher Scientific/MA1-10853 |
| Phospho-IGF-IR beta pTyr1135/1136 + IR beta pTyr1150/1151 Antibody | Thermo Fisher Scientific/MA5-15148 |
| Phospho-IGF-IR + IR pTyr1162 + 1163 Antibody | Thermo Fisher Scientific/700393 |
| Phospho-IGF-IR pTyr1135 + 1163 Antibody | Thermo Fisher Scientific/701067 |
| Phospho-IGF1 Rec. pTyr1162 + 1163 Antibody | Thermo Fisher Scientific/PA1-26724 |
| Anti-phospho-IR/IGF1R (Tyr1158) Antibody | Millipore/07-839 |
| Insulin Receptor (β-Subunit) | Thermo Fisher Scientific/MS-635-P1 |

TABLE 2-continued

List of IP to MS less successful antibodies for AKT-mTOR Pathway Proteins

| Antibody Name | Company/Catalog Number |
| --- | --- |
| Anti-Insulin Receptor (pTyr1162/1163) Antibody | Millipore/407707 |
| Anti-phospho-IR/IGF1R (Tyr1158/Tyr1162/Tyr1163) Antibody | Millipore/07-841 |
| Phospho-IRS-1 pSer312 Antibody | Thermo Fisher Scientific/PA5-35670 |
| Phospho-IRS-1 (Ser307) Antibody | Cell Signaling Technology/2381 |
| Phospho-IRS-1 (Ser1101) Antibody | Cell Signaling Technology/2385 |
| Phospho-IRS-1 (Ser318) Antibody | Cell Signaling Technology/5610 |
| p70 S6 Kinase Antibody | Cell Signaling Technology/9202 |
| Phospho-p70 S6 Kinase (Thr389) Antibody | Thermo Fisher Scientific/MA5-15117 |
| Phospho-S6 Ribosomal Protein pSer235 + 236 Antibody | Thermo Fisher Scientific/710394 |
| Phospho-p70 S6 Kinase pThr389 Antibody | Thermo Fisher Scientific/710095 |
| p70 S6 Kinase Antibody | Thermo Fisher Scientific/701261 |
| Phospho-p70 S6 Kinase pThr389 Antibody | Thermo Fisher Scientific/PA1-526 |
| GSK-3 alpha Antibody | Novus Biologicals/NB110-87048 |
| GSK3 alpha Antibody | Thermo Fisher Scientific/PA5-15400 |
| GSK3 alpha Antibody | Thermo Fisher Scientific/PA1-25969 |
| GSK3 beta Antibody | Thermo Fisher Scientific/MA1-7621 |
| GSK3B Antibody | Thermo Fisher Scientific/PA1-27893 |
| GSK-3 beta Antibody | Novus Biologicals/NBP1-04292 |
| GSK3B Antibody | Thermo Fisher Scientific/MA5-15597 |
| Anti-Tuberin (phospho S1254) Antibody | Abcam/ab133454 |
| TSC2 (phospho S939) Antibody | Abnova/PAB16959 |
| Phospho-Tuberin/TSC2 (Thr1462) Antibody | Cell Signaling Technology/3611 |
| S6 Ribosomal Protein Antibody | Thermo Fisher Scientific/MA5-15123 |
| Phospho-RSK3 pThr356 + Ser360 Antibody | Thermo Fisher Scientific/PA5-17554 |
| Non-Phospho PTEN (Ser380 + Thr382 + Thr383) Antibody | Thermo Fisher Scientific/PA5-17153 |
| PTEN Antibody | ProSci/3515 |
| PTEN Antibody | ProSci/3517 |

The immunoprecipitated AKT-mTOR pathway proteins may be reduced and alkylated prior to fragmentation (e.g., digestion). Samples that have been reduced and alkylated may comprises modifications, such as to cysteine residues (e.g., CAM). Where an AKT-mTOR peptide of SEQ ID NO: 1-424 shows modification resulting from, for example, reduction/alkylation, the non-modified peptide is also encompassed. For example, in each instance where an AKT-mTOR pathway peptide of SEQ ID NO: 1-424 is referred to, also encompassed are unmodified peptides of SEQ ID NO: 1-424.

The samples may optionally be desalted prior to analysis by mass spectrometry. Both enzymatic and chemical digestion is encompassed. Enzymatic digestion includes, but is not limited to, digestion with a protease such as, for example, trypsin, chymotrypsin, AspN, GluC, LysC, LysN, ArgC, proteinase K, pepsin, Clostripain, Elastase, GluC biocarb, LysC/P, LysN Promise, Protein Endopeptidase, Staph Protease or thermolysin. Chemical digestion includes use of, for example, CNBr, iodosobenzoate and formic acid.

In some embodiments, after fragmentation (e.g., digestion), peptide samples are analyzed by mass spectrometry (MS), and the resulting spectra are compared with theoretical spectra from known proteins to determine the peptides and proteins in a sample. For AKT-mTOR pathway proteins, discovery MS is cumbersome and time consuming and is not a viable clinical method. Therefore, the inventors have identified novel peptides that associate with AKT-mTOR pathway proteins for use in the IP-MS methods of the disclosure. Use of these peptides in targeted MS, and IP-targeted MS methods allows quantitation of even low abundant AKT-mTOR proteins. Moreover, use of these peptides in targeted MS, and in IP-targeted MS methods, allows quantitation of phosphorylated AKT-mTOR proteins.

Theoretically, peptides useful in MS to detect and quantify AKT-mTOR pathway proteins can be designed by use of computer software and the like. However, many of these potential peptide sequences are unsuitable or ineffective for use in MS-based assays, including SRM/MRM and PRM. Because it was not possible to predict the most suitable peptides for MS analysis, it was necessary to experimentally identify modified and unmodified peptides to develop as clinical reagents. To complicate the analysis, it was discovered that certain peptides useful when assaying typical samples were not predictive when assaying samples that had undergone immunoprecipitation.

Typically, targeted MS is performed by quantifying specific unique peptides of the protein. In some embodiments, known amounts of isotope-labeled (e.g., heavy isotope-labeled) versions of these targeted peptides can be used as internal standards for absolute quantitation. In some instances, proteins of interest are not detectable even after identifying unique peptide standards. The combination of specific antibodies with specific target peptides has allowed the inventors to improve the sensitivity of detection of AKT-mTOR pathway proteins by MS, and has allowed for lower levels of detection and lower levels of quantification than ever previously seen. See, e.g., FIG. 4.

In some embodiments, the AKT-mTOR pathway peptides provided in the kits, and useful in the described methods, are listed in Table 3. SEQ ID Nos: 1-212 are native peptide sequences useful in identifying the AKT-mTOR pathway proteins recited in the "Target ID" column. Certain peptide sequences are phosphorylated at certain residues as shown in parentheses "(P03H2)" following the modified residue.

Certain peptides are modified at cysteine residues as shown by "(CAM)" following the modified residue. The "CAM" post-translational modification is well known to those of skill in the art to mean carbamidomethylation, resulting from alkylation of the protein/peptide. The peptides may be as shown in Table 3, or may be non-modified version of these peptides lacking carbamidomethylation.

TABLE 3

List of peptides to quantitate AKT-mTOR Pathway proteins

| Target ID | Native Peptide Sequence | SEQ ID NO: | Internal Standard Peptide Sequence | SEQ ID NO: |
| --- | --- | --- | --- | --- |
| AKT1_1 | NDGTFIGYK | 1 | NDGTFIGY[K(13C6; 15N2)] | 213 |
| AKT1_2 | SLLSGLLK | 2 | SLLSGLL[K(13C6; 15N2)] | 214 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| AKT1_3 | EAPLNNFSVAQCQLMK | 3 | EAPLNNFSVAQCQLM[K(13C6; 15N2)] | 215 |
| AKT1_4 | RPHFPQF[S(PO3H2)]YSASGTA | 4 | RPHFPQF[S(PO3H2)]YSASGT[A(13C3; 15N)] | 216 |
| AKT1_5 | RPHFPQFSYSASGTA | 5 | RPHFPQFSYSASGT[A(13C3; 15N)] | 217 |
| AKT2_1 | SDGSFIGYK | 6 | SDGSFIGY[K(13C6; 15N2)] | 218 |
| AKT2_2 | SLLAGLLK | 7 | SLLAGLL[K(13C6; 15N2)] | 219 |
| AKT2_3 | THFPQF[S(PO3H2)]YSASIRE | 8 | THFPQF[SPO3H2)]YSASI[R(13C6; 15N4)]E | 220 |
| AKT2_4 | THFPQFSYSASIRE | 9 | THFPQFSYSASI[R(13C6; 15N4)]E | 221 |
| AKT3_1 | LVPPFKPQVTSETDTR | 10 | LVPPFKPQVTSETDT[R(13C6; 15N4)] | 222 |
| AKT3_2 | SLLSGLLIK | 11 | SLLSGLLI[K(13C6; 15N2)] | 223 |
| IR_1 | [C(CAM)]SVAAYVSAR | 12 | [C(CAM)]SVAAYVSA[R(13C6; 15N4)] | 224 |
| IR_2 | CSVAAYVSAR | 13 | CSVAAYVSA[R(13C6; 15N4)] | 225 |
| IR_3 | GLKPWTQYAIFVK | 14 | GLKPWTQYAIFV[K(13C6; 15N2)] | 226 |
| IR_4 | IELQA[C(CAM)]NQDTPEER | 15 | IELQA[C(CAM)]NQDTPEE[R(13C6; 15N4)] | 227 |
| IR_5 | TIDSVTSAQELR | 16 | TIDSVTSAQEL[R(13C6; 15N4)] | 228 |
| IR_6 | TNCPATVINGQFVER | 17 | INCPATVINGQFVE[R(13C6; 15N4)] | 229 |
| IR_7 | TN[C(CAM)]PATVINGQFVER | 18 | TN[C(CAM)]PATVINGQFVE[R(13C6; 15N4)] | 230 |
| IR_8 | TNGDQASCENELLK | 19 | INGDQASCENELL[K(13C6; 15N2)] | 231 |
| IR_9 | INGDQAS[C(CAM)]ENELLK | 20 | INGDQAS[C(CAM)]ENELL[K(13C6; 15N2)] | 232 |
| IR_10 | VCHLLEGEK | 21 | VCHLLEGE[K(13C6; 15N2)] | 233 |
| IR_11 | V[C(CAM)]HLLEGEK | 22 | V[C(CAM)]HLLEGE[K(13C6; 15N2)] | 234 |
| IR_12 | TVNESASLR | 23 | TVNESASL[R(13C6; 15N4)] | 235 |
| IR_13 | DIIKGEAETR | 24 | DIIKGEAET[R(13C6; 15N4)] | 236 |
| IR/IGF1R_1 | DIYETDYYR | 25 | DIYETDYY[R(13C6; 15N4)] | 237 |
| IR/IGF1R_2 | DIYETDYYRK | 26 | DIYETDYYR[K(13C6; 15N2)] | 238 |
| IR/IGF1R_3 | DI[Y(PO3H2)]EIDYYR | 27 | DI[Y(PO3H2)]EIDYY[R(13C6; 15N4)] | 239 |
| IR/IGF1R_4 | DIYETD[Y(PO3H2)]YR | 28 | DIYETD[Y(PO3H2)]Y[R(13C6; 15N4)] | 240 |
| IR/IGF1R_5 | DIYETDY[Y(PO3H2)]R | 29 | DIYETDY[Y(PO3H2)][R(13C6; 15N4)] | 241 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| IR/IGF1R_6 | DIYETD[Y(PO3H2)][Y(PO3H2)]R | 30 | DIYETD[Y(PO3H2)][Y(PO3H2)][R(13C6; 15N4)] | 242 |
| IR/IGF1R_7 | DI[Y(PO3H2)]ETD[Y(PO3H2)]YR | 31 | DI[Y(PO3H2)]ETD[Y(PO3H2)]Y[R(13C6; 15N4)] | 243 |
| IR/IGF1R_8 | DI[Y(PO3H2)]EIDY[Y(PO3H2)]R | 32 | DI[Y(PO3H2)]EIDY[Y(PO3H2)][R(13C6; 15N4)] | 244 |
| IR/IGF1R_9 | DI[Y(PO3H2)]ETD[Y(PO3H2)][Y(PO3H2)]R | 33 | DI[Y(PO3H2)]ETD[Y(PO3H2)][Y(PO3H2)][R(13C6; 15N4)] | 245 |
| IGF1R_1 | AENGPGPGVLVLR | 34 | AENGPGPGVLVL[R(13C6; 15N4)] | 246 |
| IGF1R_2 | HYYYAGV[C(CAM)]VPA[C(CAM)]PPNTYR | 35 | HYYYAGV[C(CAM)]VPA[C(CAM)]PPNTY[R(13C6; 15N4)] | 247 |
| IGF1R_3 | HYYYAGVCVPACPPNTYR | 36 | HYYYAGVCVPACPPNTY[R(13C6; 15N4)] | 248 |
| IGF1R_4 | LG[C(CAM)]SASNFVFAR | 37 | LG[C(CAM)]SASNFVFA[R(13C6; 15N4)] | 249 |
| IGF1R_5 | LGCSASNFVFAR | 38 | LGCSASNFVFA[R(13C6; 15N4)] | 250 |
| IGF1R_6 | SLRPEMENNPVLAPPSLSK | 39 | SLRPEMENNPVLAPPSLS[K(13C6; 15N2)] | 251 |
| IGF1R_7 | TTINNEYNYR | 40 | TTINNEYNY[R(13C6; 15N4)] | 252 |
| IGF1R_8 | VAGLESLGDLFPNLTVIR | 41 | VAGLESLGDLFPNLTVI[R(13C6; 15N4)] | 253 |
| IGF1R_9 | YADGTIDIEEVTENPK | 42 | YADGTIDIEEVIENP[K(13C6; 15N2)] | 254 |
| IGF1R_10 | YGSQVEDQRE[C(CAM)]VSR | 43 | YGSQVEDQRE[C(CAM)]VS[R(13C6; 15N4)] | 255 |
| IGF1R_11 | YGSQVEDQRECVSR | 44 | YGSQVEDQRECVS[R(13C6; 15N4)] | 256 |
| IGF1R_12 | IDIHSCNHEAEK | 45 | IDIHSCNHEAE[K(13C6; 15N2)] | 257 |
| IGF1R_13 | GVVKDEPETR | 46 | GVVKDEPET[R(13C6; 15N4)] | 258 |
| IRS1_1 | ASSDGEGTMSRPASVDGSPVSPSTNR | 47 | ASSDGEGTMSRPASVDGSPVSPSTN[R(13C6; 15N4)] | 259 |
| IRS1_2 | [C(CAM)]GHSENFFFIEVGR | 48 | [C(CAM)]GHSENFFFIEVG[R(13C6; 15N4)] | 260 |
| IRS1_3 | CGHSENFFFIEVGR | 49 | CGHSENFFFIEVG[R(13C6; 15N4)] | 261 |
| IRS1_4 | [C(CAM)]TPGTGLGTSPALAGDEAASAADLDNR | 50 | [C(CAM)]TPGTGLGTSPALAGDEAASAADLDN[R(13C6; 15N4)] | 262 |
| IRS1_5 | CTPGTGLGTSPALAGDEAASAADLDNR | 51 | CTPGTGLGTSPALAGDEAASAADLDN[R(13C6; 15N4)] | 263 |
| IRS1_6 | HHLNNPPPSQVGLTR | 52 | HHLNNPPPSQVGLT[R(13C6; 15N4)] | 264 |
| IRS1_7 | HSSETFSSTPSATR | 53 | HSSETFSSTPSAT[R(13C6; 15N4)] | 265 |
| IRS1_8 | KGSGDYMPMSPK | 54 | KGSGDYMPMSP[K(13C6; 15N2)] | 266 |
| IRS1_9 | L[C(CAM)]GAAGGLENGLNYIDLDLVK | 55 | L[C(CAM)]GAAGGLENGLNYIDLDLV[K(13C6; 15N2)] | 267 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| IRS1_10 | LCGAAGGLENGLNYIDLDLVK | 56 | LCGAAGGLENGLNYIDLDLV[K(13C6; 15N2)] | 268 |
| IRS1_11 | SVSAPQQIINPIR | 57 | SVSAPQQIINPI[R(13C6; 15N4)] | 269 |
| IRS1_12 | TESITATSPASMVGGKPGSFR | 58 | TESITATSPASMVGGKPGSF[R(13C6; 15N4)] | 270 |
| IRS1_13 | TGIAAEEVSLPR | 59 | TGIAAEEVSLP[R(13C6; 15N4)] | 271 |
| IRS1_14 | SYPEEGLEMHPLER | 60 | SYPEEGLEMHPLE[R(13C6; 15N4)] | 272 |
| IRS1_15 | THSAGTSPTITHQK | 61 | THSAGTSPTITHQ[K(13C6; 15N2)] | 273 |
| IRS1_16 | AS[S(PO3H2)]DGEGTMSRPASVDGSPVSPSTNR | 62 | AS[S(PO3H2)]DGEGTMSRPASVDGSPVSPSTN[R(13C6; 15N4)] | 274 |
| IRS1_17 | HS[S(PO3H2)]ETFSSTPSATR | 63 | HS[S(PO3H2)]ETFSSTPSAT[R(13C6; 15N4)] | 275 |
| IRS1_18 | KGSGDYMPM[S(PO3H2)]PK | 64 | KGSGDYMPM[S(PO3H2)]P[K(13C6; 15N2)] | 276 |
| IRS1_19 | KGSGDY[M(O)]P[M(O)][S(PO3H2)]PK | 65 | KGSGDY[M(O)]P[M(O)][S(PO3H2)]P[K(13C6; 15N2)] | 277 |
| IRS1_20 | L[C(CAM)]GAAGGLENGLN[Y(PO3H2)]IDLDLVK | 66 | L[C(CAM)]GAAGGLENGLN[Y(PO3H2)]IDLDLV[K(13C6; 15N2)] | 278 |
| IRS1_21 | LCGAAGGLENGLN[Y(PO3H2)]IDLDLVK | 67 | LCGAAGGLENGLN[Y(PO3H2)]IDLDLV[K(13C6; 15N2)] | 279 |
| IRS1_22 | TESITAT[S(PO3H2)]PASMVGGKPGSFR | 68 | TESITAT[S(PO3H2)]PASMVGGKPGSF[R(13C6; 15N4)] | 280 |
| IRS1_23 | TESITAT[S(PO3H2)]PAS[M(O)]VGGKPGSFR | 69 | TESITAT[S(PO3H2)]PAS[M(O)]VGGKPGSF[R(13C6; 15N4)] | 281 |
| TSC2_1 | APAQTPAEPTPGYEVGQR | 70 | APAQTPAEPTPGYEVGQ[R(13C6; 15N4)] | 282 |
| TSC2_2 | DSFRARSTSLNERPK | 71 | DSFRARSTSLNERP[K(13C6; 15N2)] | 283 |
| TSC2_3 | EAPAKLESQAGQQVSR | 72 | EAPAKLESQAGQQVS[R(13C6; 15N4)] | 284 |
| TSC2_4 | GYTISDSAPSR | 73 | GYTISDSAPS[R(13C6; 15N4)] | 285 |
| TSC2_5 | LISSVEDFTEFV | 74 | LISSVEDFTEF[V(13C5; 15N)] | 286 |
| TSC2_6 | LVTVTTSVGTGTR | 75 | LVTVTTSVGTGT[R(13C6; 15N4)] | 287 |
| TSC2_7 | SQSGTLDGESAAWSASGEDSR | 76 | SQSGTLDGESAAWSASGEDS[R(13C6; 15N4)] | 288 |
| TSC2_8 | SVQLLDQIPSYDTHK | 77 | SVQLLDQIPSYDTH[K(13C6; 15N2)] | 289 |
| TSC2_9 | VGALDVPASQFLGSATSPGPR | 78 | VGALDVPASQFLGSATSPGP[R(13C6; 15N4)] | 290 |
| TSC2_10 | VVSSEGGRPSVDLSFQPSQPLSK | 79 | VVSSEGGRPSVDLSFQPSQPLS[K(13C6; 15N2)] | 291 |
| TSC2_11 | YTEFLTGLGR | 80 | YTEFLTGLG[R(13C6; 15N4)] | 292 |
| 2SC2_12 | YVFSNFTAVPK | 81 | YVFSNFTAVP[K(13C6; 15N2)] | 293 |
| TSC2_13 | SNPTDIYPSK | 82 | SNPTDIYPS[K(13C6; 15N2)] | 294 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| TSC2_14 | FNSCYLDEYIAR | 83 | FNSCYLDEYIA[R(13C6; 15N4)] | 295 |
| TSC2_15 | GQPEGPLPSSSPR | 84 | GQPEGPLPSSSP[R(13C6; 15N4)] | 296 |
| TSC2_16 | SLLGLDSGELQSGPESSSSPGVHVR | 85 | SLLGLDSGELQSGPESSSSPGVHV[R(13C6; 15N4)] | 297 |
| TSC2_17 | DSFRARST[S(PO3H2)]LNERPK | 86 | DSFRARST[S(PO3H2)]LNERP[K(13C6; 15N2)] | 298 |
| TSC2_18 | GY[T(PO3H2)]ISDSAPSR | 87 | GY[T(PO3H2)]ISDSAPS[R(13C6; 15N4)] | 299 |
| TSC2_19 | LI[S(PO3H2)]SVEDFTEFV | 88 | LI[S(PO3H2)]SVEDFTEF[V(13C5; 15N)] | 300 |
| TSC2_20 | LIS[S(PO3H2)]VEDFTEFV | 89 | LIS[S(PO3H2)]VEDFTEF[V(13C5; 15N)] | 301 |
| TSC2_21 | LI[S(PO3H2)][S(PO3H2)]VEDFTEFV | 90 | LI[S(PO3H2)][S(PO3H2)]VEDFTEF[V(13C5; 15N)] | 302 |
| TSC2_22 | ST[S(PO3H2)]LNERPK | 91 | ST[S(PO3H2)]LNERP[K(13C6; 15N2)] | 303 |
| TSC2_23 | STSLNERPK | 92 | STSLNERP[K(13C6; 15N2)] | 304 |
| mTOR_1 | AVLALHQDLFSLAQQ[C(CAM)]IDK | 93 | AVLALHQDLFSLAQQ[C(CAM)]ID[K(13C6; 15N2)] | 305 |
| mTOR_2 | AVLALHQDLFSLAQQCIDK | 94 | AVLALHQDLFSLAQQCID[K(13C6; 15N2)] | 306 |
| mTOR_3 | DLELAVPGTYDPNQPIIR | 95 | DLELAVPGTYDPNQPII[R(13C6; 15N4)] | 307 |
| mTOR_4 | GNNLQDTLR | 96 | GNNLQDTL[R(13C6; 15N4)] | 308 |
| mTOR_5 | GPTPAILESLISINNK | 97 | GPTPAILESLISINN[K(13C6; 15N2)] | 309 |
| mTOR_6 | GYTLADEEEDPLIYQHR | 98 | GYTLADEEEDPLIYQH[R(13C6; 15N4)] | 310 |
| mTOR_7 | IHGALLILNELVR | 99 | IHGALLILNELV[R(13C6; 15N4)] | 311 |
| mTOR_8 | IQSIAPSLQVITSK | 100 | IQSIAPSLQVITS[K(13C6; 15N2)] | 312 |
| mTOR_9 | LFDAPEAPLPSR | 101 | LFDAPEAPLPS[R(13C6; 15N4)] | 313 |
| mTOR_10 | LGEWQLNLQGINESTIPK | 102 | LGEWQLNLQGINESTIP[K(13C6; 15N2)] | 314 |
| mTOR_11 | LIHQLLTDIGR | 103 | LIHQLLTDIG[R(13C6; 15N4)] | 315 |
| mTOR_12 | SPSSEVWFDR | 104 | SPSSEVWFD[R(13C6; 15N4)] | 316 |
| mTOR_13 | TDSYSAGQSVEILDGVELGEPAHK | 105 | TDSYSAGQSVEILDGVELGEPAH[K(13C6; 15N2)] | 317 |
| mTOR_14 | TLVLLLGVDPSR | 106 | TLVLLLGVDPS[R(13C6; 15N4)] | 318 |
| mTOR_15 | VEVFEHAVNNTAGDDLAK | 107 | VEVFEHAVNNTAGDDLA[K(13C6; 15N2)] | 319 |
| mTOR_16 | VLGLLGALDPYK | 108 | VLGLLGALDPY[K(13C6; 15N2)] | 320 |
| mTOR_17 | WTLVNDETQAK | 109 | WTLVNDETQA[K(13C6; 15N2)] | 321 |
| mTOR_18 | ETSFNQAYGR | 110 | ETSFNQAYG[R(13C6; 15N4)] | 322 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| mTOR_19 | TLDQSPELR | 111 | TLDQSPEL[R(13C6; 15N4)] | 323 |
| mTOR_20 | TD[S(PO3H2)]YSAGQSVEILDGVELGEPAHK | 112 | TD[S(PO3H2)]YSAGQSVEILDGVELGEPAH[K(13C6; 15N2)] | 324 |
| mTOR_21 | [T(PO3H2)]DSYSAGQSVEILDGVELGEPAHK | 113 | [T(PO3H2)]DSYSAGQSVEILDGVELGEPAH[K(13C6; 15N2)] | 325 |
| mTOR_22 | [T(PO3H2)]D[S(PO3H2)]YSAGQSVEILDGVELGEPAHK | 114 | [T(PO3H2)]D[S(PO3H2)]YSAGQSVEILDGVELGEPAH[K(13C6; 15N2)] | 326 |
| GSK3a_1 | DIKPQNLLVDPDTAVLK | 115 | DIKPQNLLVDPDTAVL[K(13C6; 15N2)] | 327 |
| GSK3a_2 | LSPLEA[C(CAM)]AHSFFDELR | 116 | LSPLEA[C(CAM)]AHSFFDEL[R(13C6; 15N4)] | 328 |
| GSK3a_3 | LSPLEACAHSFFDELR | 117 | LSPLEACAHSFFDEL[R(13C6; 15N4)] | 329 |
| GSK3a_4 | SLAYIHSQGV[C(CAM)]HR | 118 | SLAYIHSQGV[C(CAM)]H[R(13C6; 15N4)] | 330 |
| GSK3a_5 | SLAYIHSQGVCHR | 119 | SLAYIHSQGVCH[R(13C6; 15N4)] | 331 |
| GSK3a_6 | SQEVAYTDIK | 120 | SQEVAYTDI[K(13C6; 15N2)] | 332 |
| GSK3a_7 | TPPEAIAL[C(CAM)]SSLLEYTPSSR | 121 | TPPEAIAL[C(CAM)]SSLLEYTPSS[R(13C6; 15N4)] | 333 |
| GSK3a_8 | TPPEAIALCSSLLEYTPSSR | 122 | TPPEAIALCSSLLEYTPSS[R(13C6; 15N4)] | 334 |
| GSK3a_9 | TSSFAEPGGGGGGGGGPGGSASGPGGTGGGK | 123 | TSSFAEPGGGGGGGGGPGGSASGPGGTGGG[K(13C6; 15N2)] | 335 |
| GSK3a_10 | VTTVVATLGQGPER | 124 | VTTVVATLGQGPE[R(13C6; 15N4)] | 336 |
| GSK3a_11 | DSGKVTTVVATLGQGPER | 125 | DSGKVTTVVATLGQGPE[R(13C6; 15N4)] | 337 |
| GSK3a_12 | YFFYSSGEK | 126 | YFFYSSGE[K(13C6; 15N2)] | 338 |
| GSK3a_13 | TS[S(PO3H2)]FAEPGGGGGGGGGGPGGSASGPGGTGGGK | 127 | TS[S(PO3H2)]FAEPGGGGGGGGGPGGSASGPGGTGGG[K(13C6; 15N2)] | 339 |
| GSK3b_1 | DEVYLNLVLDYVPETVYR | 128 | DEVYLNLVLDYVPETVY[R(13C6; 15N4)] | 340 |
| GSK3b_2 | DIKPQNLLLDPDTAVLK | 129 | DIKPQNLLLDPDTAVL[K(13C6; 15N2)] | 341 |
| GSK3b_3 | DTPALFNFTTQELSSNPPLATILIPPHAR | 130 | DTPALFNFTTQELSSNPPLATILIPPHA[R(13C6; 15N4)] | 342 |
| GSK3b_4 | L[C(CAM)]DSGELVAIK | 131 | L[C(CAM)]DSGELVAI[K(13C6; 15N2)] | 343 |
| GSK3b_5 | LCDSGELVAIK | 132 | LCDSGELVAI[K(13C6; 15N2)] | 344 |
| GSK3b_6 | LLEYTPTAR | 133 | LLEYTPTA[R(13C6; 15N4)] | 345 |
| GSK3b_7 | SLAYIHSFGI[C(CAM)]HR | 134 | SLAYIHSFGI[C(CAM)]H[R(13C6; 15N4)] | 346 |
| GSK3b_8 | SLAYIHSFGICHR | 135 | SLAYIHSFGICH[R(13C6; 15N4)] | 347 |
| GSK3b_9 | TTSFAES[C(CAM)]KPVQQPSAFGSMK | 136 | TTSFAES[C(CAM)]KPVQQPSAFGSM[K(13C6; 15N2)] | 348 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| GSK3b_10 | TTSFAESCKPVQQPSAFGSMK | 137 | TTSFAESCKPVQQPSAFGSM[K(13C6; 15N2)] | 349 |
| GSK3b_11 | TTSFAES[C(CAM)]KPVQQPSAFGS[M(O)]K | 138 | TTSFAES[C(CAM)]KPVQQPSAFGS[M(O)][K(13C6; 15N2)] | 350 |
| GSK3b_12 | TTSFAESCKPVQQPSAFGS[M(O)]K | 139 | TTSFAESCKPVQQPSAFGS[M(O)][K(13C6; 15N2)] | 351 |
| GSK3b_13 | VTTVVATPGQGPDRPQEVSYTDTK | 140 | VTTVVATPGQGPDRPQEVSYTDTK | 352 |
| GSK3b_14 | KLDHCNIVR | 141 | KLDHCNIV[R(13C6; 15N4)] | 353 |
| GSK3b_15 | DSSGTGHFTSGVR | 142 | DSSGTGHFTSGV[R(13C6; 15N4)] | 354 |
| GSK3b_16 | TT[S(PO3H2)]FAES[C(CAM)]KPVQQPSAFGS[M(O)]K | 143 | TT[S(PO3H2)]FAES[C(CAM)]KPVQQPSAFGS[M(O)][K(13C6; 15N2)] | 355 |
| GSK3b_17 | TT[S(PO3H2)]FAESCKPVQQPSAFGS[M(O)]K | 144 | TT[S(PO3H2)]FAESCKPVQQPSAFGS[M(O)][K(13C6; 15N2)] | 356 |
| GSK3b_18 | TT[S(PO3H2)]FAES[C(CAM)]KPVQQPSAFGSMK | 145 | TT[S(PO3H2)]FAES[C(CAM)]KPVQQPSAFGSM[K(13C6; 15N2)] | 357 |
| GSK3b_19 | TT[S(PO3H2)]FAESCKPVQQPSAFGSMK | 146 | TT[S(PO3H2)]FAESCKPVQQPSAFGSM[K(13C6; 15N2)] | 358 |
| GSK3a/GSK3b_1 | GEPNVSYI[C(CAM)]SR | 147 | GEPNVSYI[C(CAM)]S[R(13C6; 15N4)] | 359 |
| GSK3a/GSK3b_2 | GEPNVSYICSR | 148 | GEPNVSYICS[R(13C6; 15N4)] | 360 |
| GSK3a/GSK3b_3 | GEPNVS[Y(PO3H2)]I[C(CAM)]SR | 149 | GEPNVS[Y(PO3H2)]I[C(CAM)]S[R(13C6; 15N4)] | 361 |
| GSK3a/GSK3b_4 | GEPNVS[Y(PO3H2)]ICSR | 150 | GEPNVS[Y(PO3H2)]ICS[R(13C6; 15N4)] | 362 |
| GSK3a/GSK3b_5 | GEPNV[S(PO3H2)]YI[C(CAM)]SR | 151 | GEPNV[S(PO3H2)]YI[C(CAM)]S[R(13C6; 15N4)] | 363 |
| GSK3a/GSK3b_6 | GEPNV[S(PO3H2)]YICSR | 152 | GEPNV[S(PO3H2)]YICS[R(13C6; 15N4)] | 364 |
| GSK3a/GSK3b_7 | GEPNV[S(PO3H2)][Y(PO3H2)]I[C(CAM)]SR | 153 | GEPNV[S(PO3H2)][Y(PO3H2)]I[C(CAM)]S[R(13C6; 15N4)] | 365 |
| GSK3a/GSK3b_8 | GEPNV[S(PO3H2)][Y(PO3H2)]ICSR | 154 | GEPNV[S(PO3H2)][Y(PO3H2)]ICS[R(13C6; 15N4)] | 366 |
| GSK3a/GSK3b_9 | TPPEAIALCSR | 155 | TPPEAIALCS[R(13C6; 15N4)] | 367 |
| GSK3a/GSK3b_10 | TPPEAIAL[C(CAM)]SR | 156 | TPPEAIAL[C(CAM)]S[R(13C6; 15N4)] | 368 |
| p70S6K_1 | DGFYPAPDFR | 157 | DGFYPAPDF[R(13C6; 15N4)] | 369 |
| p70S6K_2 | DLKPENIMLNHQGHVK | 158 | DLKPENIMLNHQGHV[K(13C6; 15N2)] | 370 |
| p70S6K_3 | FEISETSVNR | 159 | FEISETSVN[R(13C6; 15N4)] | 371 |
| p70S6K_4 | FSPGDFWGR | 160 | FSPGDFWG[R(13C6; 15N4)] | 372 |
| p70S6K_5 | HINWEELLAR | 161 | HINWEELLA[R(13C6; 15N4)] | 373 |
| p70S6K_6 | HPFIVDLIYAFQTGGK | 162 | HPFIVDLIYAFQTGG[K(13C6; 15N2)] | 374 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| p70S6K_7 | IRPE[C(CAM)]FELLR | 163 | IRPE[C(CAM)]FELL[R(13C6; 15N4)] | 375 |
| p70S6K_8 | IRPECFELLR | 164 | IRPECFELL[R(13C6; 15N4)] | 376 |
| p70S6K_9 | LGAGPGDAGEVQAHPFFR | 165 | LGAGPGDAGEVQAHPFF[R(13C6; 15N4)] | 377 |
| p70S6K_10 | LNLPPYLTQEAR | 166 | LNLPPYLTQEA[R(13C6; 15N4)] | 378 |
| p70S6K_11 | LTDFGL[C(CAM)]K | 167 | LTDFGL[C(CAM)][K(13C6; 15N2)] | 379 |
| p70S6K_12 | LTDFGLCK | 168 | LTDFGLC[K(13C6; 15N2)] | 380 |
| p70S6K_13 | QTPVDSPDDSTLSESANQVFLGFTYVAPSVLESVK | 169 | QTPVDSPDDSTLSESANQVFLGFTYVAPSVLESV[K(13C6; 15N2)] | 381 |
| p70S6K_14 | TPVSPVK | 170 | TPVSPV[K(13C6; 15N2)] | 382 |
| p70S6K_15 | TPVSPVKFSPGDFWGR | 171 | TPVSPVKFSPGDFWG[R(13C6; 15N4)] | 383 |
| p70S6K_16 | QTPVDSPDDSTLSESANQVFLGF[T(PO3H2)]YVAPSVLESVK | 172 | QTPVDSPDDSTLSESANQVFLGF[T(PO3H2)]YVAPSVLESV[K(13C6; 15N2)] | 384 |
| p70S6K_17 | QTPVD[S(PO3H2)]PDDSTLSESANQVFLGFTYVAPSVLESVK | 173 | QTPVD[S(PO3H2)]PDDSTLSESANQVFLGFTYVAPSVLESV[K(13C6; 15N2)] | 385 |
| p70S6K_18 | QTPVD[S(PO3H2)]PDDSTLSESANQVFLGF[T(PO3H2)]YVAPSVLESVK | 174 | QTPVD[S(PO3H2)]PDDSTLSESANQVFLGF[T(PO3H2)]YVAPSVLESV[K(13C6; 15N2)] | 386 |
| p70S6K_19 | [T(PO3H2)]PVSPVK | 175 | [T(PO3H2)]PVSPV[K(13C6; 15N2)] | 387 |
| p70S6K_20 | TPV[S(PO3H2)]PVK | 176 | TPV[S(PO3H2)]PV[K(13C6; 15N2)] | 388 |
| p70S6K_21 | [T(PO3H2)]PV[S(PO3H2)]PVK | 177 | [T(PO3H2)]PV[S(PO3H2)]PV[K(13C6; 15N2)] | 389 |
| p70S6K_22 | TPV[S(PO3H2)]PVKFSPGDFWGR | 178 | TPV[S(PO3H2)]PVKFSPGDFWG[R(13C6; 15N4)] | 390 |
| p70S6K_23 | [T(PO3H2)]PV[S(PO3H2)]PVKFSPGDFWGR | 179 | [T(PO3H2)]PV[S(PO3H2)]PVKFSPGDFWG[R(13C6; 15N4)] | 391 |
| p70S6K_24 | [T(PO3H2)]PVSPVKFSPGDFWGR | 180 | [T(PO3H2)]PVSPVKFSPGDFWG[R(13C6; 15N4)] | 392 |
| RPS6_1 | DIPGLTDTTVPR | 181 | DIPGLTDTTVP[R(13C6; 15N4)] | 393 |
| RPS6_2 | GHS[C(CAM)]YRPR | 182 | GHS[C(CAM)]YRP[R(13C6; 15N4)] | 394 |
| RPS6_3 | GHSCYRPR | 183 | GHSCYRP[R(13C6; 15N4)] | 395 |
| RPS6_4 | LNISFPATG[C(CAM)]QK | 184 | LNISFPATG[C(CAM)]Q[K(13C6; 15N2)] | 396 |
| RPS6_5 | LNISFPATGCQK | 185 | LNISFPATGCQ[K(13C6; 15N2)] | 397 |
| RPS6_6 | MATEVAADALGEEWK | 186 | MATEVAADALGEEW[K(13C6; 15N2)] | 398 |
| RPS6_7 | RRRLSSLRASTSK | 187 | RRRLSSLRASTS[K(13C6; 15N2)] | 399 |
| RPS6_8 | RRRL[S(PO3H2)]SLRASTSK | 188 | RRRL[S(PO3H2)]SLRASTS[K(13C6; 15N2)] | 400 |
| RPS6_9 | RRRLS[S(PO3H2)]LRASTSK | 189 | RRRLS[S(PO3H2)]LRASTS[K(13C6; 15N2)] | 401 |

TABLE 3-continued

List of peptides to quantitate AKT-mTOR Pathway proteins

| Target ID | Native Peptide Sequence | SEQ ID NO: | Internal Standard Peptide Sequence | SEQ ID NO: |
|---|---|---|---|---|
| RPS6_10 | RRRL[S(PO3H2)][S(PO3H2)]LRASTSK | 190 | RRRL[S(PO3H2)][S(PO3H2)]LRASTS[K(13C6; 15N2)] | 402 |
| PRAS40_1 | AATAARPPAPPPAPQPPSPTPSPPRPTLAR | 191 | AATAARPPAPPPAPQPPSPTPSPPRPTLA[R(13C6; 15N4)] | 403 |
| PRAS40_2 | [C(CAM)]LHDIALAHR | 192 | [C(CAM)]LHDIALAH[R(13C6; 15N4)] | 404 |
| PRAS40_3 | CLHDIALAHR | 193 | CLHDIALAH[R(13C6; 15N4)] | 405 |
| PRAS40_4 | EAEDTQVFGDLPRPR | 194 | EAEDTQVFGDLPRP[R(13C6; 15N4)] | 406 |
| PRAS40_5 | SLPVSVPVWGFK | 195 | SLPVSVPVWGF[K(13C6; 15N2)] | 407 |
| PRAS40_6 | SSDEENGPPSSPDLDR | 196 | SSDEENGPPSSPDLD[R(13C6; 15N4)] | 408 |
| PRAS40_7 | TEARSSDEENGPPSSPDLDR | 197 | TEARSSDEENGPPSSPDLDR(13C6; 15N4)] | 409 |
| PRAS40_8 | TGTELVLLTAAPPPPRPGP[C(CAM)]AYAAHGR | 198 | TGTELVLLTAAPPPPRPGP[C(CAM)]AYAAHG[R(13C6; 15N4)] | 410 |
| PRAS40_9 | TGTELVLLTAAPPPPRPGPCAYAAHGR | 199 | TGTELVLLTAAPPPPRPGPCAYAAHG[R(13C6; 15N4)] | 411 |
| PRAS40_10 | LNTSDFQK | 200 | LNTSDFQ[K(13C6; 15N2)] | 412 |
| PRAS40_11 | EAEDTQVFGDLPRPRLNTSDFQK | 201 | EAEDTQVFGDLPRPRLNTSDFQ[K(13C6; 15N2)] | 413 |
| PRAS40_12 | GALAEAAR | 202 | GALAEAA[R(13C6; 15N4)] | 414 |
| PRAS40_13 | ASGRPEELWEAVVGAAER | 203 | ASGRPEELWEAVVGAAE[R(13C6; 15N4)] | 415 |
| PRAS40_14 | LN[T(PO3H2)]SDFQK | 204 | LN[T(PO3H2)]SDFQ[K(13C6; 15N2)] | 416 |
| PRAS40_15 | EAEDTQVFGDLPRPRLN[T(PO3H2)]SDFQK | 205 | EAEDTQVFGDLPRPRLN[T(PO3H2)]SDFQ[K(13C6; 15N2)] | 417 |
| PTEN_1 | YSDTTDSDPENEPFDEDQHTQITK | 206 | YSDTTDSDPENEPFDEDQHTQIT[K(13C6; 15N2)] | 418 |
| PTEN_2 | YSDTTDSDPENEPFDEDQHTQITKV | 207 | YSDTTDSDPENEPFDEDQHTQIT[K(13C6; 15N2)]V | 419 |
| PTEN_3 | NNIDDVVR | 208 | NNIDDVV[R(13C6; 15N4)] | 420 |
| PTEN_4 | AQEALDFYGEVR | 209 | AQEALDFYGEV[R(13C6; 15N4)] | 421 |
| PTEN_5 | IYSSNSGPTR | 210 | IYSSNSGPT[R(13C6; 15N4)] | 422 |
| PTEN_6 | Y[S(PO3H2)]DTTDSDPENEPFDEDQHTQITK | 211 | Y[S(PO3H2)]DTTDSDPENEPFDEDQHTQIT[K(13C6; 15N2)] | 423 |
| PTEN_7 | Y[S(PO3H2)]DTTDSDPENEPFDEDQHTQITKV | 212 | Y[S(PO3H2)]DTTDSDPENEPFDEDQHTQIT[K(13C6; 15N2)]V | 424 |

In some embodiments, the peptides reagents are recited in Table 5 (SEQ ID Nos: 98, 96, 157, 163, 40, 42, 37, 25, 73, 80, 52, 57, 59, 208, 209, 16, 23, 124, 120, 195, 200, 129, 133, 1, 6, 27, 91, and 204). In some embodiments, the peptides of Table 5 are useful in multi-plex MS methods.

In some embodiments, protein samples are denatured or solubilized before fragmentation.

In some embodiments, the fragmentation protocol uses chemical cleavage. In some embodiments, the chemical cleavage uses CNBr. In some embodiments, the fragmentation protocol is done using an enzyme. In some embodiments, the fragmentation protocol uses MS-grade commercially available proteases. Examples of proteases that may be used to digest samples include trypsin, endoproteinase GluC, endoproteinase ArgC, pepsin, chymotrypsin, LysN protease, LysC protease, GluC protease, AspN protease, proteinase K, and thermolysin. In some embodiments, a mixture of different proteases are used and the individual results are combined together after the digestion and analysis. In some embodiments, the digestion is incomplete in order to see larger, overlapping peptides. In some embodiments, the antibody digestion is performed with IdeS, IdeZ, pepsin, or papain to generate large antibody domains for "middle-down" protein characterization. In some embodiments, the fragmentation protocol uses trypsin that is modified. In some embodiments, a protein:protease ratio (w/w) of 10:1, 20:1, 25:1, 50:1, 66:1, or 100:1 may be used. In some embodiments, the trypsin used is at a concentration of about 100 ng/ml-1 mg/ml, or about 100 ng/ml-500 µg/ml, or about 100 ng/ml-100 µg/ml, or about 1 µg/ml-1 mg/ml, or about 1 µg/ml-500 µg/ml, or about 1 µg/ml-100 µg/ml, or about 10 µg/mg-1 mg/ml, or about 10 µg/mg-500 µg/ml, or about 10 µg/mg-100 µg/ml. In some embodiments, the digestion step is for 10 minutes to 48 hours, or 30 minutes to 48 hours, or 30 minutes to 24 hours, or 30 minutes to 16 hours, or 1 hour to 48 hours, or 1 hour to 24 hours, or 1 hour to 16 hours, or 1 to 8 hours, or 1 to 6 hours, or 1 to 4 hours. In some embodiments, the digestion step is incubated at a temperature between 20° C. and 45° C., or between 20° C. and 40° C., or between 22° C. and 40° C., or between 25° C. and 37° C. In some embodiments, the digestion step is incubated at 37° C. or 30° C. In some embodiments, a step is included to end the digestion step. The step to end the digestion protocol may be addition of a stop solution or a step of spinning or pelleting of a sample. In some embodiments, the digestion is followed by guanidation.

In some embodiments, the fragmentation protocol includes use of protein gels. In some embodiments, the fragmentation protocol comprises in-gel digestion. An exemplary commercially available kit for performing in-gel digestion is the In-Gel Tryptic Digestion Kit (Thermo Fisher Cat#89871).

In some embodiments, the fragmentation protocol is carried out in solution. An exemplary commercially available kit for performing in-solution digestion is the In-Solution Tryptic Digestion and Guanidiation Kit (Thermo Fisher Cat#89895).

In some embodiments, the fragmentation protocol uses beads. In some embodiments, the fragmentation protocol comprises on-bead digestion. In some embodiments, agarose beads or Protein G beads are used. In some embodiments, magnetic beads are used.

In some embodiments, protein samples are separated using liquid chromatography before MS analysis. In some embodiments, fragmented samples are separated using liquid chromatography before MS analysis.

The IP and IP-MS methods described herein are capable of detecting phosphorylated AKT-mTOR pathway proteins, including those described in Table 4.

TABLE 4

List of Total and Phosphorylated AKT-mTOR Pathway Target Proteins

| Target ID No. | Target Name (Total) | Phosphorylation Site |
|---|---|---|
| 1 | AKT1 | pSer473 |
| 2 | PTEN | pSer380 |
| 3 | IRS1 | pSer312 |
| 4 | IR | pTyr1162/1163 |
| 5 | IGF-1R | pTyr1135/1136 |

TABLE 4-continued

List of Total and Phosphorylated AKT-mTOR Pathway Target Proteins

| Target ID No. | Target Name (Total) | Phosphorylation Site |
|---|---|---|
| 6 | GSK3a | pSer21 |
| 7 | GSK3b | pSer9 |
| 8 | RPS6 | pSer235/236 |
| 9 | PRAS40 | pThr246 |
| 10 | mTOR | pSer2448 |
| 11 | p70S6K (S6K1) | pThr389 |
| 12 | TSC2 | pSer939 |

In some embodiments, the AKT-mTOR pathway peptides used in the MS methods described herein have limits of detection considered useful in clinical and research methods. See, e.g, Table 5. In some embodiments, the AKT-mTOR pathway peptides used in the MS and IP-MS methods comprise or consist of the peptides described in Table 5. In some embodiments, the peptides of Table 5 are detectably labelled. The peptides of SEQ ID NO: 163 may lack the "CAM" modification shown on the fifth amino acid.

TABLE 5

Lower Limit of Quantitation of Peptides for AKT-mTOR Pathway Proteins

| Target ID | Native Peptide Sequence | SEQ ID NO: | Lower limit of Quantitation (fmol) |
|---|---|---|---|
| mTOR_6 | GYTLADEEEDPLIYQHR | 98 | 0.69 |
| mTOR_4 | GNNLQDTLR | 96 | 0.08 |
| p70S6K_1 | DGFYPAPDFR | 157 | 0.23 |
| p70S6K_7 | IRPE[C(CAM)]FELLR | 163 | 6.17 |
| IGF1R_7 | TTINNEYNYR | 40 | 0.08 |
| IGF1R_9 | YADGTIDIEEVTENPK | 42 | 0.69 |
| IGF1R_4 | LG[C(CAM)]SASNFVFAR | 37 | 2.06 |
| IR/IGF1R_1 | DIYETDYYR | 25 | 0.69 |
| TSC2_4 | GYTISDSAPSR | 73 | 0.69 |
| TSC2_11 | YTEFLTGLGR | 80 | 0.69 |
| IRS1_6 | HHLNNPPPSQVGLTR | 52 | 0.69 |
| IRS1_11 | SVSAPQQIINPIR | 57 | 0.08 |
| IRS1_13 | TGIAAEEVSLPR | 59 | 0.23 |
| PTEN_3 | NNIDDVVR | 208 | 0.08 |
| PTEN_4 | AQEALDFYGEVR | 209 | 0.08 |
| IR_5 | TIDSVTSAQELR | 16 | 0.23 |
| IR_12 | TVNESASLR | 23 | 0.08 |
| GSK3a_10 | VTTVVATLGQGPER | 124 | 0.23 |
| GSK3a_6 | SQEVAYTDIK | 120 | 0.69 |
| PRAS40_5 | SLPVSVPVWGFK | 195 | 6.17 |
| PRAS40_10 | LNTSDFQK | 200 | 0.69 |
| GSK3b_2 | DIKPQNLLLDPDTAVLK | 129 | 6.17 |

TABLE 5-continued

Lower Limit of Quantitation of Peptides for AKT-mTOR Pathway Proteins

| Target ID | Native Peptide Sequence | SEQ ID NO: | Lower limit of Quantitation (fmol) |
|---|---|---|---|
| GSK3b_6 | LLEYTPTAR | 133 | 0.23 |
| AKT1_1 | NDGTFIGYK | 1 | 0.23 |
| AKT2_1 | SDGSFIGYK | 6 | 0.69 |
| IR/IGF1R_3 | DI[Y(PO3H2)]ETDYYR | 27 | 0.69 |
| TSC2_22 | ST[S(PO3H2)]LNERPK | 91 | 0.23 |
| PRAS40_14 | LN[T(PO3H2)]SDFQK | 204 | 0.69 |

In some embodiments, methods for detecting phosphorylated AKT-mTOR pathway proteins are encompassed. In some embodiments, IP, MS, and IP-MS methods to detect phosphorylated AKT-mTOR pathway proteins are conducted separately from methods to detect total (non-phosphorylated) AKT-mTOR pathway proteins. In some embodiments, the IP and IP-MS methods to detect phosphorylated AKT-mTOR pathway proteins utilize the antibodies of Table 9. In some embodiments, the IP and IP-MS methods to detect non-phosphorylated AKT-mTOR pathway proteins utilize the antibodies of Table 8. In some embodiments, the IP-MS methods to detect phosphorylated AKT-mTOR pathway proteins utilize the antibodies of Table 9 and the peptides of Table 5. In some embodiments, the IP-MS methods to detect non-phosphorylated AKT-mTOR pathway proteins utilize the antibodies of Table 8 and the peptides of Table 5.

TABLE 8

List of non-phospho-antibodies for multi-plex IP, single-plex IP (+/− MS).

| Target | Vendor | IP Antibody |
|---|---|---|
| AKT | MILLIPORE | 07-416 |
| IGF1R | CELL SIGNALING TECHNOLOGY | 3027 |
| IR | MILLIPORE | 07-724 |
| IRS1 | CELL SIGNALING TECHNOLOGY | 2382 |
| mTOR | THERMO FISHER SCIENTIFIC | PA1-518 |
| P70S6K | ABGENT | AP3289g |
| GSK3a | CELL SIGNALING TECHNOLOGY | 4337 |
| GSK3b | THERMO FISHER SCIENTIFIC | MA5-15109 |
| TSC2 | THERMO FISHER SCIENTIFIC | MA5-15004 |
| PRAS40 | THERMO FISHER SCIENTIFIC | PA5-35143 |
| PTEN | CELL SIGNALING TECHNOLOGY | 9188 |

TABLE 9

List of antibodies for multi-plex IP, single-plex IP (+/− MS).

| Target | Vendor | IP Antibody |
|---|---|---|
| phosphoAKT | CELL SIGNALING TECHNOLOGY | 4060 |
| phosphoIGF1R | THERMO FISHER SCIENTIFIC | PA5-35769 |
| phosphoIR | N/A | N/A |
| phosphoIRS1 | MILLIPORE | 05-1087 |
| phosphomTOR | CELL SIGNALING TECHNOLOGY | 5536 |
| phosphoP70S6K | CELL SIGNALING TECHNOLOGY | 9204 |
| phosphoGSK3a | CELL SIGNALING TECHNOLOGY | 9327 |
| phosphoGSK3b | CELL SIGNALING TECHNOLOGY | 5558 |
| phosphoTSC2 | THERMO FISHER SCIENTIFIC | PA5-12845 |
| phosphoPRAS40 | CELL SIGNALING TECHNOLOGY | 2997 |
| phosphoPTEN | CELL SIGNALING TECHNOLOGY | 9551 |

EXAMPLES

The following examples are provided to illustrate certain disclosed embodiments and are not to be construed as limiting the scope of this disclosure in any way.

Example 1—Immunoprecipitation of AKT-mTOR Pathway Proteins and Discovery-MS

Figure 2:
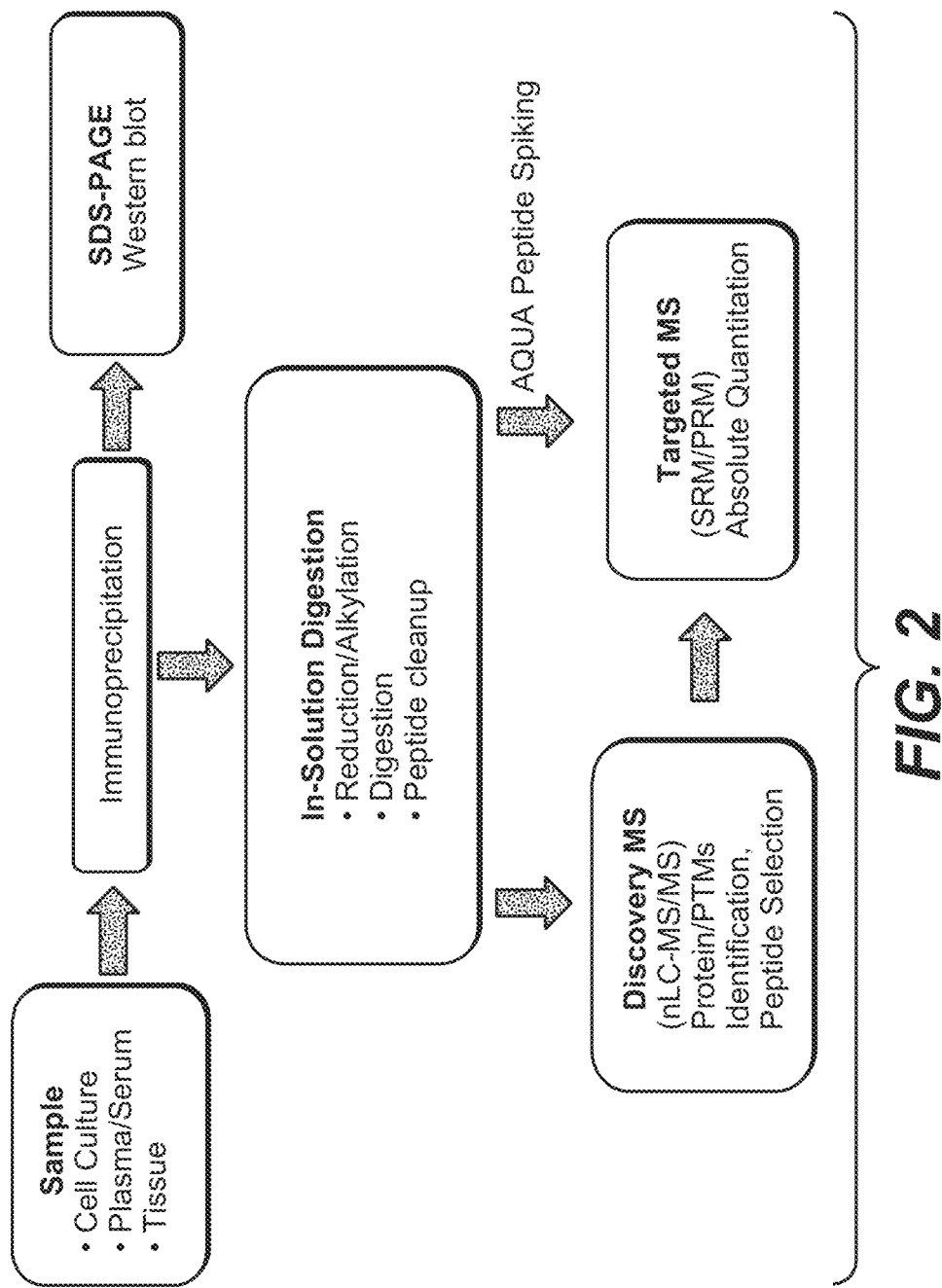
FIG. 2 shows one representative workflow for an immunoprecipitation-enriched mass spectrometry assay to identify AKT-mTOR pathway proteins.

AKT-mTOR pathway proteins play central roles in diseases including cancer. The identification of AKT-mTOR pathway proteins, while desired as a means for monitoring disease progression, and as a tool for scientific research, has been limited in part because of the low abundance of AKT-mTOR pathway proteins, and in part due to a lack of validated methods and reagents. Phosphorylated AKT-mTOR pathway proteins are particularly important to identify and quantify as a measure of protein activation status, and also as markers for disease progression. As shown in FIG. 2, methods and reagents for detecting AKT-mTOR pathway proteins, including phosphorylated proteins, and their protein interactions, were designed and tested. Multi-plex immunoprecipitation (IP) to MS (mIP-MS) was assessed for the ability to measure total and phosphorylated AKT-mTOR pathway targets. mIP-MS methods were also compared to existing singleplex immunoassay (Western Blot (WB) and ELISA) and multiplex Luminex assays.

Cell Culture

For all assays, HCT116 (ATCC product#CCL-247), MCF7, (ATCC product#HTB-22) and A549 (ATCC product#CCL-185) cells were grown in Hamm's F-12K media, McCoy's 5A Media, and MEM Media, respectively, with 10% FBS/1×PenStrep to approximately 70-80% confluency. Cells were starved in 0.1% charcoal stripped FBS for 24 hours before stimulation with 100 ng/ml of IGF (CST product#8917SF) for 15 minutes.

Controls

Western Blot (WB), ELISA, and Luminex Assays were used as controls to compare to the IP-MS method described herein. The reagents and methods for Western Blots are summarized in Table 6.

TABLE 6

List of IP to Western Blot validated antibodies for AKT-mTOR Pathway Targets

| Target | WB Antibody | Vendor | Dilution | Gel | Notes |
|---|---|---|---|---|---|
| AKT | 4691 | CELL SIGNALING TECHNOLOGY | (1:1000) | Tris Glycine | |
| phosphoAKT | 4051 | CELL SIGNALING TECHNOLOGY | (1:1000) | Tris Glycine | |
| IGF1R | 3027 | CELL SIGNALING TECHNOLOGY | (1:1000) | Tris Acetate | |
| phosphoIGF1R | Biotinylated AP50303 | Abgent | (1:10,000) | Tris Acetate | SA HRP Secondary |
| IR | 3020 | CELL SIGNALING TECHNOLOGY | (1:1000) | Tris Acetate | |
| phosphoIR | 07-841 | Millipore | (1:1000) | Tris Acetate | |
| IRS1 | 2382 | CELL SIGNALING TECHNOLOGY | (1:1000) | Tris Acetate | |
| phosphoIRS1 | Biotinylated 05-1087 | Millipore | (1:1000) | Tris Acetate | SA HRP Secondary |
| mTOR | 2983 | CELL SIGNALING TECHNOLOGY | (1:1000) | Tris Acetate | |
| phosphomTOR | 5536 | CELL SIGNALING TECHNOLOGY | (1:1000) | Tris Acetate | |
| P70S6K | AP3289g | Abgent | (1:1000) | Tris Glycine | |
| phosphoP70S6K | 9204 | CELL SIGNALING TECHNOLOGY | (1:1000) | Tris Glycine | |
| GSK3a | 4337 | CELL SIGNALING TECHNOLOGY | (1:1000) | Tris Glycine | Clean Blot |
| phosphoGSK3a | 8506 | CELL SIGNALING TECHNOLOGY | (1:1000) | Tris Glycine | Clean Blot |
| GSK3b | 12456 | CELL SIGNALING TECHNOLOGY | (1:1000) | Tris Glycine | Clean Blot |
| TSC2 | 4308 | CELL SIGNALING TECHNOLOGY | (1:1000) | Tris Acetate | |
| phosphoTSC2 | ab52962 | Abcam | (1:10,000) | Tris Acetate | |
| PRAS40 | AP14275b | Abgent | (1:1000) | Tris Glycine | |
| phosphoPRAS40 | 2997 | CELL SIGNALING TECHNOLOGY | (1:1000) | Tris Glycine | |
| PTEN | 9188 | CELL SIGNALING TECHNOLOGY | (1:1000) | Tris Glycine | Clean Blot |
| phosphoPTEN | 9551 | CELL SIGNALING TECHNOLOGY | (1:1000) | Tris Glycine | Clean Blot |

Secondary Antibodies: Goat Anti-Rabbit Ab (Thermo Fisher Scientific, PN: 32460), Goat Anti-Mouse Ab (Thermo Fisher Scientific, PN:32430), Pierce High Sensitivity Streptavidin-HRP (Thermo Fisher Scientific, PN: 21130)
SDS-PAGE Gels: NuPAGE 3-8% Tris-Acetate Gel (Thermo Fisher Scientific, PN: EA03752BOX), Novex 4-20% Tris-Glycine Midi Gel (Thermo Fisher Scientific, PN: WT4201BX10)
Clean Blot: Thermo Fisher Scientific, PN: 21232

Reagents for ELISA kits are shown in Table 7.

TABLE 7

ELISA kits for 11 total and 10 phosphorylated AKT-mTOR Pathway Targets

| Target | Vendor | Product# | Lot# |
|---|---|---|---|
| Total GSK3B | Cell Signaling Technology | 7265 | 0004 |
| Phospho GSK3β | Cell Signaling Technology | 7311 | 0004 |
| Phospho GSK3β | Life Technologies | KHO0461 | 16404995B |
| Total IRS1 | Cell Signaling Technology | 7328 | 0011 |
| Phospho IRS1 | N/A | N/A | N/A |
| Total PTEN | Cell Signaling Technology | 7882 | 0005 |
| Phospho PTEN | Cell Signaling Technology | 7285 | 0006 |
| Total PRAS40 | Cell Signaling Technology | 7331 | 0003 |
| Phospho PRAS40 | Cell Signaling Technology | 7327 | 0004 |
| Total Insulin Receptor | Cell Signaling Technology | 7069 | 0006; 0004 |
| Phospho Insulin Receptor | Cell Signaling Technology | 7258 | 0016; 0015 |
| Total IGF1R | R&D Systems | DYC305-2 | 1324480 |
| Total IGF1R | Abcam | ab100546 | GR212867-1 |
| Phospho IGF1R | Cell Signaling Technology | 7302 | 0015 |
| Total GSK3α | R&D Systems | DYC2157-2 | 1299193 |
| Phospho GSK3α | R&D Systems | DYC4125-2 | 1300987 |
| Total TSC2 | Lifespan Biosciences | LS-F2369 | 50 |
| Phospho TSC2 | Lifespan Biosciences | LS-F1233 | 49 |
| Total AKT1 | Cell Signaling Technology | 7170 | 0048 |
| Phospho AKT1 | Cell Signaling Technology | 7160 | 0093 |
| Total mTOR | Cell Signaling Technology | 7974 | 0006 |
| Phospho mTOR | Cell Signaling Technology | 7976 | 0007 |
| Total p70S6K | Cell Signaling Technology | 7038 | 0004 |
| Phospho p70S6K | Cell Signaling Technology | 7063 | 0005 |

For Luminex Assays, AKT Pathway (total) Magnetic 7-Plex Panel (Thermo Fisher Scientific, PN: LH00002M), AKT Pathway (phospho) Magnetic 7-Plex Panel (Thermo Fisher Scientific, PN: LH00001M), Milliplex Map Akt/mTOR Phosphoprotein Magnetic Bead 11-Plex Kit (Millipore, PN: 48-611MAG) and Milliplex Map Total Akt/mTOR Magnetic Bead 11-Plex Kit (Millipore, PN: 48-612MAG) were used as recommended in instruction manuals. Luminex MagPix instrument was used to acquire and analyze Luminex assay data.

Immunoprecipitation and MS Sample Preparation

The Thermo Scientific™ Pierce MS-Compatible Magnetic IP Kit (Protein A/G) was used to screen and validate antibodies for 11 total and 10 phosphorylated AKT-mTOR pathway proteins from 500 µg cell lysate. Validated antibodies were biotinylated with the Thermo Scientific™ Pierce Antibody Biotinylation Kit for IP. The Thermo Scientific™ Pierce MS-Compatible Magnetic IP Kit (Streptavidin) was used to perform the single or multiplex IPs for target enrichment. IP samples were processed by an in-solution digestion method where IP eluates were reconstituted in 6M Urea, 50 mM TEAB, pH 8.5 followed by reduction, alkylation and trypsin digestion overnight at 37° C. The digested samples were acidified with TFA before MS analysis.

Liquid Chromatography and Mass Spectrometry

Prior to MS analysis, tryptic digest samples were desalted on-line using the Thermo Scientific™ Acclaim™ PepMap 100 C18 Trap Column. For discovery MS, the samples were analyzed by nanoLC-MS/MS using a Thermo Scientific™ Dionex™ UltiMate™ 3000 RSLCnano System and Thermo Scientific™ Q Exactive™ HF Hybrid Quadrupole-Orbitrap Mass Spectrometer. For targeted MS, the samples were analyzed using the UltiMate 3000 RSLCnano System and the Thermo Scientific™ TSQ™ Vantage™ Mass Spectrometer (SRM mode) or the Thermo Scientific™ Q Exactive™ HF Hybrid Quadrupole-Orbitrap Mass Spectrometer (PRM mode).

MS Data Analysis

Discovery MS data were analyzed with Thermo Scientific™ Proteome Discoverer™ 1.4 to assess percent sequence coverage, unique peptides, MS1 intensities, spectral counts and PTMs. The Proteome Discoverer software searches were executed using the Uniprot human protein database. Tryptic peptides with highest MS1 intensity and relevant phosphorylation sites were selected from the discovery data for targeted assay development. For targeted MS data analysis, Thermo Scientific™ Pinpoint software and Skyline software (University of Washington) were used to measure limit of quantitation (LOQ) from the calibration curve and target analyte concentration from unknown samples.

Results

As shown in FIG. 3, AKT-mTOR pathway proteins were immunoprecipitated from unstimulated and IGF-stimulated A549 lysate with Thermo Scientific™ Pierce MS-Compatible Magnetic IP Kits (Protein A/G or Streptavidin) for MS analysis. A variety of antibodies were screened to determine effectiveness in both ability to IP AKT-mTOR pathway proteins, and also for their usefulness when combined with MS. Table 1 (above) provides a list of antibodies validated for use in the IP-MS methods. Table 2 (above) provides a list of antibodies tested, but found to be less successful.

Higher numbers of unique peptides were identified in IP enriched samples as compared to neat (non-IP-enriched) lysate. See FIG. 3. Protein isoforms and interacting protein partners were identified for AKT, IGF1R and mTOR targets. Relevant phosphorylation sites were detected for AKT1, AKT2, mTOR, IGF1R and PRAS40. Candidate quantitative peptides were selected for targeted MS assay development.

Limits of detection (LOD) and lower limits of quantification (LLOQ) were analyzed for twelve AKT-mTOR pathway proteins, including AKT2, AKT1, mTOR, IGF1R, IR, PRAS40, p70S6K, TSC2, PTEN, GSK3alpha, GSK3beta, and IRS1. Results are presented in FIG. 4. The assay dynamic range, representing the concentration range between the lower to upper limits of quantification (LLOQ to ULOQ), is the range where protein concentration is measurable with acceptable levels of accuracy and precision. To ensure linearity of the measurement, for each internal standard peptide the linear signal-to-abundance range (LLOQ and ULOQ) was determined from dilution series experiments spanning concentrations of 500-0.08 fmol on column, spiked into a constant light peptide at 36 fmol and 200 ng of equimolar concentration of 6 proteins digest.

Example 2—Multiplex IP of AKT-mTOR Pathway Proteins and Multiplex MS

Eleven total and ten phosphorylated AKT-mTOR pathway protein targets were enriched simultaneously from unstimulated and IGF stimulated MCF7 lysates with biotinylated antibodies and Thermo Scientific™ Pierce MS-Compatible Magnetic IP Kit (Streptavidin). MCF7 cells were starved in 0.1% charcoal stripped FBS for 24 hours before stimulation with 100 ng/ml of IGF for 15 minutes. Validated IP-MS antibodies are biotinylated for 11 total and 10 phosphorylated AKT-mTOR pathway targets using the Thermo Scientific™ Pierce Antibody Biotinylation Kit for IP (PN: 90407) as recommended in instruction manual. 1 µg of each biotinylated antibody for 11 total targets were added simultaneously to 1000 µg of control and IGF stimulated MCF7 cell lysate in duplicate. 1 µg of each biotinylated antibody for 10 total targets were added simultaneously to 1000 µg of control and IGF stimulated MCF7 cell lysate in duplicate. IP was performed as recommended in the Thermo Scientific™ Pierce MS-Compatible Magnetic IP Kit (Streptavidin) (PN: 90408) with the following modification. 5 microgram of streptavidin magnetic beads per microgram of biotinylated antibody concentration was used for multiplex IP.

IP samples were processed by an in-solution digestion method where IP eluates were reconstituted in 6M Urea, 50 mM TEAB, pH 8.5 followed by reduction (5 mM TCEP for 30 minutes at 35° C.), alkylation (20 mM Iodoacetamide in dark at room temperature for 30 minutes) and trypsin digestion overnight at 37° C. The digested samples were acidified with 3.5 µL of 10% TFA before discovery MS analysis. For discovery MS, the samples were analyzed by nanoLC-MS/MS using a Thermo Scientific™ Dionex™ UltiMate™ 3000 RSLCnano System and Thermo Scientific™ Q Exactive™ HF Hybrid Quadrupole-Orbitrap Mass Spectrometer. Briefly, the digested samples were cleaned on-line using the C18 trap column (Thermo Fisher Scientific, PN: 164564) followed by reversed-phase separation using the analytical C18 column (75 µm i.d.×15 cm, nanoViper, 3 µm particle size, Thermo Fisher Scientific, PN: ES800) with a 2-30% gradient of Buffer B using Buffer A (0.1% formic acid) and Buffer B (0.1% formic acid/99.9% acetonitrile) at 0.300 µL/min.

FIG. 5 shows that the IP-nanoLC-MS/MS analysis was able to identify 11 proteins in the multiplex phosphor-assay, and 12 proteins for multiplex total assay. MS analysis of multiplex total assay identified interacting proteins (PIK3R1, PIK3R2, PIK3CB, PIK3CA, GSKIP and TSC1) of AKT-mTOR Pathway Targets. Tables 8 and 9 provide listings of the antibodies used in this multiplex IP.

Figure 6:
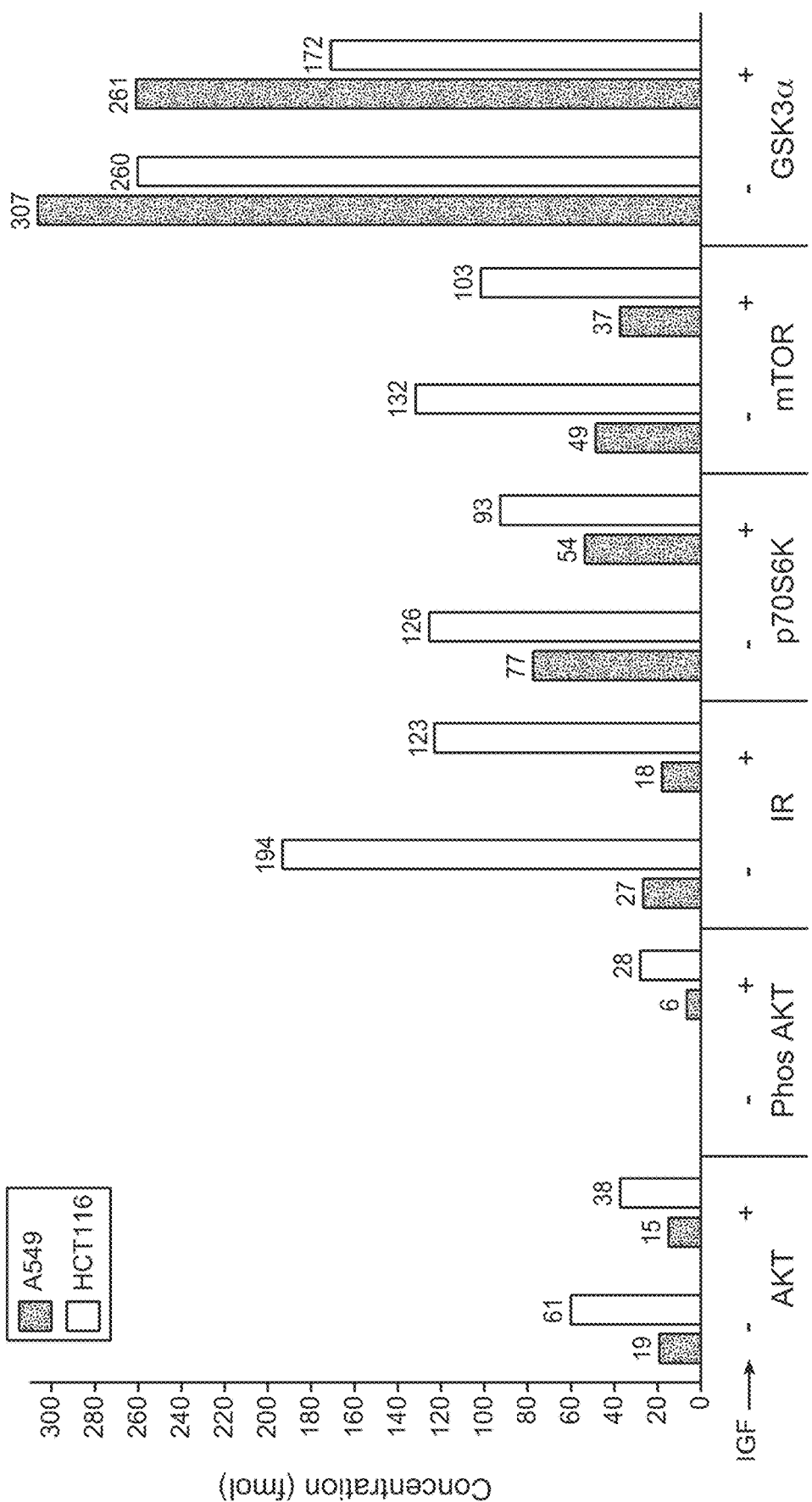
FIG. 6 shows representative results from a multiplex immunoprecipitation plus nanoLC-PRM/MS assay AKT-mTOR pathway proteins. Darker gray bars are A549 cells, and lighter gray bars are HCT116 cells.
Figure 7A:
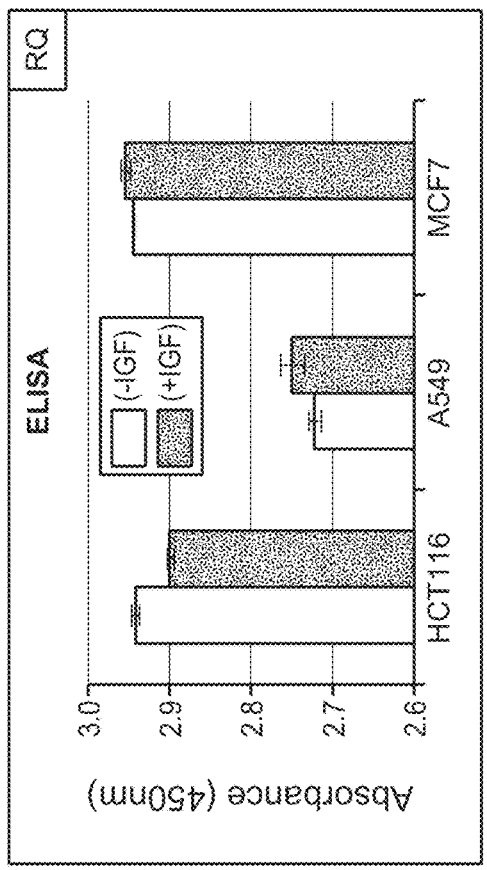
FIGS. 7A, 7B, 7C, 7D, 7E, 7F, 7G, and 7H show a comparison of various methods to detect AKT-mTOR pathway proteins, including Luminex, ELISA, Western Blot, and the IP-Mass spec assay in IGF stimulated (dark gray) and (non-stimulated (light gray) cells.
Figure 7B:
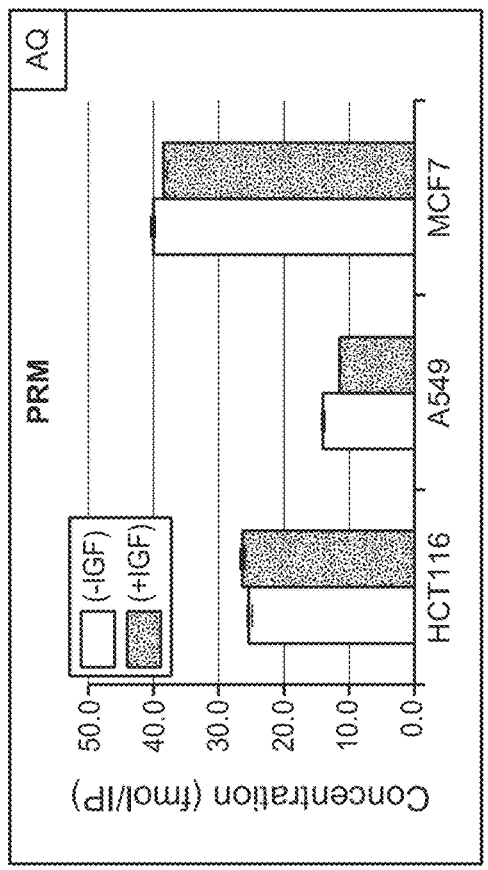
Figure 7C:
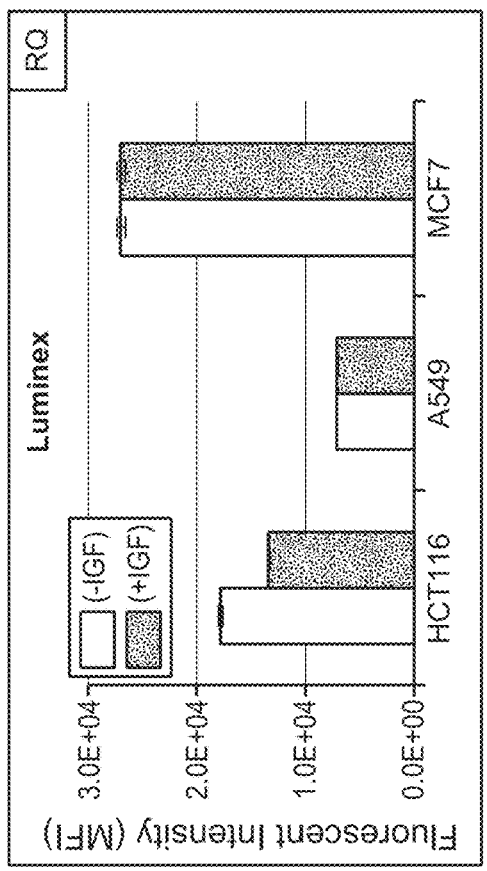
Figure 7D:
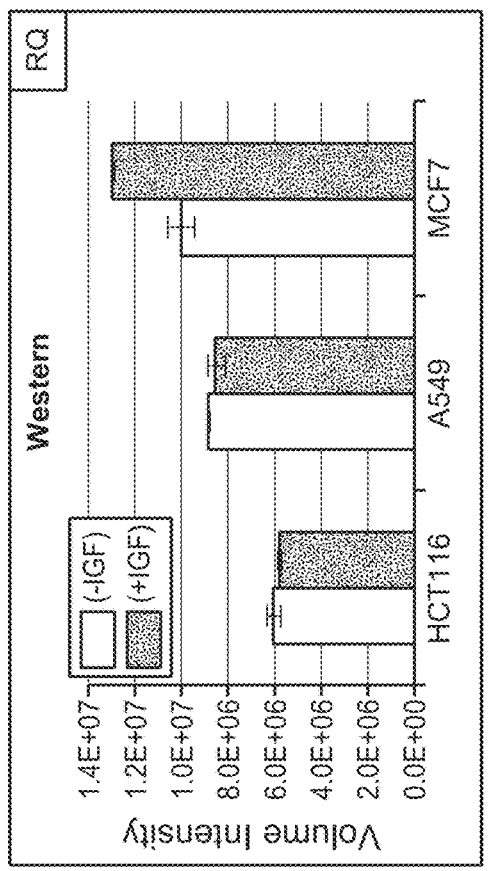
Figure 7E:
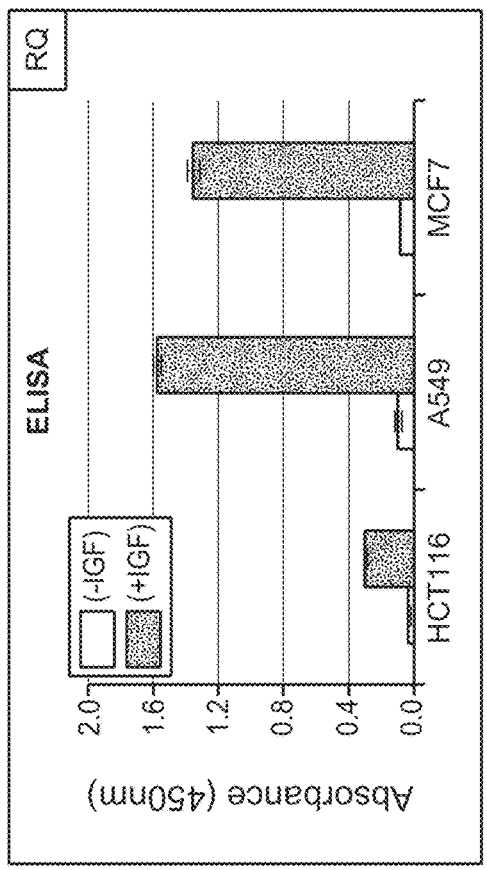
Figure 7F:
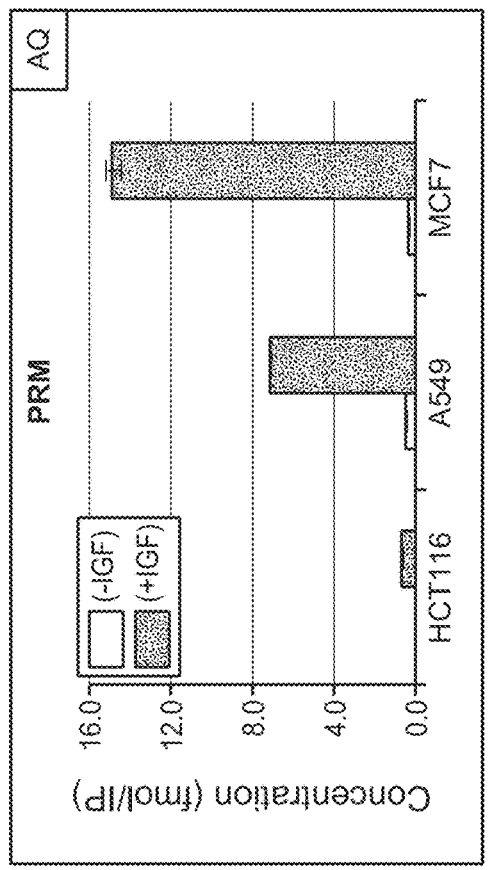
Figure 7G:
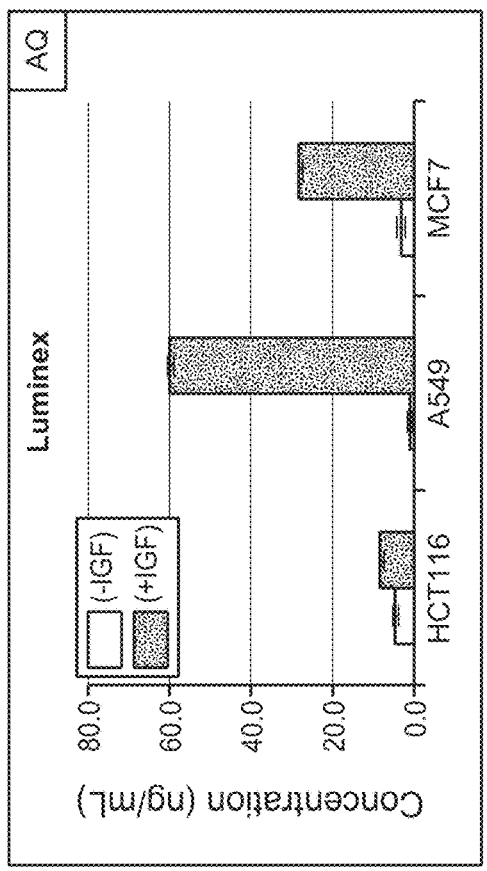
Figure 7H:
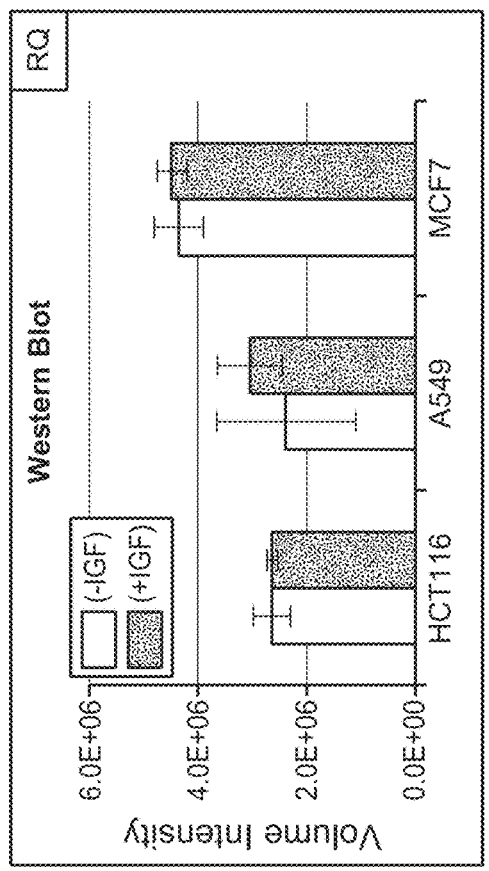

Next the ability of IP-MS to quantify sub-fmol concentrations of AKT-mTOR pathway proteins via the disclosed IP-MS methods was tested. As shown in FIG. 6, a multiplex IP enrichment of AKT (Total & Phospho), IR, p70S6K, mTOR, and GSK3α was performed from unstimulated and IGF stimulated A549 and HCT116 lysates with Thermo Scientific™ Pierce MS-Compatible Magnetic IP Kit (Streptavidin). A549 and HCT116 cells were starved in 0.1% charcoal stripped FBS for 24 hours before stimulation with 100 ng/ml of IGF for 15 minutes. Validated IP-MS antibodies are biotinylated for Total AKT, Phospho AKT, IR, p70S6K, mTOR, and GSK3α pathway targets using the Thermo Scientific™ Pierce Antibody Biotinylation Kit for IP (PN: 90407) as recommended in instruction manual. 1 µg of each biotinylated antibody was added simultaneously to 1000 µg of control and IGF stimulated A549 and HCT116 cell lysates in duplicate. IP was performed as recommended in the Thermo Scientific™ Pierce MS-Compatible Magnetic IP Kit (Streptavidin) (PN: 90408) with the following modification. 5 microgram of streptavidin magnetic beads per microgram of biotinylated antibody concentration was used for multiplex IP. IP samples were processed by an in-solution digestion method where IP eluates were reconstituted in 6M Urea, 50 mM TEAB, pH 8.5 followed by reduction (5 mM TCEP for 30 minutes at 35° C.), alkylation (20 mM Iodoacetamide in dark at room temperature for 30 minutes) and trypsin digestion overnight at 37° C. The digested samples were acidified with 3.5 µL of 10% TFA before discovery MS analysis. Internal standard peptides were spiked in digested IP samples to make final volume of 6.66 fmol/ul. For targeted MS, the samples were analyzed by nanoLC-PRM/MS using a Thermo Scientific™ Dionex™ UltiMate™ 3000 RSLCnano System and Thermo Scientific™ Q Exactive™ HF Hybrid Quadrupole-Orbitrap Mass Spectrometer. Briefly, the digested samples were cleaned on-line using the C18 trap column (Thermo Fisher Scientific, PN: 164564) followed by reversed-phase separation using the analytical C18 column (75 pin i.d.×15 cm, nanoViper, 3 µm particle size, Thermo Fisher Scientific, PN: ES800) with a 2-30% gradient of Buffer B using Buffer A (0.1% formic acid) and Buffer B (0.1% formic acid/99.9% acetonitrile) at 0.300 µL/min. Total targets were quantified in low to sub-fmol concentrations by nanoLC-PRM/MS. Up-regulation of phospho AKT was seen after IGF stimulation in both A549 and HCT116 cell lines. The slight decrease in concentrations for total AKT, IR, mTOR, GSK3α and p70S6K targets was observed after IGF stimulation in both A549 and HCT116 cells.

Example 3—Benchmarking

Next, comparison of mIP-tMS assays with current immunoassay techniques to quantitate AKT-mTOR pathway targets from unstimulated and IGF stimulated A549, HCT116 and MCF7 lysates were performed. Western Blot, ELISA, and Luminex assays were performed as described above and according to manufacturer's instructions. mIP-tMS was performed as in Example 2.

FIGS. 7A-7D show quantitation of total AKT. FIGS. 7E-7H show quantitation of phosphorylated IGF1R across all 4 techniques. Lower correlation was observed across techniques. The lower correlation could be due to different antibodies used or each assay and antibody specificity. Up-regulation in phosphorylated IGF1R observed after IGF stimulation in 3 of 4 techniques. Western blot for phosphor IGF1R showed no significant differences in control and IGF stimulated cell lysates.

A summary of AKT-mTOR pathway proteins that were identified and quantified using the IP-MS methods described herein is provided in FIG. 8. Most of the AKT-mTOR pathway targets were not identified in discovery MS and quantitated by targeted MS (PRM or SRM) without enrichment by immunoprecipitation.

Immunoprecipitation using particular selected antibodies resulted in a higher yield of AKT-mTOR pathway target proteins and less non-specific binding proteins than MS alone. IP-MS assay was also more successful than other commercially available non-MS assays. Furthermore, IP to MS analysis of total and phosphorylated AKT-mTOR pathway proteins enabled identification of multiple isoforms, relevant protein interactions and phosphorylation sites. Total and phosphorylated mIP-tMS assays allowed simultaneous quantitation of 12 total and 11 phosphorylated AKT-mTOR pathway proteins in the low to sub-fmol range from unstimulated and IGF stimulated A549, HCT116 and MCF7 cell lysates. The benchmarking of mIP-tMS assays showed moderate correlation for quantitation of total and phosphorylated target relative abundance compared to WB, ELISA and Luminex assays. The low concordance for a few targets is possibly due to differences in the specificity of antibodies used for each assay. Major advantages of the MS-based assay are high confidence in target identity coupled with simultaneous quantitation of multiple targets, interacting proteins and their phosphophorylated forms.

Example 4—Tissue Sample Validation

Tissue lysis protocol was optimized for IP-MS application. Briefly, 50-100 mg of human and murine tissue samples were washed with 5 mL 1× cold PBS three times. Tissue samples was minced in 5 mL 1× cold PS using scissor followed by homogenization in IP lysis buffer (Thermo Fisher Scientific PN: 87788) and electronic Polytron Handheld Tissue Tearer. Homogenized tissue samples were passed through tissue strainer (Thermo Fisher Scientific PN: 87791) to prepare tissue lysates before IP. To validate the IP-MS method in murine and human tissue lysate, eleven total and ten phosphorylated AKT-mTOR pathway protein targets were enriched simultaneously from normal mouse lung tissue lysate, normal mouse kidney tissue lysate, and normal human lung tissue lysate as per Example 2. A549 cell lysate was used as a non-tissue control. As shown in Table 10, the IP-MS method described herein is capable of validating AKT-mTOR pathway proteins in murine and human tissue lysate in addition to cell lysate. Seven out of eleven AKT-mTOR pathway protein targets were identified in normal human lung tissue, and nine out of eleven AKT-mTOR pathway protein targets were identified for normal mouse kidney tissue using our IP-MS method.

TABLE 10

11-plex total IP-MS assay validating tissue lysate.
Intensities of top 3 peptides

| Total Targets | A549 Cell Line | Mouse Lung | Human Lung | Mouse Kidney |
|---|---|---|---|---|
| AKT1 | 2.0E+08 | 1.2E+08 | 2.6E+06 | |
| PRAS40 | 9.8E+08 | 1.0E+08 | 2.3E+07 | 2.5E+07 |
| GSK3b | 8.0E+08 | 8.3E+08 | L2E+08 | 3.4E+08 |
| IGF1R | 5.4E+08 | 7.4E+07 | 1.2E+07 | 1.4E+08 |
| IRS1 | 7.2E+07 | 7.1E+06 | | |
| IR1 | 2.1E+08 | 6.2E+07 | 3.4E+07 | 1.5E+08 |
| mTOR | 9.4E+07 | 1.3E+07 | 2.2E+07 | 6.7E+07 |
| p70S6K | 6.4E+07 | 3.8E+08 | | 1.8E+08 |
| TSC2 | 9.1E+07 | 1.9E+07 | | 3.7E+07 |
| PTEN | 6.1E+07 | 5.3E+07 | 2.4E+07 | 1.3E+08 |
| GSk3a | 2.8E+08 | 1.4E+08 | | 9.2E+07 |

What is claimed:

1. A method for detecting AKT-mTOR pathway proteins, comprising
   a. treating a biological sample with at least one antibody capable of immunoprecipitating AKT-mTOR pathway protein(s) from a biological sample;
   b. digesting the immunoprecipitated target protein(s);
   c. assaying the digested protein(s) via mass spectrometry to determine the presence of at least one peptide for AKT-mTOR pathway protein(s), wherein the at least one peptide for AKT-mTOR pathway protein(s) is less than 40 amino acids in length and further wherein the at least one peptide comprises one or more of:
   i. a peptide comprising SEQ ID NO: 106 corresponding to MTOR_14,
   ii. a peptide comprising SEQ ID NO: 96 corresponding to mTOR_4,
   iii. a peptide comprising SEQ ID NO: 101 corresponding to mTOR_9,
   iv. a peptide comprising SEQ ID NO: 110 corresponding to MTOR_18,
   v. a peptide comprising SEQ ID NO: 157 corresponding to p70S6K_1, vi. a peptide comprising SEQ ID NO: 159 corresponding to p70S6K_3, and d. detecting one or more AKT-mTOR pathway protein(s) in the sample.

2. The method of claim 1, further comprising determining the quantity of AKT-mTOR pathway protein.

3. The method of claim 1, wherein the AKT-mTOR pathway protein is phosphorylated.

4. The method of claim 1, wherein the at least one AKT-mTOR pathway peptide comprises two or more peptides chosen from SEQ ID NOS: 106, 96, 101, 110, 157, and 159.

5. The method of claim 1, wherein the biological sample is human.

6. The method of claim 1, wherein the antibody to detect phosphorylated AKT-mTOR pathway protein comprises an antibody that binds to phosphorylated AKT, phosphorylated IGF1R, phosphorylated IRS, phosphorylated IRS1, phosphorylated mTOR, phosphorylated P70S6K, phosphorylated GSK3a, phosphorylated GSK3b, phosphorylated TSC2, phosphorylated PRAS40, or phosphorylated PTEN.

7. The method of claim 1, wherein the antibody to detect non-phosphorylated AKT-mTOR pathway protein comprises an immunoprecipitation (IP) antibody that binds to AKT, IGF1R, IR, IRS1, mTOR, P70S6K, GSK3a, GSK3b, TSC2, PRAS40, or PTEN.

8. The method of claim 1, wherein the peptide is modified with a detectable label, wherein the detectable label comprises an isotope selected from $^{13}C$, $^{15}N$, $^{2}H$ and $^{18}O$.

9. The method of claim 1, wherein the antibody is chosen from an antibody that binds to AKT1, AKT (pan), AKT2, phosphorylated AKT2 (pSer474), phosphorylated AKT (pSer473), phosphorylated IGF-1R (Tyr1161/Tyr1165/Tyr1166), phosphorylated IGF1 Receptor (IGF1R) pTyr1158+1162+1163, phosphorylated IGF1R pTyr1161, phosphorylated IGF-I Receptor β (Tyr1131), phosphorylated Insulin Receptor β (Tyr1146), IGF-I/Insulin Receptor β, INSR/Insulin Receptor, α-Insulin Receptor β subunit, INSR/Insulin Receptor alpha, phosphorylated Insulin Receptor (Y972), IRS1, phosphorylated IRS1 (pSer312), phosphorylated IRS1 (Ser307 mouse/Ser312 human), phosphorylated IRS-1 (pSer1101), mTOR, phosphorylated mTOR (pSer2448), S6K, S6K1, phosphorylated p70 S6 Kinase (pThr389/pThr412), phosphorylated p70 S6 Kinase (pThr389), phosphorylated p70 S6 Kinase (pThr421/pSer424), phosphorylated GSK-3α/β (pSer21/pSer9), GSK3α, phosphorylated GSK-3α (Ser21), GSK-3β, phosphorylated GSK-3β (pSer9), phosphorylated Tuberin/TSC2 (pSer939), TSC2, S6 ribosomal protein, phosphorylated S6 ribosomal protein (pSer235+236), PRAS40, phosphorylated PRAS40 (pThr246), phosphorylated PTEN (pSer380), or PTEN.

10. The method of claim 9, wherein the antibody is capable of immunoprecipitating more than one AKT-mTOR pathway protein.

11. The method of claim 1, wherein a first antibody is capable of immunoprecipitating a phosphorylated AKT-mTOR pathway protein, and a second antibody is capable of immunoprecipitating a non-phosphorylated version of the AKT-mTOR pathway protein precipitated by the first antibody.

12. The method of claim 1, wherein step a) comprises treating the sample with a labelled antibody capable of binding to the pathway protein to provide a labelled antibody-protein conjugate; and binding the labelled antibody-protein conjugate with a capture agent capable of binding to the labelled antibody to isolate the target protein from the sample.

13. The method of claim 1, wherein the quantity of an AKT-mTOR pathway protein is determined by adding an internal standard peptide of known amount to the digested protein prior to mass spectrometry, wherein the internal standard peptide has the same amino acid sequence as the AKT-mTOR pathway peptide, and is detectably labeled, and determining the quantity of an AKT-mTOR pathway peptide by comparison to the internal standard.

14. The method of claim 1, wherein the quantity of an AKT-mTOR pathway protein is determined by a method comprising comparing an amount of the AKT-mTOR pathway peptide to an internal standard peptide of known amount, wherein both the peptide in the biological sample and the internal standard peptide are chosen from SEQ ID NOS: 106, 96, 101, 110, 157, and 159.

15. The method of claim 13, wherein the internal standard peptide is chosen from SEQ ID NOS: 106, 96, 101, 110, 157, and 159:1.

16. The method of claim 1, wherein the digesting comprises a protease or chemical digest.

17. The method of claim 1, wherein the AKT-mTOR pathway protein is selected from RAC-alpha serine/threonine-protein kinase (AKT1), RAC-beta serine/threonine-protein kinase (AKT2), insulin receptor (INSR), insulin-like growth factor 1 receptor (IGF1R), insulin receptor substrate 1 (IRS1), tuberin (TSC2), serine/threonine-protein kinase mTOR (mTOR), glycogen synthase kinase-3 alpha (GSK3a), glycogen synthase kinase-3 beta (GSK3b), GSK3a/GSK3b, ribosomal protein S6 kinase beta-1 (p70S6K; RPS6KB1), 40S ribosomal protein S6 (RPS6), proline-rich AKT1 substrate 1 (PRAS40; AKT1S1), and phosphatidylinositol 3,4,5-triphosphate 3-phosphatase and dual-specificity protein phosphatase (PTEN).

18. The method of claim 2, wherein the lower limit of quantification is within the range of about 0.05-0.75 fmol.

* * * * *

UNITED STATES PATENT AND TRADEMARK OFFICE
CERTIFICATE OF CORRECTION

| | |
|---|---|
| PATENT NO. | : 11,561,226 B2 |
| APPLICATION NO. | : 16/081377 |
| DATED | : January 24, 2023 |
| INVENTOR(S) | : Bhavinkumar Patel et al. |

It is certified that error appears in the above-identified patent and that said Letters Patent is hereby corrected as shown below:

In the Claims

In Claim 15, Column 244, Line 34, delete ":1" after "159".

Signed and Sealed this
Eighteenth Day of April, 2023

Katherine Kelly Vidal
*Director of the United States Patent and Trademark Office*

SEQUENCE LISTING

<160> NUMBER OF SEQ ID NOS: 424

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 1

Asn Asp Gly Thr Phe Ile Gly Tyr Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 2

Ser Leu Leu Ser Gly Leu Leu Lys
1               5

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 3

Glu Ala Pro Leu Asn Asn Phe Ser Val Ala Gln Cys Gln Leu Met Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (8)..(8)
<223> OTHER INFORMATION: Phosphorylation

<400> SEQUENCE: 4

Arg Pro His Phe Pro Gln Phe Ser Tyr Ser Ala Ser Gly Thr Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 5

Arg Pro His Phe Pro Gln Phe Ser Tyr Ser Ala Ser Gly Thr Ala
1               5                   10                  15

<210> SEQ ID NO 6
<211> LENGTH: 9

```
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 6

Ser Asp Gly Ser Phe Ile Gly Tyr Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 7

Ser Leu Leu Ala Gly Leu Leu Lys
1               5

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (7)..(7)
<223> OTHER INFORMATION: Phosphorylation

<400> SEQUENCE: 8

Thr His Phe Pro Gln Phe Ser Tyr Ser Ala Ser Ile Arg Glu
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 9

Thr His Phe Pro Gln Phe Ser Tyr Ser Ala Ser Ile Arg Glu
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 10

Leu Val Pro Pro Phe Lys Pro Gln Val Thr Ser Glu Thr Asp Thr Arg
1               5                   10                  15

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence
```

```
<400> SEQUENCE: 11

Ser Leu Leu Ser Gly Leu Leu Ile Lys
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (1)..(1)
<223> OTHER INFORMATION: Carbamidomethylation

<400> SEQUENCE: 12

Cys Ser Val Ala Ala Tyr Val Ser Ala Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 13

Cys Ser Val Ala Ala Tyr Val Ser Ala Arg
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 14

Gly Leu Lys Pro Trp Thr Gln Tyr Ala Ile Phe Val Lys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (6)..(6)
<223> OTHER INFORMATION: Carbamidomethylation

<400> SEQUENCE: 15

Ile Glu Leu Gln Ala Cys Asn Gln Asp Thr Pro Glu Glu Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence
```

```
<400> SEQUENCE: 16

Thr Ile Asp Ser Val Thr Ser Ala Gln Glu Leu Arg
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 17

Thr Asn Cys Pro Ala Thr Val Ile Asn Gly Gln Phe Val Glu Arg
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Carbamidomethylation

<400> SEQUENCE: 18

Thr Asn Cys Pro Ala Thr Val Ile Asn Gly Gln Phe Val Glu Arg
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 19

Thr Asn Gly Asp Gln Ala Ser Cys Glu Asn Glu Leu Leu Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (8)..(8)
<223> OTHER INFORMATION: Carbamidomethylation

<400> SEQUENCE: 20

Thr Asn Gly Asp Gln Ala Ser Cys Glu Asn Glu Leu Leu Lys
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 21
```

```
Val Cys His Leu Leu Glu Gly Glu Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (2)..(2)
<223> OTHER INFORMATION: Carbamidomethylation

<400> SEQUENCE: 22

Val Cys His Leu Leu Glu Gly Glu Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 23

Thr Val Asn Glu Ser Ala Ser Leu Arg
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 24

Asp Ile Ile Lys Gly Glu Ala Glu Thr Arg
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 25

Asp Ile Tyr Glu Thr Asp Tyr Tyr Arg
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 26

Asp Ile Tyr Glu Thr Asp Tyr Tyr Arg Lys
1               5                   10
```

-continued

```
<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation

<400> SEQUENCE: 27

Asp Ile Tyr Glu Thr Asp Tyr Tyr Arg
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (7)..(7)
<223> OTHER INFORMATION: Phosphorylation

<400> SEQUENCE: 28

Asp Ile Tyr Glu Thr Asp Tyr Tyr Arg
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (8)..(8)
<223> OTHER INFORMATION: Phosphorylation

<400> SEQUENCE: 29

Asp Ile Tyr Glu Thr Asp Tyr Tyr Arg
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (7)..(8)
<223> OTHER INFORMATION: Phosphorylation

<400> SEQUENCE: 30

Asp Ile Tyr Glu Thr Asp Tyr Tyr Arg
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence
```

```
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (7)..(7)
<223> OTHER INFORMATION: Phosphorylation

<400> SEQUENCE: 31

Asp Ile Tyr Glu Thr Asp Tyr Tyr Arg
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (8)..(8)
<223> OTHER INFORMATION: Phosphorylation

<400> SEQUENCE: 32

Asp Ile Tyr Glu Thr Asp Tyr Tyr Arg
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (7)..(8)
<223> OTHER INFORMATION: Phosphorylation

<400> SEQUENCE: 33

Asp Ile Tyr Glu Thr Asp Tyr Tyr Arg
1               5

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 34

Ala Glu Asn Gly Pro Gly Pro Gly Val Leu Val Leu Arg
1               5                   10

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
```

-continued

```
            Native peptide sequence
<220> FEATURE:
<221> NAME/KEY: MOD_RES
<222> LOCATION: (8)..(8)
<223> OTHER INFORMATION: Carbamidomethylation
<220> FEATURE:
<221> NAME/KEY: MOD_RES
<222> LOCATION: (12)..(12)
<223> OTHER INFORMATION: Carbamidomethylation

<400> SEQUENCE: 35

His Tyr Tyr Tyr Ala Gly Val Cys Val Pro Ala Cys Pro Pro Asn Thr
1               5                   10                  15

Tyr Arg

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 36

His Tyr Tyr Tyr Ala Gly Val Cys Val Pro Ala Cys Pro Pro Asn Thr
1               5                   10                  15

Tyr Arg

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Carbamidomethylation

<400> SEQUENCE: 37

Leu Gly Cys Ser Ala Ser Asn Phe Val Phe Ala Arg
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 38

Leu Gly Cys Ser Ala Ser Asn Phe Val Phe Ala Arg
1               5                   10

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 39

Ser Leu Arg Pro Glu Met Glu Asn Asn Pro Val Leu Ala Pro Pro Ser
1               5                   10                  15
```

Leu Ser Lys

```
<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 40

Thr Thr Ile Asn Asn Glu Tyr Asn Tyr Arg
1               5                   10

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 41

Val Ala Gly Leu Glu Ser Leu Gly Asp Leu Phe Pro Asn Leu Thr Val
1               5                   10                  15

Ile Arg

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 42

Tyr Ala Asp Gly Thr Ile Asp Ile Glu Glu Val Thr Glu Asn Pro Lys
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (11)..(11)
<223> OTHER INFORMATION: Carbamidomethylation

<400> SEQUENCE: 43

Tyr Gly Ser Gln Val Glu Asp Gln Arg Glu Cys Val Ser Arg
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 44

Tyr Gly Ser Gln Val Glu Asp Gln Arg Glu Cys Val Ser Arg
1               5                   10
```

```
<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 45

Ile Asp Ile His Ser Cys Asn His Glu Ala Glu Lys
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 46

Gly Val Val Lys Asp Glu Pro Glu Thr Arg
1               5                   10

<210> SEQ ID NO 47
<211> LENGTH: 26
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 47

Ala Ser Ser Asp Gly Glu Gly Thr Met Ser Arg Pro Ala Ser Val Asp
1               5                   10                  15

Gly Ser Pro Val Ser Pro Ser Thr Asn Arg
            20                  25

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (1)..(1)
<223> OTHER INFORMATION: Carbamidomethylation

<400> SEQUENCE: 48

Cys Gly His Ser Glu Asn Phe Phe Phe Ile Glu Val Gly Arg
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 49

Cys Gly His Ser Glu Asn Phe Phe Phe Ile Glu Val Gly Arg
1               5                   10

<210> SEQ ID NO 50
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (1)..(1)
<223> OTHER INFORMATION: Carbamidomethylation

<400> SEQUENCE: 50

Cys Thr Pro Gly Thr Gly Leu Gly Thr Ser Pro Ala Leu Ala Gly Asp
1               5                   10                  15

Glu Ala Ala Ser Ala Ala Asp Leu Asp Asn Arg
            20                  25

<210> SEQ ID NO 51
<211> LENGTH: 27
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 51

Cys Thr Pro Gly Thr Gly Leu Gly Thr Ser Pro Ala Leu Ala Gly Asp
1               5                   10                  15

Glu Ala Ala Ser Ala Ala Asp Leu Asp Asn Arg
            20                  25

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 52

His His Leu Asn Asn Pro Pro Pro Ser Gln Val Gly Leu Thr Arg
1               5                   10                  15

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 53

His Ser Ser Glu Thr Phe Ser Ser Thr Pro Ser Ala Thr Arg
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 54

Lys Gly Ser Gly Asp Tyr Met Pro Met Ser Pro Lys
1               5                   10

<210> SEQ ID NO 55
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (2)..(2)
<223> OTHER INFORMATION: Carbamidomethylation

<400> SEQUENCE: 55

Leu Cys Gly Ala Ala Gly Gly Leu Glu Asn Gly Leu Asn Tyr Ile Asp
1               5                   10                  15

Leu Asp Leu Val Lys
            20

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 56

Leu Cys Gly Ala Ala Gly Gly Leu Glu Asn Gly Leu Asn Tyr Ile Asp
1               5                   10                  15

Leu Asp Leu Val Lys
            20

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 57

Ser Val Ser Ala Pro Gln Gln Ile Ile Asn Pro Ile Arg
1               5                   10

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 58

Thr Glu Ser Ile Thr Ala Thr Ser Pro Ala Ser Met Val Gly Gly Lys
1               5                   10                  15

Pro Gly Ser Phe Arg
            20

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 59

Thr Gly Ile Ala Ala Glu Glu Val Ser Leu Pro Arg
```

```
1               5                   10
```

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 60

```
Ser Tyr Pro Glu Glu Gly Leu Glu Met His Pro Leu Glu Arg
1               5                   10
```

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 61

```
Thr His Ser Ala Gly Thr Ser Pro Thr Ile Thr His Gln Lys
1               5                   10
```

<210> SEQ ID NO 62
<211> LENGTH: 26
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation

<400> SEQUENCE: 62

```
Ala Ser Ser Asp Gly Glu Gly Thr Met Ser Arg Pro Ala Ser Val Asp
1               5                   10                  15

Gly Ser Pro Val Ser Pro Ser Thr Asn Arg
            20                  25
```

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation

<400> SEQUENCE: 63

```
His Ser Ser Glu Thr Phe Ser Ser Thr Pro Ser Ala Thr Arg
1               5                   10
```

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES

```
<222> LOCATION: (10)..(10)
<223> OTHER INFORMATION: Phosphorylation

<400> SEQUENCE: 64

Lys Gly Ser Gly Asp Tyr Met Pro Met Ser Pro Lys
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (7)..(7)
<223> OTHER INFORMATION: Methionine sulfoxide
<220> FEATURE:
<221> NAME/KEY: MOD_RES
<222> LOCATION: (9)..(9)
<223> OTHER INFORMATION: Methionine sulfoxide
<220> FEATURE:
<221> NAME/KEY: MOD_RES
<222> LOCATION: (10)..(10)
<223> OTHER INFORMATION: Phosphorylation

<400> SEQUENCE: 65

Lys Gly Ser Gly Asp Tyr Met Pro Met Ser Pro Lys
1               5                   10

<210> SEQ ID NO 66
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (2)..(2)
<223> OTHER INFORMATION: Carbamidomethylation
<220> FEATURE:
<221> NAME/KEY: MOD_RES
<222> LOCATION: (14)..(14)
<223> OTHER INFORMATION: Phosphorylation

<400> SEQUENCE: 66

Leu Cys Gly Ala Ala Gly Gly Leu Glu Asn Gly Leu Asn Tyr Ile Asp
1               5                   10                  15

Leu Asp Leu Val Lys
            20

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (14)..(14)
<223> OTHER INFORMATION: Phosphorylation

<400> SEQUENCE: 67

Leu Cys Gly Ala Ala Gly Gly Leu Glu Asn Gly Leu Asn Tyr Ile Asp
1               5                   10                  15

Leu Asp Leu Val Lys
            20
```

```
<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (8)..(8)
<223> OTHER INFORMATION: Phosphorylation

<400> SEQUENCE: 68

Thr Glu Ser Ile Thr Ala Thr Ser Pro Ala Ser Met Val Gly Gly Lys
1               5                   10                  15

Pro Gly Ser Phe Arg
            20

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (8)..(8)
<223> OTHER INFORMATION: Phosphorylation
<220> FEATURE:
<221> NAME/KEY: MOD_RES
<222> LOCATION: (12)..(12)
<223> OTHER INFORMATION: Methionine sulfoxide

<400> SEQUENCE: 69

Thr Glu Ser Ile Thr Ala Thr Ser Pro Ala Ser Met Val Gly Gly Lys
1               5                   10                  15

Pro Gly Ser Phe Arg
            20

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 70

Ala Pro Ala Gln Thr Pro Ala Glu Pro Thr Pro Gly Tyr Glu Val Gly
1               5                   10                  15

Gln Arg

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 71

Asp Ser Phe Arg Ala Arg Ser Thr Ser Leu Asn Glu Arg Pro Lys
1               5                   10                  15

<210> SEQ ID NO 72
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 72

Glu Ala Pro Ala Lys Leu Glu Ser Gln Ala Gly Gln Gln Val Ser Arg
1               5                   10                  15

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 73

Gly Tyr Thr Ile Ser Asp Ser Ala Pro Ser Arg
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 74

Leu Ile Ser Ser Val Glu Asp Phe Thr Glu Phe Val
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 75

Leu Val Thr Val Thr Thr Ser Val Gly Thr Gly Thr Arg
1               5                   10

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 76

Ser Gln Ser Gly Thr Leu Asp Gly Glu Ser Ala Ala Trp Ser Ala Ser
1               5                   10                  15

Gly Glu Asp Ser Arg
            20

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      Native peptide sequence
```

<400> SEQUENCE: 77

Ser Val Gln Leu Leu Asp Gln Ile Pro Ser Tyr Asp Thr His Lys
1               5                   10                  15

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 78

Val Gly Ala Leu Asp Val Pro Ala Ser Gln Phe Leu Gly Ser Ala Thr
1               5                   10                  15

Ser Pro Gly Pro Arg
            20

<210> SEQ ID NO 79
<211> LENGTH: 23
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 79

Val Val Ser Ser Glu Gly Gly Arg Pro Ser Val Asp Leu Ser Phe Gln
1               5                   10                  15

Pro Ser Gln Pro Leu Ser Lys
            20

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 80

Tyr Thr Glu Phe Leu Thr Gly Leu Gly Arg
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 81

Tyr Val Phe Ser Asn Phe Thr Ala Val Pro Lys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 82

```
Ser Asn Pro Thr Asp Ile Tyr Pro Ser Lys
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 83

Phe Asn Ser Cys Tyr Leu Asp Glu Tyr Ile Ala Arg
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 84

Gly Gln Pro Glu Gly Pro Leu Pro Ser Ser Pro Arg
1               5                   10

<210> SEQ ID NO 85
<211> LENGTH: 25
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 85

Ser Leu Leu Gly Leu Asp Ser Gly Glu Leu Gln Ser Gly Pro Glu Ser
1               5                   10                  15

Ser Ser Ser Pro Gly Val His Val Arg
            20                  25

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (9)..(9)
<223> OTHER INFORMATION: Phosphorylation

<400> SEQUENCE: 86

Asp Ser Phe Arg Ala Arg Ser Thr Ser Leu Asn Glu Arg Pro Lys
1               5                   10                  15

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation
```

<400> SEQUENCE: 87

Gly Tyr Thr Ile Ser Asp Ser Ala Pro Ser Arg
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation

<400> SEQUENCE: 88

Leu Ile Ser Ser Val Glu Asp Phe Thr Glu Phe Val
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (4)..(4)
<223> OTHER INFORMATION: Phosphorylation

<400> SEQUENCE: 89

Leu Ile Ser Ser Val Glu Asp Phe Thr Glu Phe Val
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(4)
<223> OTHER INFORMATION: Phosphorylation

<400> SEQUENCE: 90

Leu Ile Ser Ser Val Glu Asp Phe Thr Glu Phe Val
1               5                   10

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation

<400> SEQUENCE: 91

Ser Thr Ser Leu Asn Glu Arg Pro Lys
1               5

<210> SEQ ID NO 92

```
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 92

Ser Thr Ser Leu Asn Glu Arg Pro Lys
1               5

<210> SEQ ID NO 93
<211> LENGTH: 19
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (16)..(16)
<223> OTHER INFORMATION: Carbamidomethylation

<400> SEQUENCE: 93

Ala Val Leu Ala Leu His Gln Asp Leu Phe Ser Leu Ala Gln Gln Cys
1               5                   10                  15

Ile Asp Lys

<210> SEQ ID NO 94
<211> LENGTH: 19
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 94

Ala Val Leu Ala Leu His Gln Asp Leu Phe Ser Leu Ala Gln Gln Cys
1               5                   10                  15

Ile Asp Lys

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 95

Asp Leu Glu Leu Ala Val Pro Gly Thr Tyr Asp Pro Asn Gln Pro Ile
1               5                   10                  15

Ile Arg

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 96

Gly Asn Asn Leu Gln Asp Thr Leu Arg
1               5
```

```
<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 97

Gly Pro Thr Pro Ala Ile Leu Glu Ser Leu Ile Ser Ile Asn Asn Lys
1               5                   10                  15

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 98

Gly Tyr Thr Leu Ala Asp Glu Glu Glu Asp Pro Leu Ile Tyr Gln His
1               5                   10                  15

Arg

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 99

Ile His Gly Ala Leu Leu Ile Leu Asn Glu Leu Val Arg
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 100

Ile Gln Ser Ile Ala Pro Ser Leu Gln Val Ile Thr Ser Lys
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 101

Leu Phe Asp Ala Pro Glu Ala Pro Leu Pro Ser Arg
1               5                   10

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic
      Native peptide sequence
```

<400> SEQUENCE: 102

Leu Gly Glu Trp Gln Leu Asn Leu Gln Gly Ile Asn Glu Ser Thr Ile
1               5                   10                  15

Pro Lys

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 103

Leu Ile His Gln Leu Leu Thr Asp Ile Gly Arg
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 104

Ser Pro Ser Ser Glu Val Trp Phe Asp Arg
1               5                   10

<210> SEQ ID NO 105
<211> LENGTH: 24
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 105

Thr Asp Ser Tyr Ser Ala Gly Gln Ser Val Glu Ile Leu Asp Gly Val
1               5                   10                  15

Glu Leu Gly Glu Pro Ala His Lys
            20

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 106

Thr Leu Val Leu Leu Leu Gly Val Asp Pro Ser Arg
1               5                   10

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 107

Val Glu Val Phe Glu His Ala Val Asn Asn Thr Ala Gly Asp Asp Leu

```
1               5                   10                  15

Ala Lys

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 108

Val Leu Gly Leu Leu Gly Ala Leu Asp Pro Tyr Lys
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 109

Trp Thr Leu Val Asn Asp Glu Thr Gln Ala Lys
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 110

Glu Thr Ser Phe Asn Gln Ala Tyr Gly Arg
1               5                   10

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 111

Thr Leu Asp Gln Ser Pro Glu Leu Arg
1               5

<210> SEQ ID NO 112
<211> LENGTH: 24
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation

<400> SEQUENCE: 112

Thr Asp Ser Tyr Ser Ala Gly Gln Ser Val Glu Ile Leu Asp Gly Val
1               5                   10                  15

Glu Leu Gly Glu Pro Ala His Lys
```

<210> SEQ ID NO 113
<211> LENGTH: 24
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (1)..(1)
<223> OTHER INFORMATION: Phosphorylation

<400> SEQUENCE: 113

Thr Asp Ser Tyr Ser Ala Gly Gln Ser Val Glu Ile Leu Asp Gly Val
1               5                   10                  15

Glu Leu Gly Glu Pro Ala His Lys
            20

<210> SEQ ID NO 114
<211> LENGTH: 24
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (1)..(1)
<223> OTHER INFORMATION: Phosphorylation
<220> FEATURE:
<221> NAME/KEY: MOD_RES
<222> LOCATION: (3)..(3)
<223> OTHER INFORMATION: Phosphorylation

<400> SEQUENCE: 114

Thr Asp Ser Tyr Ser Ala Gly Gln Ser Val Glu Ile Leu Asp Gly Val
1               5                   10                  15

Glu Leu Gly Glu Pro Ala His Lys
            20

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 115

Asp Ile Lys Pro Gln Asn Leu Leu Val Asp Pro Asp Thr Ala Val Leu
1               5                   10                  15

Lys

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (7)..(7)
<223> OTHER INFORMATION: Carbamidomethylation

<400> SEQUENCE: 116

-continued

```
Leu Ser Pro Leu Glu Ala Cys Ala His Ser Phe Phe Asp Glu Leu Arg
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 117

Leu Ser Pro Leu Glu Ala Cys Ala His Ser Phe Phe Asp Glu Leu Arg
1               5                   10                  15

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (11)..(11)
<223> OTHER INFORMATION: Carbamidomethylation

<400> SEQUENCE: 118

Ser Leu Ala Tyr Ile His Ser Gln Gly Val Cys His Arg
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 119

Ser Leu Ala Tyr Ile His Ser Gln Gly Val Cys His Arg
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 120

Ser Gln Glu Val Ala Tyr Thr Asp Ile Lys
1               5                   10

<210> SEQ ID NO 121
<211> LENGTH: 20
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (9)..(9)
<223> OTHER INFORMATION: Carbamidomethylation

<400> SEQUENCE: 121

Thr Pro Pro Glu Ala Ile Ala Leu Cys Ser Ser Leu Leu Glu Tyr Thr
```

-continued

```
                1               5                  10                 15
Pro Ser Ser Arg
            20

<210> SEQ ID NO 122
<211> LENGTH: 20
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 122

Thr Pro Pro Glu Ala Ile Ala Leu Cys Ser Ser Leu Leu Glu Tyr Thr
1               5                  10                 15

Pro Ser Ser Arg
            20

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 123

Thr Ser Ser Phe Ala Glu Pro Gly Gly Gly Gly Gly Gly Gly Gly Gly
1               5                  10                 15

Gly Pro Gly Gly Ser Ala Ser Gly Pro Gly Gly Thr Gly Gly Gly Lys
            20                  25                 30

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 124

Val Thr Thr Val Val Ala Thr Leu Gly Gln Gly Pro Glu Arg
1               5                  10

<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 125

Asp Ser Gly Lys Val Thr Thr Val Val Ala Thr Leu Gly Gln Gly Pro
1               5                  10                 15

Glu Arg

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 126
```

Tyr Phe Phe Tyr Ser Ser Gly Glu Lys
1               5

<210> SEQ ID NO 127
<211> LENGTH: 32
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation

<400> SEQUENCE: 127

Thr Ser Ser Phe Ala Glu Pro Gly Gly Gly Gly Gly Gly Gly Gly
1               5                   10                  15

Gly Pro Gly Gly Ser Ala Ser Gly Pro Gly Gly Thr Gly Gly Gly Lys
            20                  25                  30

<210> SEQ ID NO 128
<211> LENGTH: 18
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 128

Asp Glu Val Tyr Leu Asn Leu Val Leu Asp Tyr Val Pro Glu Thr Val
1               5                   10                  15

Tyr Arg

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 129

Asp Ile Lys Pro Gln Asn Leu Leu Leu Asp Pro Asp Thr Ala Val Leu
1               5                   10                  15

Lys

<210> SEQ ID NO 130
<211> LENGTH: 29
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 130

Asp Thr Pro Ala Leu Phe Asn Phe Thr Thr Gln Glu Leu Ser Ser Asn
1               5                   10                  15

Pro Pro Leu Ala Thr Ile Leu Ile Pro Pro His Ala Arg
            20                  25

<210> SEQ ID NO 131
<211> LENGTH: 11
<212> TYPE: PRT
<213> ORGANISM: Artificial Sequence

```
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (2)..(2)
<223> OTHER INFORMATION: Carbamidomethylation

<400> SEQUENCE: 131

Leu Cys Asp Ser Gly Glu Leu Val Ala Ile Lys
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 132

Leu Cys Asp Ser Gly Glu Leu Val Ala Ile Lys
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 133

Leu Leu Glu Tyr Thr Pro Thr Ala Arg
1               5

<210> SEQ ID NO 134
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (11)..(11)
<223> OTHER INFORMATION: Carbamidomethylation

<400> SEQUENCE: 134

Ser Leu Ala Tyr Ile His Ser Phe Gly Ile Cys His Arg
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 135

Ser Leu Ala Tyr Ile His Ser Phe Gly Ile Cys His Arg
1               5                   10

<210> SEQ ID NO 136
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      Native peptide sequence
<220> FEATURE:
<221> NAME/KEY: MOD_RES
<222> LOCATION: (8)..(8)
<223> OTHER INFORMATION: Carbamidomethylation

<400> SEQUENCE: 136

Thr Thr Ser Phe Ala Glu Ser Cys Lys Pro Val Gln Gln Pro Ser Ala
1               5                   10                  15

Phe Gly Ser Met Lys
            20

<210> SEQ ID NO 137
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 137

Thr Thr Ser Phe Ala Glu Ser Cys Lys Pro Val Gln Gln Pro Ser Ala
1               5                   10                  15

Phe Gly Ser Met Lys
            20

<210> SEQ ID NO 138
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (8)..(8)
<223> OTHER INFORMATION: Carbamidomethylation
<220> FEATURE:
<221> NAME/KEY: MOD_RES
<222> LOCATION: (20)..(20)
<223> OTHER INFORMATION: Methionine sulfoxide

<400> SEQUENCE: 138

Thr Thr Ser Phe Ala Glu Ser Cys Lys Pro Val Gln Gln Pro Ser Ala
1               5                   10                  15

Phe Gly Ser Met Lys
            20

<210> SEQ ID NO 139
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (20)..(20)
<223> OTHER INFORMATION: Methionine sulfoxide

<400> SEQUENCE: 139

Thr Thr Ser Phe Ala Glu Ser Cys Lys Pro Val Gln Gln Pro Ser Ala
1               5                   10                  15

Phe Gly Ser Met Lys
            20
```

```
<210> SEQ ID NO 140
<211> LENGTH: 24
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 140

Val Thr Thr Val Val Ala Thr Pro Gly Gln Gly Pro Asp Arg Pro Gln
1               5                   10                  15

Glu Val Ser Tyr Thr Asp Thr Lys
            20

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 141

Lys Leu Asp His Cys Asn Ile Val Arg
1               5

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 142

Asp Ser Ser Gly Thr Gly His Phe Thr Ser Gly Val Arg
1               5                   10

<210> SEQ ID NO 143
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (8)..(8)
<223> OTHER INFORMATION: Carbamidomethylation
<220> FEATURE:
<221> NAME/KEY: MOD_RES
<222> LOCATION: (20)..(20)
<223> OTHER INFORMATION: Methionine sulfoxide

<400> SEQUENCE: 143

Thr Thr Ser Phe Ala Glu Ser Cys Lys Pro Val Gln Gln Pro Ser Ala
1               5                   10                  15

Phe Gly Ser Met Lys
            20

<210> SEQ ID NO 144
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (20)..(20)
<223> OTHER INFORMATION: Methionine sulfoxide

<400> SEQUENCE: 144

Thr Thr Ser Phe Ala Glu Ser Cys Lys Pro Val Gln Gln Pro Ser Ala
1               5                   10                  15

Phe Gly Ser Met Lys
            20

<210> SEQ ID NO 145
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (8)..(8)
<223> OTHER INFORMATION: Carbamidomethylation

<400> SEQUENCE: 145

Thr Thr Ser Phe Ala Glu Ser Cys Lys Pro Val Gln Gln Pro Ser Ala
1               5                   10                  15

Phe Gly Ser Met Lys
            20

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation

<400> SEQUENCE: 146

Thr Thr Ser Phe Ala Glu Ser Cys Lys Pro Val Gln Gln Pro Ser Ala
1               5                   10                  15

Phe Gly Ser Met Lys
            20

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (9)..(9)
<223> OTHER INFORMATION: Carbamidomethylation

<400> SEQUENCE: 147
```

```
Gly Glu Pro Asn Val Ser Tyr Ile Cys Ser Arg
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 148

Gly Glu Pro Asn Val Ser Tyr Ile Cys Ser Arg
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (7)..(7)
<223> OTHER INFORMATION: Phosphorylation
<220> FEATURE:
<221> NAME/KEY: MOD_RES
<222> LOCATION: (9)..(9)
<223> OTHER INFORMATION: Carbamidomethylation

<400> SEQUENCE: 149

Gly Glu Pro Asn Val Ser Tyr Ile Cys Ser Arg
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (7)..(7)
<223> OTHER INFORMATION: Phosphorylation

<400> SEQUENCE: 150

Gly Glu Pro Asn Val Ser Tyr Ile Cys Ser Arg
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (6)..(6)
<223> OTHER INFORMATION: Phosphorylation
<220> FEATURE:
<221> NAME/KEY: MOD_RES
<222> LOCATION: (9)..(9)
<223> OTHER INFORMATION: Carbamidomethylation

<400> SEQUENCE: 151

Gly Glu Pro Asn Val Ser Tyr Ile Cys Ser Arg
1               5                   10
```

```
<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (6)..(6)
<223> OTHER INFORMATION: Phosphorylation

<400> SEQUENCE: 152

Gly Glu Pro Asn Val Ser Tyr Ile Cys Ser Arg
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (6)..(7)
<223> OTHER INFORMATION: Phosphorylation
<220> FEATURE:
<221> NAME/KEY: MOD_RES
<222> LOCATION: (9)..(9)
<223> OTHER INFORMATION: Carbamidomethylation

<400> SEQUENCE: 153

Gly Glu Pro Asn Val Ser Tyr Ile Cys Ser Arg
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (6)..(7)
<223> OTHER INFORMATION: Phosphorylation

<400> SEQUENCE: 154

Gly Glu Pro Asn Val Ser Tyr Ile Cys Ser Arg
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 155

Thr Pro Pro Glu Ala Ile Ala Leu Cys Ser Arg
1               5                   10

<210> SEQ ID NO 156
<211> LENGTH: 11
<212> TYPE: PRT
<213> ORGANISM: Artificial Sequence
<220> FEATURE:
```

-continued

```
<223> OTHER INFORMATION: Description of Artificial Sequence: Synthetic
      Native peptide sequence
<220> FEATURE:
<221> NAME/KEY: MOD_RES
<222> LOCATION: (9)..(9)
<223> OTHER INFORMATION: Carbamidomethylation

<400> SEQUENCE: 156

Thr Pro Pro Glu Ala Ile Ala Leu Cys Ser Arg
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 157

Asp Gly Phe Tyr Pro Ala Pro Asp Phe Arg
1               5                   10

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 158

Asp Leu Lys Pro Glu Asn Ile Met Leu Asn His Gln Gly His Val Lys
1               5                   10                  15

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 159

Phe Glu Ile Ser Glu Thr Ser Val Asn Arg
1               5                   10

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 160

Phe Ser Pro Gly Asp Phe Trp Gly Arg
1               5

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 161
```

His Ile Asn Trp Glu Glu Leu Leu Ala Arg
1               5                   10

<210> SEQ ID NO 162
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 162

His Pro Phe Ile Val Asp Leu Ile Tyr Ala Phe Gln Thr Gly Gly Lys
1               5                   10                  15

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (5)..(5)
<223> OTHER INFORMATION: Carbamidomethylation

<400> SEQUENCE: 163

Ile Arg Pro Glu Cys Phe Glu Leu Leu Arg
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 164

Ile Arg Pro Glu Cys Phe Glu Leu Leu Arg
1               5                   10

<210> SEQ ID NO 165
<211> LENGTH: 18
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 165

Leu Gly Ala Gly Pro Gly Asp Ala Gly Glu Val Gln Ala His Pro Phe
1               5                   10                  15

Phe Arg

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 166

Leu Asn Leu Pro Pro Tyr Leu Thr Gln Glu Ala Arg
1               5                   10

```
<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (7)..(7)
<223> OTHER INFORMATION: Carbamidomethylation

<400> SEQUENCE: 167

Leu Thr Asp Phe Gly Leu Cys Lys
1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 168

Leu Thr Asp Phe Gly Leu Cys Lys
1               5

<210> SEQ ID NO 169
<211> LENGTH: 35
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 169

Gln Thr Pro Val Asp Ser Pro Asp Asp Ser Thr Leu Ser Glu Ser Ala
1               5                   10                  15

Asn Gln Val Phe Leu Gly Phe Thr Tyr Val Ala Pro Ser Val Leu Glu
            20                  25                  30

Ser Val Lys
        35

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 170

Thr Pro Val Ser Pro Val Lys
1               5

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 171

Thr Pro Val Ser Pro Val Lys Phe Ser Pro Gly Asp Phe Trp Gly Arg
1               5                   10                  15
```

<210> SEQ ID NO 172
<211> LENGTH: 35
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (24)..(24)
<223> OTHER INFORMATION: Phosphorylation

<400> SEQUENCE: 172

Gln Thr Pro Val Asp Ser Pro Asp Asp Ser Thr Leu Ser Glu Ser Ala
1               5                   10                  15

Asn Gln Val Phe Leu Gly Phe Thr Tyr Val Ala Pro Ser Val Leu Glu
            20                  25                  30

Ser Val Lys
        35

<210> SEQ ID NO 173
<211> LENGTH: 35
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (6)..(6)
<223> OTHER INFORMATION: Phosphorylation

<400> SEQUENCE: 173

Gln Thr Pro Val Asp Ser Pro Asp Asp Ser Thr Leu Ser Glu Ser Ala
1               5                   10                  15

Asn Gln Val Phe Leu Gly Phe Thr Tyr Val Ala Pro Ser Val Leu Glu
            20                  25                  30

Ser Val Lys
        35

<210> SEQ ID NO 174
<211> LENGTH: 35
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (6)..(6)
<223> OTHER INFORMATION: Phosphorylation
<220> FEATURE:
<221> NAME/KEY: MOD_RES
<222> LOCATION: (24)..(24)
<223> OTHER INFORMATION: Phosphorylation

<400> SEQUENCE: 174

Gln Thr Pro Val Asp Ser Pro Asp Asp Ser Thr Leu Ser Glu Ser Ala
1               5                   10                  15

Asn Gln Val Phe Leu Gly Phe Thr Tyr Val Ala Pro Ser Val Leu Glu
            20                  25                  30

Ser Val Lys
        35

<210> SEQ ID NO 175

```
<211> LENGTH: 7
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (1)..(1)
<223> OTHER INFORMATION: Phosphorylation

<400> SEQUENCE: 175

Thr Pro Val Ser Pro Val Lys
1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (4)..(4)
<223> OTHER INFORMATION: Phosphorylation

<400> SEQUENCE: 176

Thr Pro Val Ser Pro Val Lys
1               5

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (1)..(1)
<223> OTHER INFORMATION: Phosphorylation
<220> FEATURE:
<221> NAME/KEY: MOD_RES
<222> LOCATION: (4)..(4)
<223> OTHER INFORMATION: Phosphorylation

<400> SEQUENCE: 177

Thr Pro Val Ser Pro Val Lys
1               5

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (4)..(4)
<223> OTHER INFORMATION: Phosphorylation

<400> SEQUENCE: 178

Thr Pro Val Ser Pro Val Lys Phe Ser Pro Gly Asp Phe Trp Gly Arg
1               5                   10                  15

<210> SEQ ID NO 179
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (1)..(1)
<223> OTHER INFORMATION: Phosphorylation
<220> FEATURE:
<221> NAME/KEY: MOD_RES
<222> LOCATION: (4)..(4)
<223> OTHER INFORMATION: Phosphorylation

<400> SEQUENCE: 179

Thr Pro Val Ser Pro Val Lys Phe Ser Pro Gly Asp Phe Trp Gly Arg
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (1)..(1)
<223> OTHER INFORMATION: Phosphorylation

<400> SEQUENCE: 180

Thr Pro Val Ser Pro Val Lys Phe Ser Pro Gly Asp Phe Trp Gly Arg
1               5                   10                  15

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 181

Asp Ile Pro Gly Leu Thr Asp Thr Thr Val Pro Arg
1               5                   10

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (4)..(4)
<223> OTHER INFORMATION: Carbamidomethylation

<400> SEQUENCE: 182

Gly His Ser Cys Tyr Arg Pro Arg
1               5

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 183

Gly His Ser Cys Tyr Arg Pro Arg
```

```
1               5

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (10)..(10)
<223> OTHER INFORMATION: Carbamidomethylation

<400> SEQUENCE: 184

Leu Asn Ile Ser Phe Pro Ala Thr Gly Cys Gln Lys
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 185

Leu Asn Ile Ser Phe Pro Ala Thr Gly Cys Gln Lys
1               5                   10

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 186

Met Ala Thr Glu Val Ala Ala Asp Ala Leu Gly Glu Glu Trp Lys
1               5                   10                  15

<210> SEQ ID NO 187
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 187

Arg Arg Arg Leu Ser Ser Leu Arg Ala Ser Thr Ser Lys
1               5                   10

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (5)..(5)
<223> OTHER INFORMATION: Phosphorylation

<400> SEQUENCE: 188

Arg Arg Arg Leu Ser Ser Leu Arg Ala Ser Thr Ser Lys
1               5                   10
```

```
<210> SEQ ID NO 189
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (6)..(6)
<223> OTHER INFORMATION: Phosphorylation

<400> SEQUENCE: 189

Arg Arg Arg Leu Ser Ser Leu Arg Ala Ser Thr Ser Lys
1               5                   10

<210> SEQ ID NO 190
<211> LENGTH: 13
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (5)..(6)
<223> OTHER INFORMATION: Phosphorylation

<400> SEQUENCE: 190

Arg Arg Arg Leu Ser Ser Leu Arg Ala Ser Thr Ser Lys
1               5                   10

<210> SEQ ID NO 191
<211> LENGTH: 30
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 191

Ala Ala Thr Ala Ala Arg Pro Pro Ala Pro Pro Ala Pro Gln Pro
1               5                   10                  15

Pro Ser Pro Thr Pro Ser Pro Pro Arg Pro Thr Leu Ala Arg
                20                  25                  30

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (1)..(1)
<223> OTHER INFORMATION: Carbamidomethylation

<400> SEQUENCE: 192

Cys Leu His Asp Ile Ala Leu Ala His Arg
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                       Native peptide sequence

<400> SEQUENCE: 193

Cys Leu His Asp Ile Ala Leu Ala His Arg
1               5                   10

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 194

Glu Ala Glu Asp Thr Gln Val Phe Gly Asp Leu Pro Arg Pro Arg
1               5                   10                  15

<210> SEQ ID NO 195
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 195

Ser Leu Pro Val Ser Val Pro Val Trp Gly Phe Lys
1               5                   10

<210> SEQ ID NO 196
<211> LENGTH: 16
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 196

Ser Ser Asp Glu Glu Asn Gly Pro Pro Ser Ser Pro Asp Leu Asp Arg
1               5                   10                  15

<210> SEQ ID NO 197
<211> LENGTH: 20
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 197

Thr Glu Ala Arg Ser Ser Asp Glu Glu Asn Gly Pro Pro Ser Ser Pro
1               5                   10                  15

Asp Leu Asp Arg
            20

<210> SEQ ID NO 198
<211> LENGTH: 28
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (21)..(21)
<223> OTHER INFORMATION: Carbamidomethylation
```

```
<400> SEQUENCE: 198

Thr Gly Thr Glu Leu Val Leu Leu Thr Ala Ala Pro Pro Pro Pro
1               5                   10                  15

Arg Pro Gly Pro Cys Ala Tyr Ala Ala His Gly Arg
            20                  25

<210> SEQ ID NO 199
<211> LENGTH: 28
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 199

Thr Gly Thr Glu Leu Val Leu Leu Thr Ala Ala Pro Pro Pro Pro
1               5                   10                  15

Arg Pro Gly Pro Cys Ala Tyr Ala Ala His Gly Arg
            20                  25

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 200

Leu Asn Thr Ser Asp Phe Gln Lys
1               5

<210> SEQ ID NO 201
<211> LENGTH: 23
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 201

Glu Ala Glu Asp Thr Gln Val Phe Gly Asp Leu Pro Arg Pro Arg Leu
1               5                   10                  15

Asn Thr Ser Asp Phe Gln Lys
            20

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 202

Gly Ala Leu Ala Glu Ala Ala Arg
1               5

<210> SEQ ID NO 203
<211> LENGTH: 18
<212> TYPE: PRT
<213> ORGANISM: Artificial Sequence
<220> FEATURE:
<223> OTHER INFORMATION: Description of Artificial Sequence: Synthetic
      Native peptide sequence
```

```
<400> SEQUENCE: 203

Ala Ser Gly Arg Pro Glu Glu Leu Trp Glu Ala Val Val Gly Ala Ala
1               5                   10                  15

Glu Arg

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (3)..(3)
<223> OTHER INFORMATION: Phosphorylation

<400> SEQUENCE: 204

Leu Asn Thr Ser Asp Phe Gln Lys
1               5

<210> SEQ ID NO 205
<211> LENGTH: 23
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (18)..(18)
<223> OTHER INFORMATION: Phosphorylation

<400> SEQUENCE: 205

Glu Ala Glu Asp Thr Gln Val Phe Gly Asp Leu Pro Arg Pro Arg Leu
1               5                   10                  15

Asn Thr Ser Asp Phe Gln Lys
            20

<210> SEQ ID NO 206
<211> LENGTH: 24
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 206

Tyr Ser Asp Thr Thr Asp Ser Asp Pro Glu Asn Glu Pro Phe Asp Glu
1               5                   10                  15

Asp Gln His Thr Gln Ile Thr Lys
            20

<210> SEQ ID NO 207
<211> LENGTH: 25
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 207

Tyr Ser Asp Thr Thr Asp Ser Asp Pro Glu Asn Glu Pro Phe Asp Glu
1               5                   10                  15

Asp Gln His Thr Gln Ile Thr Lys Val
            20                  25
```

<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 208

Asn Asn Ile Asp Asp Val Val Arg
1               5

<210> SEQ ID NO 209
<211> LENGTH: 12
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 209

Ala Gln Glu Ala Leu Asp Phe Tyr Gly Glu Val Arg
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic
      Native peptide sequence

<400> SEQUENCE: 210

Ile Tyr Ser Ser Asn Ser Gly Pro Thr Arg
1               5                   10

<210> SEQ ID NO 211
<211> LENGTH: 24
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (2)..(2)
<223> OTHER INFORMATION: Phosphorylation

<400> SEQUENCE: 211

Tyr Ser Asp Thr Thr Asp Ser Asp Pro Glu Asn Glu Pro Phe Asp Glu
1               5                   10                  15

Asp Gln His Thr Gln Ile Thr Lys
            20

<210> SEQ ID NO 212
<211> LENGTH: 25
<212> TYPE: PRT
<213> ORGANISM: Artificial Sequence
<220> FEATURE:
<223> OTHER INFORMATION: Description of Artificial Sequence: Synthetic
      Native peptide sequence
<220> FEATURE:
<221> NAME/KEY: MOD_RES
<222> LOCATION: (2)..(2)
<223> OTHER INFORMATION: Phosphorylation

<400> SEQUENCE: 212

Tyr Ser Asp Thr Thr Asp Ser Asp Pro Glu Asn Glu Pro Phe Asp Glu
1               5                   10                  15

Asp Gln His Thr Gln Ile Thr Lys Val
            20                  25

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: K(13C6; 15N2)

<400> SEQUENCE: 213

Asn Asp Gly Thr Phe Ile Gly Tyr Lys
1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: K(13C6; 15N2)

<400> SEQUENCE: 214

Ser Leu Leu Ser Gly Leu Leu Lys
1               5

<210> SEQ ID NO 215
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (16)..(16)
<223> OTHER INFORMATION: K(13C6; 15N2)

<400> SEQUENCE: 215

Glu Ala Pro Leu Asn Asn Phe Ser Val Ala Gln Cys Gln Leu Met Lys
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: Phosphorylation
<220> FEATURE:
<221> NAME/KEY: MOD_RES
<222> LOCATION: (15)..(15)
<223> OTHER INFORMATION: A(13C3; 15N)

<400> SEQUENCE: 216

Arg Pro His Phe Pro Gln Phe Ser Tyr Ser Ala Ser Gly Thr Ala
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (16)..(16)
<223> OTHER INFORMATION: A(13C3; 15N)

<400> SEQUENCE: 217

Arg Pro His Phe Pro Gln Phe Ser Tyr Ser Ala Ser Gly Thr Ala Ala
1               5                   10                  15

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: K(13C6; 15N2)

<400> SEQUENCE: 218

Ser Asp Gly Ser Phe Ile Gly Tyr Lys
1               5

<210> SEQ ID NO 219
<211> LENGTH: 8
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: K(13C6; 15N2)

<400> SEQUENCE: 219

Ser Leu Leu Ala Gly Leu Leu Lys
1               5

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (7)..(7)
<223> OTHER INFORMATION: Phosphorylation
<220> FEATURE:
<221> NAME/KEY: MOD_RES
<222> LOCATION: (13)..(13)
<223> OTHER INFORMATION: R(13C6; 15N4)

<400> SEQUENCE: 220

Thr His Phe Pro Gln Phe Ser Tyr Ser Ala Ser Ile Arg Glu
1               5                   10

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: R(13C6; 15N4)

<400> SEQUENCE: 221

Thr His Phe Pro Gln Phe Ser Tyr Ser Ala Ser Ile Arg Glu
1               5                   10

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (16)..(16)
<223> OTHER INFORMATION: R(13C6; 15N4)

<400> SEQUENCE: 222

Leu Val Pro Pro Phe Lys Pro Gln Val Thr Ser Glu Thr Asp Thr Arg
1               5                   10                  15

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: K(13C6; 15N2)

<400> SEQUENCE: 223

Ser Leu Leu Ser Gly Leu Leu Ile Lys
1               5

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (1)..(1)
<223> OTHER INFORMATION: Carbamidomethylation
<220> FEATURE:
<221> NAME/KEY: MOD_RES
<222> LOCATION: (10)..(10)
<223> OTHER INFORMATION: R(13C6; 15N4)

<400> SEQUENCE: 224

Cys Ser Val Ala Ala Tyr Val Ser Ala Arg
1               5                   10

<210> SEQ ID NO 225
<211> LENGTH: 10

```
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 225

Cys Ser Val Ala Ala Tyr Val Ser Ala Arg
1               5                   10

<210> SEQ ID NO 226
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: K(13C6; 15N2)

<400> SEQUENCE: 226

Gly Leu Lys Pro Trp Thr Gln Tyr Ala Ile Phe Val Lys
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (6)..(6)
<223> OTHER INFORMATION: Carbamidomethylation
<220> FEATURE:
<221> NAME/KEY: MOD_RES
<222> LOCATION: (14)..(14)
<223> OTHER INFORMATION: R(13C6; 15N4)

<400> SEQUENCE: 227

Ile Glu Leu Gln Ala Cys Asn Gln Asp Thr Pro Glu Glu Arg
1               5                   10

<210> SEQ ID NO 228
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: R(13C6; 15N4)

<400> SEQUENCE: 228

Thr Ile Asp Ser Val Thr Ser Ala Gln Glu Leu Arg
1               5                   10

<210> SEQ ID NO 229
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      Internal standard peptide sequence
<220> FEATURE:
<221> NAME/KEY: MOD_RES
<222> LOCATION: (15)..(15)
<223> OTHER INFORMATION: R(13C6; 15N4)

<400> SEQUENCE: 229

Thr Asn Cys Pro Ala Thr Val Ile Asn Gly Gln Phe Val Glu Arg
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Carbamidomethylation
<220> FEATURE:
<221> NAME/KEY: MOD_RES
<222> LOCATION: (15)..(15)
<223> OTHER INFORMATION: R(13C6; 15N4)

<400> SEQUENCE: 230

Thr Asn Cys Pro Ala Thr Val Ile Asn Gly Gln Phe Val Glu Arg
1               5                   10                  15

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (14)..(14)
<223> OTHER INFORMATION: K(13C6; 15N2)

<400> SEQUENCE: 231

Thr Asn Gly Asp Gln Ala Ser Cys Glu Asn Glu Leu Leu Lys
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: Carbamidomethylation
<220> FEATURE:
<221> NAME/KEY: MOD_RES
<222> LOCATION: (14)..(14)
<223> OTHER INFORMATION: K(13C6; 15N2)

<400> SEQUENCE: 232

Thr Asn Gly Asp Gln Ala Ser Cys Glu Asn Glu Leu Leu Lys
1               5                   10

<210> SEQ ID NO 233
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: K(13C6; 15N2)

<400> SEQUENCE: 233

Val Cys His Leu Leu Glu Gly Glu Lys
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (2)..(2)
<223> OTHER INFORMATION: Carbamidomethylation
<220> FEATURE:
<221> NAME/KEY: MOD_RES
<222> LOCATION: (9)..(9)
<223> OTHER INFORMATION: K(13C6; 15N2)

<400> SEQUENCE: 234

Val Cys His Leu Leu Glu Gly Glu Lys
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: R(13C6; 15N4)

<400> SEQUENCE: 235

Thr Val Asn Glu Ser Ala Ser Leu Arg
1               5

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 236

Asp Ile Ile Lys Gly Glu Ala Glu Thr Arg
1               5                   10

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
```

```
<220> FEATURE:
<221> NAME/KEY: MOD_RES
<222> LOCATION: (9)..(9)
<223> OTHER INFORMATION: R(13C6; 15N4)

<400> SEQUENCE: 237

Asp Ile Tyr Glu Thr Asp Tyr Tyr Arg
1               5

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: K(13C6; 15N2)

<400> SEQUENCE: 238

Asp Ile Tyr Glu Thr Asp Tyr Tyr Arg Lys
1               5                   10

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (9)..(9)
<223> OTHER INFORMATION: R(13C6; 15N4)

<400> SEQUENCE: 239

Asp Ile Tyr Glu Thr Asp Tyr Tyr Arg
1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (7)..(7)
<223> OTHER INFORMATION: Phosphorylation
<220> FEATURE:
<221> NAME/KEY: MOD_RES
<222> LOCATION: (9)..(9)
<223> OTHER INFORMATION: R(13C6; 15N4)

<400> SEQUENCE: 240

Asp Ile Tyr Glu Thr Asp Tyr Tyr Arg
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
      Internal standard peptide sequence
<220> FEATURE:
<221> NAME/KEY: MOD_RES
<222> LOCATION: (8)..(8)
<223> OTHER INFORMATION: Phosphorylation
<220> FEATURE:
<221> NAME/KEY: MOD_RES
<222> LOCATION: (9)..(9)
<223> OTHER INFORMATION: R(13C6; 15N4)

<400> SEQUENCE: 241

Asp Ile Tyr Glu Thr Asp Tyr Tyr Arg
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (7)..(8)
<223> OTHER INFORMATION: Phosphorylation
<220> FEATURE:
<221> NAME/KEY: MOD_RES
<222> LOCATION: (9)..(9)
<223> OTHER INFORMATION: R(13C6; 15N4)

<400> SEQUENCE: 242

Asp Ile Tyr Glu Thr Asp Tyr Tyr Arg
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (7)..(7)
<223> OTHER INFORMATION: Phosphorylation
<220> FEATURE:
<221> NAME/KEY: MOD_RES
<222> LOCATION: (9)..(9)
<223> OTHER INFORMATION: R(13C6; 15N4)

<400> SEQUENCE: 243

Asp Ile Tyr Glu Thr Asp Tyr Tyr Arg
1               5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (8)..(8)
<223> OTHER INFORMATION: Phosphorylation
```

```
<220> FEATURE:
<221> NAME/KEY: MOD_RES
<222> LOCATION: (9)..(9)
<223> OTHER INFORMATION: R(13C6; 15N4)

<400> SEQUENCE: 244

Asp Ile Tyr Glu Thr Asp Tyr Tyr Arg
1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (7)..(8)
<223> OTHER INFORMATION: Phosphorylation
<220> FEATURE:
<221> NAME/KEY: MOD_RES
<222> LOCATION: (9)..(9)
<223> OTHER INFORMATION: R(13C6; 15N4)

<400> SEQUENCE: 245

Asp Ile Tyr Glu Thr Asp Tyr Tyr Arg
1               5

<210> SEQ ID NO 246
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: R(13C6; 15N4)

<400> SEQUENCE: 246

Ala Glu Asn Gly Pro Gly Pro Gly Val Leu Val Leu Arg
1               5                   10

<210> SEQ ID NO 247
<211> LENGTH: 18
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: Carbamidomethylation
<220> FEATURE:
<221> NAME/KEY: MOD_RES
<222> LOCATION: (12)..(12)
<223> OTHER INFORMATION: Carbamidomethylation
<220> FEATURE:
<221> NAME/KEY: MOD_RES
<222> LOCATION: (18)..(18)
<223> OTHER INFORMATION: R(13C6; 15N4)

<400> SEQUENCE: 247

His Tyr Tyr Tyr Ala Gly Val Cys Val Pro Ala Cys Pro Pro Asn Thr
1               5                   10                  15
```

Tyr Arg

```
<210> SEQ ID NO 248
<211> LENGTH: 18
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (18)..(18)
<223> OTHER INFORMATION: R(13C6; 15N4)

<400> SEQUENCE: 248
```

His Tyr Tyr Tyr Ala Gly Val Cys Val Pro Ala Cys Pro Pro Asn Thr
1               5                   10                  15

Tyr Arg

```
<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Carbamidomethylation
<220> FEATURE:
<221> NAME/KEY: MOD_RES
<222> LOCATION: (12)..(12)
<223> OTHER INFORMATION: R(13C6; 15N4)

<400> SEQUENCE: 249
```

Leu Gly Cys Ser Ala Ser Asn Phe Val Phe Ala Arg
1               5                   10

```
<210> SEQ ID NO 250
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: R(13C6; 15N4)

<400> SEQUENCE: 250
```

Leu Gly Cys Ser Ala Ser Asn Phe Val Phe Ala Arg
1               5                   10

```
<210> SEQ ID NO 251
<211> LENGTH: 19
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (19)..(19)
<223> OTHER INFORMATION: K(13C6; 15N2)

<400> SEQUENCE: 251
```

Ser Leu Arg Pro Glu Met Glu Asn Asn Pro Val Leu Ala Pro Pro Ser

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
     Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 252

Thr Thr Ile Asn Asn Glu Tyr Asn Tyr Arg
1               5                   10

<210> SEQ ID NO 253
<211> LENGTH: 18
<212> TYPE: PRT
<213> ORGANISM: Artificial Sequence
<220> FEATURE:
<223> OTHER INFORMATION: Description of Artificial Sequence: Synthetic
     Internal standard peptide sequence
<220> FEATURE:
<221> NAME/KEY: MOD_RES
<222> LOCATION: (18)..(18)
<223> OTHER INFORMATION: R(13C6; 15N4)

<400> SEQUENCE: 253

Val Ala Gly Leu Glu Ser Leu Gly Asp Leu Phe Pro Asn Leu Thr Val
1               5                   10                  15

Ile Arg

<210> SEQ ID NO 254
<211> LENGTH: 16
<212> TYPE: PRT
<213> ORGANISM: Artificial Sequence
<220> FEATURE:
<223> OTHER INFORMATION: Description of Artificial Sequence: Synthetic
     Internal standard peptide sequence
<220> FEATURE:
<221> NAME/KEY: MOD_RES
<222> LOCATION: (16)..(16)
<223> OTHER INFORMATION: K(13C6; 15N2)

<400> SEQUENCE: 254

Tyr Ala Asp Gly Thr Ile Asp Ile Glu Glu Val Thr Glu Asn Pro Lys
1               5                   10                  15

<210> SEQ ID NO 255
<211> LENGTH: 14
<212> TYPE: PRT
<213> ORGANISM: Artificial Sequence
<220> FEATURE:
<223> OTHER INFORMATION: Description of Artificial Sequence: Synthetic
     Internal standard peptide sequence
<220> FEATURE:
<221> NAME/KEY: MOD_RES
<222> LOCATION: (11)..(11)
<223> OTHER INFORMATION: Carbamidomethylation
<220> FEATURE:
<221> NAME/KEY: MOD_RES
<222> LOCATION: (14)..(14)
<223> OTHER INFORMATION: R(13C6; 15N4)

<400> SEQUENCE: 255

(Leu Ser Lys from previous sequence)

```
Tyr Gly Ser Gln Val Glu Asp Gln Arg Glu Cys Val Ser Arg
1               5                   10
```

<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (14)..(14)
<223> OTHER INFORMATION: R(13C6; 15N4)

<400> SEQUENCE: 256

```
Tyr Gly Ser Gln Val Glu Asp Gln Arg Glu Cys Val Ser Arg
1               5                   10
```

<210> SEQ ID NO 257
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: K(13C6; 15N2)

<400> SEQUENCE: 257

```
Ile Asp Ile His Ser Cys Asn His Glu Ala Glu Lys
1               5                   10
```

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 258

```
Gly Val Val Lys Asp Glu Pro Glu Thr Arg
1               5                   10
```

<210> SEQ ID NO 259
<211> LENGTH: 26
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (26)..(26)
<223> OTHER INFORMATION: R(13C6; 15N4)

<400> SEQUENCE: 259

```
Ala Ser Ser Asp Gly Glu Gly Thr Met Ser Arg Pro Ala Ser Val Asp
1               5                   10                  15

Gly Ser Pro Val Ser Pro Ser Thr Asn Arg
            20                  25
```

```
<210> SEQ ID NO 260
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (1)..(1)
<223> OTHER INFORMATION: Carbamidomethylation
<220> FEATURE:
<221> NAME/KEY: MOD_RES
<222> LOCATION: (14)..(14)
<223> OTHER INFORMATION: R(13C6; 15N4)

<400> SEQUENCE: 260

Cys Gly His Ser Glu Asn Phe Phe Phe Ile Glu Val Gly Arg
1               5                   10

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (14)..(14)
<223> OTHER INFORMATION: R(13C6; 15N4)

<400> SEQUENCE: 261

Cys Gly His Ser Glu Asn Phe Phe Phe Ile Glu Val Gly Arg
1               5                   10

<210> SEQ ID NO 262
<211> LENGTH: 27
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (1)..(1)
<223> OTHER INFORMATION: Carbamidomethylation
<220> FEATURE:
<221> NAME/KEY: MOD_RES
<222> LOCATION: (27)..(27)
<223> OTHER INFORMATION: R(13C6; 15N4)

<400> SEQUENCE: 262

Cys Thr Pro Gly Thr Gly Leu Gly Thr Ser Pro Ala Leu Ala Gly Asp
1               5                   10                  15

Glu Ala Ala Ser Ala Ala Asp Leu Asp Asn Arg
            20                  25

<210> SEQ ID NO 263
<211> LENGTH: 27
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (27)..(27)
<223> OTHER INFORMATION: R(13C6; 15N4)

<400> SEQUENCE: 263
```

```
Cys Thr Pro Gly Thr Gly Leu Gly Thr Ser Pro Ala Leu Ala Gly Asp
1               5                   10                  15

Glu Ala Ala Ser Ala Ala Asp Leu Asp Asn Arg
            20                  25

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (15)..(15)
<223> OTHER INFORMATION: R(13C6; 15N4)

<400> SEQUENCE: 264

His His Leu Asn Asn Pro Pro Pro Ser Gln Val Gly Leu Thr Arg
1               5                   10                  15

<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (14)..(14)
<223> OTHER INFORMATION: R(13C6; 15N4)

<400> SEQUENCE: 265

His Ser Ser Glu Thr Phe Ser Ser Thr Pro Ser Ala Thr Arg
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: K(13C6; 15N2)

<400> SEQUENCE: 266

Lys Gly Ser Gly Asp Tyr Met Pro Met Ser Pro Lys
1               5                   10

<210> SEQ ID NO 267
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (2)..(2)
<223> OTHER INFORMATION: Carbamidomethylation
<220> FEATURE:
<221> NAME/KEY: MOD_RES
<222> LOCATION: (21)..(21)
<223> OTHER INFORMATION: K(13C6; 15N2)

<400> SEQUENCE: 267
```

```
Leu Cys Gly Ala Ala Gly Gly Leu Glu Asn Gly Leu Asn Tyr Ile Asp
1               5                   10                  15

Leu Asp Leu Val Lys
            20

<210> SEQ ID NO 268
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (21)..(21)
<223> OTHER INFORMATION: K(13C6; 15N2)

<400> SEQUENCE: 268

Leu Cys Gly Ala Ala Gly Gly Leu Glu Asn Gly Leu Asn Tyr Ile Asp
1               5                   10                  15

Leu Asp Leu Val Lys
            20

<210> SEQ ID NO 269
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: R(13C6; 15N4)

<400> SEQUENCE: 269

Ser Val Ser Ala Pro Gln Gln Ile Ile Asn Pro Ile Arg
1               5                   10

<210> SEQ ID NO 270
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (21)..(21)
<223> OTHER INFORMATION: R(13C6; 15N4)

<400> SEQUENCE: 270

Thr Glu Ser Ile Thr Ala Thr Ser Pro Ala Ser Met Val Gly Gly Lys
1               5                   10                  15

Pro Gly Ser Phe Arg
            20

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: R(13C6; 15N4)
```

```
<400> SEQUENCE: 271

Thr Gly Ile Ala Ala Glu Glu Val Ser Leu Pro Arg
1               5                   10

<210> SEQ ID NO 272
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (14)..(14)
<223> OTHER INFORMATION: R(13C6; 15N4)

<400> SEQUENCE: 272

Ser Tyr Pro Glu Glu Gly Leu Glu Met His Pro Leu Glu Arg
1               5                   10

<210> SEQ ID NO 273
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (14)..(14)
<223> OTHER INFORMATION: K(13C6; 15N2)

<400> SEQUENCE: 273

Thr His Ser Ala Gly Thr Ser Pro Thr Ile Thr His Gln Lys
1               5                   10

<210> SEQ ID NO 274
<211> LENGTH: 26
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (26)..(26)
<223> OTHER INFORMATION: R(13C6; 15N4)

<400> SEQUENCE: 274

Ala Ser Ser Asp Gly Glu Gly Thr Met Ser Arg Pro Ala Ser Val Asp
1               5                   10                  15

Gly Ser Pro Val Ser Pro Ser Thr Asn Arg
            20                  25

<210> SEQ ID NO 275
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
```

```
<221> NAME/KEY: MOD_RES
<222> LOCATION: (14)..(14)
<223> OTHER INFORMATION: R(13C6; 15N4)

<400> SEQUENCE: 275

His Ser Ser Glu Thr Phe Ser Ser Thr Pro Ser Ala Thr Arg
1               5                   10

<210> SEQ ID NO 276
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: Phosphorylation
<220> FEATURE:
<221> NAME/KEY: MOD_RES
<222> LOCATION: (12)..(12)
<223> OTHER INFORMATION: K(13C6; 15N2)

<400> SEQUENCE: 276

Lys Gly Ser Gly Asp Tyr Met Pro Met Ser Pro Lys
1               5                   10

<210> SEQ ID NO 277
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (7)..(7)
<223> OTHER INFORMATION: Methionine sulfoxide
<220> FEATURE:
<221> NAME/KEY: MOD_RES
<222> LOCATION: (9)..(9)
<223> OTHER INFORMATION: Methionine sulfoxide
<220> FEATURE:
<221> NAME/KEY: MOD_RES
<222> LOCATION: (10)..(10)
<223> OTHER INFORMATION: Phosphorylation
<220> FEATURE:
<221> NAME/KEY: MOD_RES
<222> LOCATION: (12)..(12)
<223> OTHER INFORMATION: K(13C6; 15N2)

<400> SEQUENCE: 277

Lys Gly Ser Gly Asp Tyr Met Pro Met Ser Pro Lys
1               5                   10

<210> SEQ ID NO 278
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (2)..(2)
<223> OTHER INFORMATION: Carbamidomethylation
<220> FEATURE:
<221> NAME/KEY: MOD_RES
<222> LOCATION: (14)..(14)
<223> OTHER INFORMATION: Phosphorylation
<220> FEATURE:
<221> NAME/KEY: MOD_RES
```

```
<222> LOCATION: (21)..(21)
<223> OTHER INFORMATION: K(13C6; 15N2)

<400> SEQUENCE: 278

Leu Cys Gly Ala Ala Gly Gly Leu Glu Asn Gly Leu Asn Tyr Ile Asp
1               5                   10                  15

Leu Asp Leu Val Lys
            20

<210> SEQ ID NO 279
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (14)..(14)
<223> OTHER INFORMATION: Phosphorylation
<220> FEATURE:
<221> NAME/KEY: MOD_RES
<222> LOCATION: (21)..(21)
<223> OTHER INFORMATION: K(13C6; 15N2)

<400> SEQUENCE: 279

Leu Cys Gly Ala Ala Gly Gly Leu Glu Asn Gly Leu Asn Tyr Ile Asp
1               5                   10                  15

Leu Asp Leu Val Lys
            20

<210> SEQ ID NO 280
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: Phosphorylation
<220> FEATURE:
<221> NAME/KEY: MOD_RES
<222> LOCATION: (21)..(21)
<223> OTHER INFORMATION: R(13C6; 15N4)

<400> SEQUENCE: 280

Thr Glu Ser Ile Thr Ala Thr Ser Pro Ala Ser Met Val Gly Gly Lys
1               5                   10                  15

Pro Gly Ser Phe Arg
            20

<210> SEQ ID NO 281
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: Phosphorylation
<220> FEATURE:
<221> NAME/KEY: MOD_RES
<222> LOCATION: (12)..(12)
<223> OTHER INFORMATION: Methionine sulfoxide
<220> FEATURE:
<221> NAME/KEY: MOD_RES
```

```
<222> LOCATION: (21)..(21)
<223> OTHER INFORMATION: R(13C6; 15N4)

<400> SEQUENCE: 281

Thr Glu Ser Ile Thr Ala Thr Ser Pro Ala Ser Met Val Gly Gly Lys
1               5                   10                  15
Pro Gly Ser Phe Arg
            20

<210> SEQ ID NO 282
<211> LENGTH: 18
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (18)..(18)
<223> OTHER INFORMATION: R(13C6; 15N4)

<400> SEQUENCE: 282

Ala Pro Ala Gln Thr Pro Ala Glu Pro Thr Pro Gly Tyr Glu Val Gly
1               5                   10                  15
Gln Arg

<210> SEQ ID NO 283
<211> LENGTH: 15
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (15)..(15)
<223> OTHER INFORMATION: K(13C6; 15N2)

<400> SEQUENCE: 283

Asp Ser Phe Arg Ala Arg Ser Thr Ser Leu Asn Glu Arg Pro Lys
1               5                   10                  15

<210> SEQ ID NO 284
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (16)..(16)
<223> OTHER INFORMATION: R(13C6; 15N4)

<400> SEQUENCE: 284

Glu Ala Pro Ala Lys Leu Glu Ser Gln Ala Gly Gln Gln Val Ser Arg
1               5                   10                  15

<210> SEQ ID NO 285
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (11)..(11)
<223> OTHER INFORMATION: R(13C6; 15N4)
```

```
<400> SEQUENCE: 285

Gly Tyr Thr Ile Ser Asp Ser Ala Pro Ser Arg
1               5                   10

<210> SEQ ID NO 286
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: V(13C5; 15N)

<400> SEQUENCE: 286

Leu Ile Ser Ser Val Glu Asp Phe Thr Glu Phe Val
1               5                   10

<210> SEQ ID NO 287
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: R(13C6; 15N4)

<400> SEQUENCE: 287

Leu Val Thr Val Thr Thr Ser Val Gly Thr Gly Thr Arg
1               5                   10

<210> SEQ ID NO 288
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (21)..(21)
<223> OTHER INFORMATION: R(13C6; 15N4)

<400> SEQUENCE: 288

Ser Gln Ser Gly Thr Leu Asp Gly Glu Ser Ala Ala Trp Ser Ala Ser
1               5                   10                  15

Gly Glu Asp Ser Arg
            20

<210> SEQ ID NO 289
<211> LENGTH: 15
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (15)..(15)
<223> OTHER INFORMATION: K(13C6; 15N2)

<400> SEQUENCE: 289

Ser Val Gln Leu Leu Asp Gln Ile Pro Ser Tyr Asp Thr His Lys
```

<210> SEQ ID NO 290
<211> LENGTH: 21
<212> TYPE: PRT
<213> ORGANISM: Artificial Sequence
<220> FEATURE:
<223> OTHER INFORMATION: Description of Artificial Sequence: Synthetic
    Internal standard peptide sequence
<220> FEATURE:
<221> NAME/KEY: MOD_RES
<222> LOCATION: (21)..(21)
<223> OTHER INFORMATION: R(13C6; 15N4)

<400> SEQUENCE: 290

Val Gly Ala Leu Asp Val Pro Ala Ser Gln Phe Leu Gly Ser Ala Thr
1               5                   10                  15

Ser Pro Gly Pro Arg
            20

<210> SEQ ID NO 291
<211> LENGTH: 23
<212> TYPE: PRT
<213> ORGANISM: Artificial Sequence
<220> FEATURE:
<223> OTHER INFORMATION: Description of Artificial Sequence: Synthetic
    Internal standard peptide sequence
<220> FEATURE:
<221> NAME/KEY: MOD_RES
<222> LOCATION: (23)..(23)
<223> OTHER INFORMATION: K(13C6; 15N2)

<400> SEQUENCE: 291

Val Val Ser Ser Glu Gly Gly Arg Pro Ser Val Asp Leu Ser Phe Gln
1               5                   10                  15

Pro Ser Gln Pro Leu Ser Lys
            20

<210> SEQ ID NO 292
<211> LENGTH: 10
<212> TYPE: PRT
<213> ORGANISM: Artificial Sequence
<220> FEATURE:
<223> OTHER INFORMATION: Description of Artificial Sequence: Synthetic
    Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 292

Tyr Thr Glu Phe Leu Thr Gly Leu Gly Arg
1               5                   10

<210> SEQ ID NO 293
<211> LENGTH: 11
<212> TYPE: PRT
<213> ORGANISM: Artificial Sequence
<220> FEATURE:
<223> OTHER INFORMATION: Description of Artificial Sequence: Synthetic
    Internal standard peptide sequence
<220> FEATURE:
<221> NAME/KEY: MOD_RES
<222> LOCATION: (11)..(11)
<223> OTHER INFORMATION: K(13C6; 15N2)

<400> SEQUENCE: 293

Tyr Val Phe Ser Asn Phe Thr Ala Val Pro Lys
1               5                   10

-continued

```
<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: K(13C6; 15N2)

<400> SEQUENCE: 294

Ser Asn Pro Thr Asp Ile Tyr Pro Ser Lys
1               5                   10

<210> SEQ ID NO 295
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: R(13C6; 15N4)

<400> SEQUENCE: 295

Phe Asn Ser Cys Tyr Leu Asp Glu Tyr Ile Ala Arg
1               5                   10

<210> SEQ ID NO 296
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: R(13C6; 15N4)

<400> SEQUENCE: 296

Gly Gln Pro Glu Gly Pro Leu Pro Ser Ser Ser Pro Arg
1               5                   10

<210> SEQ ID NO 297
<211> LENGTH: 25
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (25)..(25)
<223> OTHER INFORMATION: R(13C6; 15N4)

<400> SEQUENCE: 297

Ser Leu Leu Gly Leu Asp Ser Gly Glu Leu Gln Ser Gly Pro Glu Ser
1               5                   10                  15

Ser Ser Ser Pro Gly Val His Val Arg
            20                  25

<210> SEQ ID NO 298
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: Phosphorylation
<220> FEATURE:
<221> NAME/KEY: MOD_RES
<222> LOCATION: (15)..(15)
<223> OTHER INFORMATION: K(13C6; 15N2)

<400> SEQUENCE: 298

Asp Ser Phe Arg Ala Arg Ser Thr Ser Leu Asn Glu Arg Pro Lys
1               5                   10                  15

<210> SEQ ID NO 299
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (11)..(11)
<223> OTHER INFORMATION: R(13C6; 15N4)

<400> SEQUENCE: 299

Gly Tyr Thr Ile Ser Asp Ser Ala Pro Ser Arg
1               5                   10

<210> SEQ ID NO 300
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (12)..(12)
<223> OTHER INFORMATION: V(13C5; 15N)

<400> SEQUENCE: 300

Leu Ile Ser Ser Val Glu Asp Phe Thr Glu Phe Val
1               5                   10

<210> SEQ ID NO 301
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (4)..(4)
<223> OTHER INFORMATION: Phosphorylation
<220> FEATURE:
<221> NAME/KEY: MOD_RES
<222> LOCATION: (12)..(12)
<223> OTHER INFORMATION: V(13C5; 15N)
```

<400> SEQUENCE: 301

Leu Ile Ser Ser Val Glu Asp Phe Thr Glu Phe Val
1               5                   10

<210> SEQ ID NO 302
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(4)
<223> OTHER INFORMATION: Phosphorylation
<220> FEATURE:
<221> NAME/KEY: MOD_RES
<222> LOCATION: (12)..(12)
<223> OTHER INFORMATION: V(13C5; 15N)

<400> SEQUENCE: 302

Leu Ile Ser Ser Val Glu Asp Phe Thr Glu Phe Val
1               5                   10

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (9)..(9)
<223> OTHER INFORMATION: K(13C6; 15N2)

<400> SEQUENCE: 303

Ser Thr Ser Leu Asn Glu Arg Pro Lys
1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: K(13C6; 15N2)

<400> SEQUENCE: 304

Ser Thr Ser Leu Asn Glu Arg Pro Lys
1               5

<210> SEQ ID NO 305
<211> LENGTH: 19
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (16)..(16)

<223> OTHER INFORMATION: Carbamidomethylation
<220> FEATURE:
<221> NAME/KEY: MOD_RES
<222> LOCATION: (19)..(19)
<223> OTHER INFORMATION: K(13C6; 15N2)

<400> SEQUENCE: 305

Ala Val Leu Ala Leu His Gln Asp Leu Phe Ser Leu Ala Gln Gln Cys
1               5                   10                  15
Ile Asp Lys

<210> SEQ ID NO 306
<211> LENGTH: 19
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (19)..(19)
<223> OTHER INFORMATION: K(13C6; 15N2)

<400> SEQUENCE: 306

Ala Val Leu Ala Leu His Gln Asp Leu Phe Ser Leu Ala Gln Gln Cys
1               5                   10                  15
Ile Asp Lys

<210> SEQ ID NO 307
<211> LENGTH: 18
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (18)..(18)
<223> OTHER INFORMATION: R(13C6; 15N4)

<400> SEQUENCE: 307

Asp Leu Glu Leu Ala Val Pro Gly Thr Tyr Asp Pro Asn Gln Pro Ile
1               5                   10                  15
Ile Arg

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: R(13C6; 15N4)

<400> SEQUENCE: 308

Gly Asn Asn Leu Gln Asp Thr Leu Arg
1               5

<210> SEQ ID NO 309
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence

```
<220> FEATURE:
<221> NAME/KEY: MOD_RES
<222> LOCATION: (16)..(16)
<223> OTHER INFORMATION: K(13C6; 15N2)

<400> SEQUENCE: 309

Gly Pro Thr Pro Ala Ile Leu Glu Ser Leu Ile Ser Ile Asn Asn Lys
1               5                   10                  15

<210> SEQ ID NO 310
<211> LENGTH: 17
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (17)..(17)
<223> OTHER INFORMATION: R(13C6; 15N4)

<400> SEQUENCE: 310

Gly Tyr Thr Leu Ala Asp Glu Glu Glu Asp Pro Leu Ile Tyr Gln His
1               5                   10                  15

Arg

<210> SEQ ID NO 311
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: R(13C6; 15N4)

<400> SEQUENCE: 311

Ile His Gly Ala Leu Leu Ile Leu Asn Glu Leu Val Arg
1               5                   10

<210> SEQ ID NO 312
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (14)..(14)
<223> OTHER INFORMATION: K(13C6; 15N2)

<400> SEQUENCE: 312

Ile Gln Ser Ile Ala Pro Ser Leu Gln Val Ile Thr Ser Lys
1               5                   10

<210> SEQ ID NO 313
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: R(13C6; 15N4)
```

```
<400> SEQUENCE: 313

Leu Phe Asp Ala Pro Glu Ala Pro Leu Pro Ser Arg
1               5                   10

<210> SEQ ID NO 314
<211> LENGTH: 18
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (18)..(18)
<223> OTHER INFORMATION: K(13C6; 15N2)

<400> SEQUENCE: 314

Leu Gly Glu Trp Gln Leu Asn Leu Gln Gly Ile Asn Glu Ser Thr Ile
1               5                   10                  15

Pro Lys

<210> SEQ ID NO 315
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (11)..(11)
<223> OTHER INFORMATION: R(13C6; 15N4)

<400> SEQUENCE: 315

Leu Ile His Gln Leu Leu Thr Asp Ile Gly Arg
1               5                   10

<210> SEQ ID NO 316
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 316

Ser Pro Ser Ser Glu Val Trp Phe Asp Arg
1               5                   10

<210> SEQ ID NO 317
<211> LENGTH: 24
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (24)..(24)
<223> OTHER INFORMATION: K(13C6; 15N2)

<400> SEQUENCE: 317

Thr Asp Ser Tyr Ser Ala Gly Gln Ser Val Glu Ile Leu Asp Gly Val
1               5                   10                  15
```

```
Glu Leu Gly Glu Pro Ala His Lys
            20

<210> SEQ ID NO 318
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: R(13C6; 15N4)

<400> SEQUENCE: 318

Thr Leu Val Leu Leu Leu Gly Val Asp Pro Ser Arg
1               5                   10

<210> SEQ ID NO 319
<211> LENGTH: 18
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (18)..(18)
<223> OTHER INFORMATION: K(13C6; 15N2)

<400> SEQUENCE: 319

Val Glu Val Phe Glu His Ala Val Asn Asn Thr Ala Gly Asp Asp Leu
1               5                   10                  15

Ala Lys

<210> SEQ ID NO 320
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: K(13C6; 15N2)

<400> SEQUENCE: 320

Val Leu Gly Leu Leu Gly Ala Leu Asp Pro Tyr Lys
1               5                   10

<210> SEQ ID NO 321
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (11)..(11)
<223> OTHER INFORMATION: K(13C6; 15N2)

<400> SEQUENCE: 321

Trp Thr Leu Val Asn Asp Glu Thr Gln Ala Lys
1               5                   10

<210> SEQ ID NO 322
```

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 322

Glu Thr Ser Phe Asn Gln Ala Tyr Gly Arg
1               5                   10

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: R(13C6; 15N4)

<400> SEQUENCE: 323

Thr Leu Asp Gln Ser Pro Glu Leu Arg
1               5

<210> SEQ ID NO 324
<211> LENGTH: 24
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (24)..(24)
<223> OTHER INFORMATION: K(13C6; 15N2)

<400> SEQUENCE: 324

Thr Asp Ser Tyr Ser Ala Gly Gln Ser Val Glu Ile Leu Asp Gly Val
1               5                   10                  15

Glu Leu Gly Glu Pro Ala His Lys
            20

<210> SEQ ID NO 325
<211> LENGTH: 24
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (1)..(1)
<223> OTHER INFORMATION: Phosphorylation
<220> FEATURE:
<221> NAME/KEY: MOD_RES
<222> LOCATION: (24)..(24)
<223> OTHER INFORMATION: K(13C6; 15N2)

<400> SEQUENCE: 325

Thr Asp Ser Tyr Ser Ala Gly Gln Ser Val Glu Ile Leu Asp Gly Val
```

```
1               5                   10                  15
Glu Leu Gly Glu Pro Ala His Lys
            20

<210> SEQ ID NO 326
<211> LENGTH: 24
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (1)..(1)
<223> OTHER INFORMATION: Phosphorylation
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (24)..(24)
<223> OTHER INFORMATION: K(13C6; 15N2)

<400> SEQUENCE: 326

Thr Asp Ser Tyr Ser Ala Gly Gln Ser Val Glu Ile Leu Asp Gly Val
1               5                   10                  15

Glu Leu Gly Glu Pro Ala His Lys
            20

<210> SEQ ID NO 327
<211> LENGTH: 17
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (17)..(17)
<223> OTHER INFORMATION: K(13C6; 15N2)

<400> SEQUENCE: 327

Asp Ile Lys Pro Gln Asn Leu Leu Val Asp Pro Asp Thr Ala Val Leu
1               5                   10                  15

Lys

<210> SEQ ID NO 328
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (7)..(7)
<223> OTHER INFORMATION: Carbamidomethylation
<220> FEATURE:
<221> NAME/KEY: MOD_RES
<222> LOCATION: (16)..(16)
<223> OTHER INFORMATION: R(13C6; 15N4)

<400> SEQUENCE: 328

Leu Ser Pro Leu Glu Ala Cys Ala His Ser Phe Phe Asp Glu Leu Arg
1               5                   10                  15

<210> SEQ ID NO 329
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (16)..(16)
<223> OTHER INFORMATION: R(13C6; 15N4)

<400> SEQUENCE: 329

Leu Ser Pro Leu Glu Ala Cys Ala His Ser Phe Phe Asp Glu Leu Arg
1               5                   10                  15

<210> SEQ ID NO 330
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (11)..(11)
<223> OTHER INFORMATION: Carbamidomethylation
<220> FEATURE:
<221> NAME/KEY: MOD_RES
<222> LOCATION: (13)..(13)
<223> OTHER INFORMATION: R(13C6; 15N4)

<400> SEQUENCE: 330

Ser Leu Ala Tyr Ile His Ser Gln Gly Val Cys His Arg
1               5                   10

<210> SEQ ID NO 331
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: R(13C6; 15N4)

<400> SEQUENCE: 331

Ser Leu Ala Tyr Ile His Ser Gln Gly Val Cys His Arg
1               5                   10

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: K(13C6; 15N2)

<400> SEQUENCE: 332

Ser Gln Glu Val Ala Tyr Thr Asp Ile Lys
1               5                   10

<210> SEQ ID NO 333
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: Carbamidomethylation
<220> FEATURE:
<221> NAME/KEY: MOD_RES
<222> LOCATION: (20)..(20)
<223> OTHER INFORMATION: R(13C6; 15N4)

<400> SEQUENCE: 333

Thr Pro Pro Glu Ala Ile Ala Leu Cys Ser Ser Leu Leu Glu Tyr Thr
1               5                   10                  15

Pro Ser Ser Arg
            20

<210> SEQ ID NO 334
<211> LENGTH: 20
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (20)..(20)
<223> OTHER INFORMATION: R(13C6; 15N4)

<400> SEQUENCE: 334

Thr Pro Pro Glu Ala Ile Ala Leu Cys Ser Ser Leu Leu Glu Tyr Thr
1               5                   10                  15

Pro Ser Ser Arg
            20

<210> SEQ ID NO 335
<211> LENGTH: 32
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (32)..(32)
<223> OTHER INFORMATION: K(13C6; 15N2)

<400> SEQUENCE: 335

Thr Ser Ser Phe Ala Glu Pro Gly Gly Gly Gly Gly Gly Gly Gly Gly
1               5                   10                  15

Gly Pro Gly Gly Ser Ala Ser Gly Pro Gly Gly Thr Gly Gly Gly Lys
            20                  25                  30

<210> SEQ ID NO 336
<211> LENGTH: 14
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (14)..(14)
<223> OTHER INFORMATION: R(13C6; 15N4)

<400> SEQUENCE: 336

Val Thr Thr Val Val Ala Thr Leu Gly Gln Gly Pro Glu Arg
1               5                   10
```

```
<210> SEQ ID NO 337
<211> LENGTH: 18
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (18)..(18)
<223> OTHER INFORMATION: R(13C6; 15N4)

<400> SEQUENCE: 337

Asp Ser Gly Lys Val Thr Thr Val Val Ala Thr Leu Gly Gln Gly Pro
1               5                   10                  15

Glu Arg

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: K(13C6; 15N2)

<400> SEQUENCE: 338

Tyr Phe Phe Tyr Ser Ser Gly Glu Lys
1               5

<210> SEQ ID NO 339
<211> LENGTH: 32
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (32)..(32)
<223> OTHER INFORMATION: K(13C6; 15N2)

<400> SEQUENCE: 339

Thr Ser Ser Phe Ala Glu Pro Gly Gly Gly Gly Gly Gly Gly Gly Gly
1               5                   10                  15

Gly Pro Gly Gly Ser Ala Ser Gly Pro Gly Gly Thr Gly Gly Gly Lys
                20                  25                  30

<210> SEQ ID NO 340
<211> LENGTH: 18
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (18)..(18)
<223> OTHER INFORMATION: R(13C6; 15N4)

<400> SEQUENCE: 340

Asp Glu Val Tyr Leu Asn Leu Val Leu Asp Tyr Val Pro Glu Thr Val
```

```
1               5                   10                  15

Tyr Arg

<210> SEQ ID NO 341
<211> LENGTH: 17
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (17)..(17)
<223> OTHER INFORMATION: K(13C6; 15N2)

<400> SEQUENCE: 341

Asp Ile Lys Pro Gln Asn Leu Leu Leu Asp Pro Asp Thr Ala Val Leu
1               5                   10                  15

Lys

<210> SEQ ID NO 342
<211> LENGTH: 29
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (29)..(29)
<223> OTHER INFORMATION: R(13C6; 15N4)

<400> SEQUENCE: 342

Asp Thr Pro Ala Leu Phe Asn Phe Thr Thr Gln Glu Leu Ser Ser Asn
1               5                   10                  15

Pro Pro Leu Ala Thr Ile Leu Ile Pro Pro His Ala Arg
            20                  25

<210> SEQ ID NO 343
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (2)..(2)
<223> OTHER INFORMATION: Carbamidomethylation
<220> FEATURE:
<221> NAME/KEY: MOD_RES
<222> LOCATION: (11)..(11)
<223> OTHER INFORMATION: K(13C6; 15N2)

<400> SEQUENCE: 343

Leu Cys Asp Ser Gly Glu Leu Val Ala Ile Lys
1               5                   10

<210> SEQ ID NO 344
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (11)..(11)
<223> OTHER INFORMATION: K(13C6; 15N2)
```

<400> SEQUENCE: 344

Leu Cys Asp Ser Gly Glu Leu Val Ala Ile Lys
1               5                   10

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: R(13C6; 15N4)

<400> SEQUENCE: 345

Leu Leu Glu Tyr Thr Pro Thr Ala Arg
1               5

<210> SEQ ID NO 346
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (11)..(11)
<223> OTHER INFORMATION: Carbamidomethylation
<220> FEATURE:
<221> NAME/KEY: MOD_RES
<222> LOCATION: (13)..(13)
<223> OTHER INFORMATION: R(13C6; 15N4)

<400> SEQUENCE: 346

Ser Leu Ala Tyr Ile His Ser Phe Gly Ile Cys His Arg
1               5                   10

<210> SEQ ID NO 347
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: R(13C6; 15N4)

<400> SEQUENCE: 347

Ser Leu Ala Tyr Ile His Ser Phe Gly Ile Cys His Arg
1               5                   10

<210> SEQ ID NO 348
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: Carbamidomethylation
<220> FEATURE:
<221> NAME/KEY: MOD_RES
<222> LOCATION: (21)..(21)

<223> OTHER INFORMATION: K(13C6; 15N2)

<400> SEQUENCE: 348

Thr Thr Ser Phe Ala Glu Ser Cys Lys Pro Val Gln Gln Pro Ser Ala
1               5                   10                  15

Phe Gly Ser Met Lys
            20

<210> SEQ ID NO 349
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (21)..(21)
<223> OTHER INFORMATION: K(13C6; 15N2)

<400> SEQUENCE: 349

Thr Thr Ser Phe Ala Glu Ser Cys Lys Pro Val Gln Gln Pro Ser Ala
1               5                   10                  15

Phe Gly Ser Met Lys
            20

<210> SEQ ID NO 350
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: Carbamidomethylation
<220> FEATURE:
<221> NAME/KEY: MOD_RES
<222> LOCATION: (20)..(20)
<223> OTHER INFORMATION: Methionine sulfoxide
<220> FEATURE:
<221> NAME/KEY: MOD_RES
<222> LOCATION: (21)..(21)
<223> OTHER INFORMATION: K(13C6; 15N2)

<400> SEQUENCE: 350

Thr Thr Ser Phe Ala Glu Ser Cys Lys Pro Val Gln Gln Pro Ser Ala
1               5                   10                  15

Phe Gly Ser Met Lys
            20

<210> SEQ ID NO 351
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (20)..(20)
<223> OTHER INFORMATION: Methionine sulfoxide
<220> FEATURE:
<221> NAME/KEY: MOD_RES
<222> LOCATION: (21)..(21)
<223> OTHER INFORMATION: K(13C6; 15N2)

<400> SEQUENCE: 351

```
Thr Thr Ser Phe Ala Glu Ser Cys Lys Pro Val Gln Gln Pro Ser Ala
1               5                   10                  15

Phe Gly Ser Met Lys
            20

<210> SEQ ID NO 352
<211> LENGTH: 24
<212> TYPE: PRT
<213> ORGANISM: Artificial Sequence
<220> FEATURE:
<223> OTHER INFORMATION: Description of Artificial Sequence: Synthetic
      Internal standard peptide sequence

<400> SEQUENCE: 352

Val Thr Thr Val Val Ala Thr Pro Gly Gln Gly Pro Asp Arg Pro Gln
1               5                   10                  15

Glu Val Ser Tyr Thr Asp Thr Lys
            20

<210> SEQ ID NO 353
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: R(13C6; 15N4)

<400> SEQUENCE: 353

Lys Leu Asp His Cys Asn Ile Val Arg
1               5

<210> SEQ ID NO 354
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: R(13C6; 15N4)

<400> SEQUENCE: 354

Asp Ser Ser Gly Thr Gly His Phe Thr Ser Gly Val Arg
1               5                   10

<210> SEQ ID NO 355
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (8)..(8)
<223> OTHER INFORMATION: Carbamidomethylation
<220> FEATURE:
<221> NAME/KEY: MOD_RES
<222> LOCATION: (20)..(20)
<223> OTHER INFORMATION: Methionine sulfoxide
```

```
<220> FEATURE:
<221> NAME/KEY: MOD_RES
<222> LOCATION: (21)..(21)
<223> OTHER INFORMATION: K(13C6; 15N2)

<400> SEQUENCE: 355

Thr Thr Ser Phe Ala Glu Ser Cys Lys Pro Val Gln Gln Pro Ser Ala
1               5                   10                  15

Phe Gly Ser Met Lys
            20

<210> SEQ ID NO 356
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (20)..(20)
<223> OTHER INFORMATION: Methionine sulfoxide
<220> FEATURE:
<221> NAME/KEY: MOD_RES
<222> LOCATION: (21)..(21)
<223> OTHER INFORMATION: K(13C6; 15N2)

<400> SEQUENCE: 356

Thr Thr Ser Phe Ala Glu Ser Cys Lys Pro Val Gln Gln Pro Ser Ala
1               5                   10                  15

Phe Gly Ser Met Lys
            20

<210> SEQ ID NO 357
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (8)..(8)
<223> OTHER INFORMATION: Carbamidomethylation
<220> FEATURE:
<221> NAME/KEY: MOD_RES
<222> LOCATION: (21)..(21)
<223> OTHER INFORMATION: K(13C6; 15N2)

<400> SEQUENCE: 357

Thr Thr Ser Phe Ala Glu Ser Cys Lys Pro Val Gln Gln Pro Ser Ala
1               5                   10                  15

Phe Gly Ser Met Lys
            20

<210> SEQ ID NO 358
<211> LENGTH: 21
<212> TYPE: PRT
<213> ORGANISM: Artificial Sequence
<220> FEATURE:
<223> OTHER INFORMATION: Description of Artificial Sequence: Synthetic
      Internal standard peptide sequence
```

```
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (21)..(21)
<223> OTHER INFORMATION: K(13C6; 15N2)

<400> SEQUENCE: 358

Thr Thr Ser Phe Ala Glu Ser Cys Lys Pro Val Gln Gln Pro Ser Ala
1               5                   10                  15

Phe Gly Ser Met Lys
            20

<210> SEQ ID NO 359
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: Carbamidomethylation
<220> FEATURE:
<221> NAME/KEY: MOD_RES
<222> LOCATION: (11)..(11)
<223> OTHER INFORMATION: R(13C6; 15N4)

<400> SEQUENCE: 359

Gly Glu Pro Asn Val Ser Tyr Ile Cys Ser Arg
1               5                   10

<210> SEQ ID NO 360
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (11)..(11)
<223> OTHER INFORMATION: R(13C6; 15N4)

<400> SEQUENCE: 360

Gly Glu Pro Asn Val Ser Tyr Ile Cys Ser Arg
1               5                   10

<210> SEQ ID NO 361
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (7)..(7)
<223> OTHER INFORMATION: Phosphorylation
<220> FEATURE:
<221> NAME/KEY: MOD_RES
<222> LOCATION: (9)..(9)
<223> OTHER INFORMATION: Carbamidomethylation
<220> FEATURE:
<221> NAME/KEY: MOD_RES
<222> LOCATION: (11)..(11)
<223> OTHER INFORMATION: R(13C6; 15N4)

<400> SEQUENCE: 361
```

```
Gly Glu Pro Asn Val Ser Tyr Ile Cys Ser Arg
1               5                   10

<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (7)..(7)
<223> OTHER INFORMATION: Phosphorylation
<220> FEATURE:
<221> NAME/KEY: MOD_RES
<222> LOCATION: (11)..(11)
<223> OTHER INFORMATION: R(13C6; 15N4)

<400> SEQUENCE: 362

Gly Glu Pro Asn Val Ser Tyr Ile Cys Ser Arg
1               5                   10

<210> SEQ ID NO 363
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (6)..(6)
<223> OTHER INFORMATION: Phosphorylation
<220> FEATURE:
<221> NAME/KEY: MOD_RES
<222> LOCATION: (9)..(9)
<223> OTHER INFORMATION: Carbamidomethylation
<220> FEATURE:
<221> NAME/KEY: MOD_RES
<222> LOCATION: (11)..(11)
<223> OTHER INFORMATION: R(13C6; 15N4)

<400> SEQUENCE: 363

Gly Glu Pro Asn Val Ser Tyr Ile Cys Ser Arg
1               5                   10

<210> SEQ ID NO 364
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (6)..(6)
<223> OTHER INFORMATION: Phosphorylation
<220> FEATURE:
<221> NAME/KEY: MOD_RES
<222> LOCATION: (11)..(11)
<223> OTHER INFORMATION: R(13C6; 15N4)

<400> SEQUENCE: 364

Gly Glu Pro Asn Val Ser Tyr Ile Cys Ser Arg
1               5                   10

<210> SEQ ID NO 365
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (6)..(7)
<223> OTHER INFORMATION: Phosphorylation
<220> FEATURE:
<221> NAME/KEY: MOD_RES
<222> LOCATION: (9)..(9)
<223> OTHER INFORMATION: Carbamidomethylation
<220> FEATURE:
<221> NAME/KEY: MOD_RES
<222> LOCATION: (11)..(11)
<223> OTHER INFORMATION: R(13C6; 15N4)

<400> SEQUENCE: 365

Gly Glu Pro Asn Val Ser Tyr Ile Cys Ser Arg
1               5                   10

<210> SEQ ID NO 366
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (6)..(7)
<223> OTHER INFORMATION: Phosphorylation
<220> FEATURE:
<221> NAME/KEY: MOD_RES
<222> LOCATION: (11)..(11)
<223> OTHER INFORMATION: R(13C6; 15N4)

<400> SEQUENCE: 366

Gly Glu Pro Asn Val Ser Tyr Ile Cys Ser Arg
1               5                   10

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (11)..(11)
<223> OTHER INFORMATION: R(13C6; 15N4)

<400> SEQUENCE: 367

Thr Pro Pro Glu Ala Ile Ala Leu Cys Ser Arg
1               5                   10

<210> SEQ ID NO 368
<211> LENGTH: 11
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: Carbamidomethylation
<220> FEATURE:
<221> NAME/KEY: MOD_RES
<222> LOCATION: (11)..(11)
<223> OTHER INFORMATION: R(13C6; 15N4)

<400> SEQUENCE: 368
```

```
Thr Pro Pro Glu Ala Ile Ala Leu Cys Ser Arg
1               5                   10
```

<210> SEQ ID NO 369
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 369

```
Asp Gly Phe Tyr Pro Ala Pro Asp Phe Arg
1               5                   10
```

<210> SEQ ID NO 370
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (16)..(16)
<223> OTHER INFORMATION: K(13C6; 15N2)

<400> SEQUENCE: 370

```
Asp Leu Lys Pro Glu Asn Ile Met Leu Asn His Gln Gly His Val Lys
1               5                   10                  15
```

<210> SEQ ID NO 371
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 371

```
Phe Glu Ile Ser Glu Thr Ser Val Asn Arg
1               5                   10
```

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (9)..(9)
<223> OTHER INFORMATION: R(13C6; 15N4)

<400> SEQUENCE: 372

```
Phe Ser Pro Gly Asp Phe Trp Gly Arg
1               5
```

<210> SEQ ID NO 373
<211> LENGTH: 10

```
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 373

His Ile Asn Trp Glu Glu Leu Leu Ala Arg
1               5                   10

<210> SEQ ID NO 374
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (16)..(16)
<223> OTHER INFORMATION: K(13C6; 15N2)

<400> SEQUENCE: 374

His Pro Phe Ile Val Asp Leu Ile Tyr Ala Phe Gln Thr Gly Gly Lys
1               5                   10                  15

<210> SEQ ID NO 375
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (5)..(5)
<223> OTHER INFORMATION: Carbamidomethylation
<220> FEATURE:
<221> NAME/KEY: MOD_RES
<222> LOCATION: (10)..(10)
<223> OTHER INFORMATION: R(13C6; 15N4)

<400> SEQUENCE: 375

Ile Arg Pro Glu Cys Phe Glu Leu Leu Arg
1               5                   10

<210> SEQ ID NO 376
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 376

Ile Arg Pro Glu Cys Phe Glu Leu Leu Arg
1               5                   10

<210> SEQ ID NO 377
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      Internal standard peptide sequence
<220> FEATURE:
<221> NAME/KEY: MOD_RES
<222> LOCATION: (18)..(18)
<223> OTHER INFORMATION: R(13C6; 15N4)

<400> SEQUENCE: 377

Leu Gly Ala Gly Pro Gly Asp Ala Gly Glu Val Gln Ala His Pro Phe
1               5                   10                  15

Phe Arg

<210> SEQ ID NO 378
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: R(13C6; 15N4)

<400> SEQUENCE: 378

Leu Asn Leu Pro Pro Tyr Leu Thr Gln Glu Ala Arg
1               5                   10

<210> SEQ ID NO 379
<211> LENGTH: 8
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (7)..(7)
<223> OTHER INFORMATION: Carbamidomethylation
<220> FEATURE:
<221> NAME/KEY: MOD_RES
<222> LOCATION: (8)..(8)
<223> OTHER INFORMATION: K(13C6; 15N2)

<400> SEQUENCE: 379

Leu Thr Asp Phe Gly Leu Cys Lys
1               5

<210> SEQ ID NO 380
<211> LENGTH: 8
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: K(13C6; 15N2)

<400> SEQUENCE: 380

Leu Thr Asp Phe Gly Leu Cys Lys
1               5

<210> SEQ ID NO 381
<211> LENGTH: 35
<212> TYPE: PRT
<213> ORGANISM: Artificial Sequence
<220> FEATURE:
<223> OTHER INFORMATION: Description of Artificial Sequence: Synthetic
```

Internal standard peptide sequence
<220> FEATURE:
<221> NAME/KEY: MOD_RES
<222> LOCATION: (35)..(35)
<223> OTHER INFORMATION: K(13C6; 15N2)

<400> SEQUENCE: 381

Gln Thr Pro Val Asp Ser Pro Asp Asp Ser Thr Leu Ser Glu Ser Ala
1               5                   10                  15

Asn Gln Val Phe Leu Gly Phe Thr Tyr Val Ala Pro Ser Val Leu Glu
            20                  25                  30

Ser Val Lys
        35

<210> SEQ ID NO 382
<211> LENGTH: 7
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (7)..(7)
<223> OTHER INFORMATION: K(13C6; 15N2)

<400> SEQUENCE: 382

Thr Pro Val Ser Pro Val Lys
1               5

<210> SEQ ID NO 383
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (16)..(16)
<223> OTHER INFORMATION: R(13C6; 15N4)

<400> SEQUENCE: 383

Thr Pro Val Ser Pro Val Lys Phe Ser Pro Gly Asp Phe Trp Gly Arg
1               5                   10                  15

<210> SEQ ID NO 384
<211> LENGTH: 35
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (24)..(24)
<223> OTHER INFORMATION: Phosphorylation
<220> FEATURE:
<221> NAME/KEY: MOD_RES
<222> LOCATION: (35)..(35)
<223> OTHER INFORMATION: K(13C6; 15N2)

<400> SEQUENCE: 384

Gln Thr Pro Val Asp Ser Pro Asp Asp Ser Thr Leu Ser Glu Ser Ala
1               5                   10                  15

Asn Gln Val Phe Leu Gly Phe Thr Tyr Val Ala Pro Ser Val Leu Glu
            20                  25                  30

Ser Val Lys

<210> SEQ ID NO 385
<211> LENGTH: 35
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (6)..(6)
<223> OTHER INFORMATION: Phosphorylation
<220> FEATURE:
<221> NAME/KEY: MOD_RES
<222> LOCATION: (35)..(35)
<223> OTHER INFORMATION: K(13C6; 15N2)

<400> SEQUENCE: 385

Gln Thr Pro Val Asp Ser Pro Asp Asp Ser Thr Leu Ser Glu Ser Ala
1               5                   10                  15

Asn Gln Val Phe Leu Gly Phe Thr Tyr Val Ala Pro Ser Val Leu Glu
            20                  25                  30

Ser Val Lys
        35

<210> SEQ ID NO 386
<211> LENGTH: 35
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (6)..(6)
<223> OTHER INFORMATION: Phosphorylation
<220> FEATURE:
<221> NAME/KEY: MOD_RES
<222> LOCATION: (24)..(24)
<223> OTHER INFORMATION: Phosphorylation
<220> FEATURE:
<221> NAME/KEY: MOD_RES
<222> LOCATION: (35)..(35)
<223> OTHER INFORMATION: K(13C6; 15N2)

<400> SEQUENCE: 386

Gln Thr Pro Val Asp Ser Pro Asp Asp Ser Thr Leu Ser Glu Ser Ala
1               5                   10                  15

Asn Gln Val Phe Leu Gly Phe Thr Tyr Val Ala Pro Ser Val Leu Glu
            20                  25                  30

Ser Val Lys
        35

<210> SEQ ID NO 387
<211> LENGTH: 7
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (1)..(1)
<223> OTHER INFORMATION: Phosphorylation
<220> FEATURE:
<221> NAME/KEY: MOD_RES
<222> LOCATION: (7)..(7)
<223> OTHER INFORMATION: K(13C6; 15N2)

```
<400> SEQUENCE: 387

Thr Pro Val Ser Pro Val Lys
1               5

<210> SEQ ID NO 388
<211> LENGTH: 7
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (4)..(4)
<223> OTHER INFORMATION: Phosphorylation
<220> FEATURE:
<221> NAME/KEY: MOD_RES
<222> LOCATION: (7)..(7)
<223> OTHER INFORMATION: K(13C6; 15N2)

<400> SEQUENCE: 388

Thr Pro Val Ser Pro Val Lys
1               5

<210> SEQ ID NO 389
<211> LENGTH: 7
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (1)..(1)
<223> OTHER INFORMATION: Phosphorylation
<220> FEATURE:
<221> NAME/KEY: MOD_RES
<222> LOCATION: (4)..(4)
<223> OTHER INFORMATION: Phosphorylation
<220> FEATURE:
<221> NAME/KEY: MOD_RES
<222> LOCATION: (7)..(7)
<223> OTHER INFORMATION: K(13C6; 15N2)

<400> SEQUENCE: 389

Thr Pro Val Ser Pro Val Lys
1               5

<210> SEQ ID NO 390
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (4)..(4)
<223> OTHER INFORMATION: Phosphorylation
<220> FEATURE:
<221> NAME/KEY: MOD_RES
<222> LOCATION: (16)..(16)
<223> OTHER INFORMATION: R(13C6; 15N4)

<400> SEQUENCE: 390

Thr Pro Val Ser Pro Val Lys Phe Ser Pro Gly Asp Phe Trp Gly Arg
1               5                   10                  15

<210> SEQ ID NO 391
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (1)..(1)
<223> OTHER INFORMATION: Phosphorylation
<220> FEATURE:
<221> NAME/KEY: MOD_RES
<222> LOCATION: (4)..(4)
<223> OTHER INFORMATION: Phosphorylation
<220> FEATURE:
<221> NAME/KEY: MOD_RES
<222> LOCATION: (16)..(16)
<223> OTHER INFORMATION: R(13C6; 15N4)

<400> SEQUENCE: 391

Thr Pro Val Ser Pro Val Lys Phe Ser Pro Gly Asp Phe Trp Gly Arg
1               5                   10                  15

<210> SEQ ID NO 392
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (1)..(1)
<223> OTHER INFORMATION: Phosphorylation
<220> FEATURE:
<221> NAME/KEY: MOD_RES
<222> LOCATION: (16)..(16)
<223> OTHER INFORMATION: R(13C6; 15N4)

<400> SEQUENCE: 392

Thr Pro Val Ser Pro Val Lys Phe Ser Pro Gly Asp Phe Trp Gly Arg
1               5                   10                  15

<210> SEQ ID NO 393
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: R(13C6; 15N4)

<400> SEQUENCE: 393

Asp Ile Pro Gly Leu Thr Asp Thr Thr Val Pro Arg
1               5                   10

<210> SEQ ID NO 394
<211> LENGTH: 8
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (4)..(4)
<223> OTHER INFORMATION: Carbamidomethylation
<220> FEATURE:
<221> NAME/KEY: MOD_RES
<222> LOCATION: (8)..(8)
<223> OTHER INFORMATION: R(13C6; 15N4)
```

```
<400> SEQUENCE: 394

Gly His Ser Cys Tyr Arg Pro Arg
1               5

<210> SEQ ID NO 395
<211> LENGTH: 8
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: R(13C6; 15N4)

<400> SEQUENCE: 395

Gly His Ser Cys Tyr Arg Pro Arg
1               5

<210> SEQ ID NO 396
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: Carbamidomethylation
<220> FEATURE:
<221> NAME/KEY: MOD_RES
<222> LOCATION: (12)..(12)
<223> OTHER INFORMATION: K(13C6; 15N2)

<400> SEQUENCE: 396

Leu Asn Ile Ser Phe Pro Ala Thr Gly Cys Gln Lys
1               5                   10

<210> SEQ ID NO 397
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: K(13C6; 15N2)

<400> SEQUENCE: 397

Leu Asn Ile Ser Phe Pro Ala Thr Gly Cys Gln Lys
1               5                   10

<210> SEQ ID NO 398
<211> LENGTH: 15
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (15)..(15)
<223> OTHER INFORMATION: K(13C6; 15N2)

<400> SEQUENCE: 398

Met Ala Thr Glu Val Ala Ala Asp Ala Leu Gly Glu Glu Trp Lys
```

```
1               5                   10                  15
```

```
<210> SEQ ID NO 399
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (13)..(13)
<223> OTHER INFORMATION: K(13C6; 15N2)

<400> SEQUENCE: 399

Arg Arg Arg Leu Ser Ser Leu Arg Ala Ser Thr Ser Lys
1               5                   10

<210> SEQ ID NO 400
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (5)..(5)
<223> OTHER INFORMATION: Phosphorylation
<220> FEATURE:
<221> NAME/KEY: MOD_RES
<222> LOCATION: (13)..(13)
<223> OTHER INFORMATION: K(13C6; 15N2)

<400> SEQUENCE: 400

Arg Arg Arg Leu Ser Ser Leu Arg Ala Ser Thr Ser Lys
1               5                   10

<210> SEQ ID NO 401
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (6)..(6)
<223> OTHER INFORMATION: Phosphorylation
<220> FEATURE:
<221> NAME/KEY: MOD_RES
<222> LOCATION: (13)..(13)
<223> OTHER INFORMATION: K(13C6; 15N2)

<400> SEQUENCE: 401

Arg Arg Arg Leu Ser Ser Leu Arg Ala Ser Thr Ser Lys
1               5                   10

<210> SEQ ID NO 402
<211> LENGTH: 13
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (5)..(6)
<223> OTHER INFORMATION: Phosphorylation
<220> FEATURE:
<221> NAME/KEY: MOD_RES
<222> LOCATION: (13)..(13)
```

```
<223> OTHER INFORMATION: K(13C6; 15N2)

<400> SEQUENCE: 402

Arg Arg Arg Leu Ser Ser Leu Arg Ala Ser Thr Ser Lys
1               5                   10

<210> SEQ ID NO 403
<211> LENGTH: 30
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (30)..(30)
<223> OTHER INFORMATION: R(13C6; 15N4)

<400> SEQUENCE: 403

Ala Ala Thr Ala Ala Arg Pro Pro Ala Pro Pro Ala Pro Gln Pro
1               5                   10                  15

Pro Ser Pro Thr Pro Ser Pro Pro Arg Pro Thr Leu Ala Arg
            20                  25                  30

<210> SEQ ID NO 404
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (1)..(1)
<223> OTHER INFORMATION: Carbamidomethylation
<220> FEATURE:
<221> NAME/KEY: MOD_RES
<222> LOCATION: (10)..(10)
<223> OTHER INFORMATION: R(13C6; 15N4)

<400> SEQUENCE: 404

Cys Leu His Asp Ile Ala Leu Ala His Arg
1               5                   10

<210> SEQ ID NO 405
<211> LENGTH: 10
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 405

Cys Leu His Asp Ile Ala Leu Ala His Arg
1               5                   10

<210> SEQ ID NO 406
<211> LENGTH: 15
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (15)..(15)
```

```
<223> OTHER INFORMATION: R(13C6; 15N4)

<400> SEQUENCE: 406

Glu Ala Glu Asp Thr Gln Val Phe Gly Asp Leu Pro Arg Pro Arg
1               5                   10                  15

<210> SEQ ID NO 407
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: K(13C6; 15N2)

<400> SEQUENCE: 407

Ser Leu Pro Val Ser Val Pro Val Trp Gly Phe Lys
1               5                   10

<210> SEQ ID NO 408
<211> LENGTH: 16
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (16)..(16)
<223> OTHER INFORMATION: R(13C6; 15N4)

<400> SEQUENCE: 408

Ser Ser Asp Glu Glu Asn Gly Pro Pro Ser Ser Pro Asp Leu Asp Arg
1               5                   10                  15

<210> SEQ ID NO 409
<211> LENGTH: 20
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (20)..(20)
<223> OTHER INFORMATION: R(13C6; 15N4)

<400> SEQUENCE: 409

Thr Glu Ala Arg Ser Ser Asp Glu Glu Asn Gly Pro Pro Ser Ser Pro
1               5                   10                  15

Asp Leu Asp Arg
            20

<210> SEQ ID NO 410
<211> LENGTH: 28
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (21)..(21)
<223> OTHER INFORMATION: Carbamidomethylation
<220> FEATURE:
<221> NAME/KEY: MOD_RES
<222> LOCATION: (28)..(28)
```

```
<223> OTHER INFORMATION: R(13C6; 15N4)

<400> SEQUENCE: 410

Thr Gly Thr Glu Leu Val Leu Leu Thr Ala Ala Pro Pro Pro Pro
1               5                   10                  15

Arg Pro Gly Pro Cys Ala Tyr Ala Ala His Gly Arg
            20                  25

<210> SEQ ID NO 411
<211> LENGTH: 28
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (28)..(28)
<223> OTHER INFORMATION: R(13C6; 15N4)

<400> SEQUENCE: 411

Thr Gly Thr Glu Leu Val Leu Leu Thr Ala Ala Pro Pro Pro Pro
1               5                   10                  15

Arg Pro Gly Pro Cys Ala Tyr Ala Ala His Gly Arg
            20                  25

<210> SEQ ID NO 412
<211> LENGTH: 8
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: K(13C6; 15N2)

<400> SEQUENCE: 412

Leu Asn Thr Ser Asp Phe Gln Lys
1               5

<210> SEQ ID NO 413
<211> LENGTH: 23
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (23)..(23)
<223> OTHER INFORMATION: K(13C6; 15N2)

<400> SEQUENCE: 413

Glu Ala Glu Asp Thr Gln Val Phe Gly Asp Leu Pro Arg Pro Arg Leu
1               5                   10                  15

Asn Thr Ser Asp Phe Gln Lys
            20

<210> SEQ ID NO 414
<211> LENGTH: 8
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
```

<221> NAME/KEY: MOD_RES
<222> LOCATION: (8)..(8)
<223> OTHER INFORMATION: R(13C6; 15N4)

<400> SEQUENCE: 414

Gly Ala Leu Ala Glu Ala Ala Arg
1               5

<210> SEQ ID NO 415
<211> LENGTH: 18
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (18)..(18)
<223> OTHER INFORMATION: R(13C6; 15N4)

<400> SEQUENCE: 415

Ala Ser Gly Arg Pro Glu Glu Leu Trp Glu Ala Val Val Gly Ala Ala
1               5                   10                  15

Glu Arg

<210> SEQ ID NO 416
<211> LENGTH: 8
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (3)..(3)
<223> OTHER INFORMATION: Phosphorylation
<220> FEATURE:
<221> NAME/KEY: MOD_RES
<222> LOCATION: (8)..(8)
<223> OTHER INFORMATION: K(13C6; 15N2)

<400> SEQUENCE: 416

Leu Asn Thr Ser Asp Phe Gln Lys
1               5

<210> SEQ ID NO 417
<211> LENGTH: 23
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (18)..(18)
<223> OTHER INFORMATION: Phosphorylation
<220> FEATURE:
<221> NAME/KEY: MOD_RES
<222> LOCATION: (23)..(23)
<223> OTHER INFORMATION: K(13C6; 15N2)

<400> SEQUENCE: 417

Glu Ala Glu Asp Thr Gln Val Phe Gly Asp Leu Pro Arg Pro Arg Leu
1               5                   10                  15

Asn Thr Ser Asp Phe Gln Lys
            20

<210> SEQ ID NO 418
<211> LENGTH: 24

```
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (24)..(24)
<223> OTHER INFORMATION: K(13C6; 15N2)

<400> SEQUENCE: 418

Tyr Ser Asp Thr Thr Asp Ser Asp Pro Glu Asn Glu Pro Phe Asp Glu
1               5                   10                  15

Asp Gln His Thr Gln Ile Thr Lys
            20

<210> SEQ ID NO 419
<211> LENGTH: 25
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (24)..(24)
<223> OTHER INFORMATION: K(13C6; 15N2)

<400> SEQUENCE: 419

Tyr Ser Asp Thr Thr Asp Ser Asp Pro Glu Asn Glu Pro Phe Asp Glu
1               5                   10                  15

Asp Gln His Thr Gln Ile Thr Lys Val
            20                  25

<210> SEQ ID NO 420
<211> LENGTH: 8
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (8)..(8)
<223> OTHER INFORMATION: R(13C6; 15N4)

<400> SEQUENCE: 420

Asn Asn Ile Asp Asp Val Val Arg
1               5

<210> SEQ ID NO 421
<211> LENGTH: 12
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (12)..(12)
<223> OTHER INFORMATION: R(13C6; 15N4)

<400> SEQUENCE: 421

Ala Gln Glu Ala Leu Asp Phe Tyr Gly Glu Val Arg
1               5                   10

<210> SEQ ID NO 422
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (10)..(10)
<223> OTHER INFORMATION: R(13C6; 15N4)

<400> SEQUENCE: 422

Ile Tyr Ser Ser Asn Ser Gly Pro Thr Arg
1               5                   10

<210> SEQ ID NO 423
<211> LENGTH: 24
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (2)..(2)
<223> OTHER INFORMATION: Phosphorylation
<220> FEATURE:
<221> NAME/KEY: MOD_RES
<222> LOCATION: (24)..(24)
<223> OTHER INFORMATION: K(13C6; 15N2)

<400> SEQUENCE: 423

Tyr Ser Asp Thr Thr Asp Ser Asp Pro Glu Asn Glu Pro Phe Asp Glu
1               5                   10                  15

Asp Gln His Thr Gln Ile Thr Lys
            20

<210> SEQ ID NO 424
<211> LENGTH: 25
<212> TYPE: PRT
<213> ORGANISM: Artificial Sequence
<220> FEATURE:
<223> OTHER INFORMATION: Description of Artificial Sequence: Synthetic
      Internal standard peptide sequence
<220> FEATURE:
<221> NAME/KEY: MOD_RES
<222> LOCATION: (2)..(2)
<223> OTHER INFORMATION: Phosphorylation
<220> FEATURE:
<221> NAME/KEY: MOD_RES
<222> LOCATION: (24)..(24)
<223> OTHER INFORMATION: K(13C6; 15N2)

<400> SEQUENCE: 424

Tyr Ser Asp Thr Thr Asp Ser Asp Pro Glu Asn Glu Pro Phe Asp Glu
1               5                   10                  15

Asp Gln His Thr Gln Ile Thr Lys Val
            20                  25
```